(12) United States Patent
Chang et al.

(10) Patent No.: US 12,411,549 B2
(45) Date of Patent: Sep. 9, 2025

(54) WEARABLE BAND STRUCTURE HAVING A BAND PORTION INCLUDING EMBEDDED STRUCTURAL MEMBERS WITH SIGNAL-PROCESSING COMPONENTS AND ANOTHER BAND PORTION NOT INCLUDING ANY ELECTRICAL COMPONENTS, AND SYSTEMS, DEVICES, AND METHODS OF MANUFACTURING THEREOF

(71) Applicant: Meta Platforms Technologies, LLC, Menlo Park, CA (US)

(72) Inventors: Eric Chang, Raritan, NJ (US); Audrey Caroline Christine Louchart, Seattle, WA (US); Phelan Miller, Duvall, WA (US); Andrew Rosenkranz, Westfield, NJ (US); Marc-Aurelien Vivant, Brooklyn, NJ (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 18/500,057

(22) Filed: Nov. 1, 2023

(65) Prior Publication Data

US 2025/0076983 A1 Mar. 6, 2025

Related U.S. Application Data

(60) Provisional application No. 63/594,892, filed on Oct. 31, 2023, provisional application No. 63/580,346, (Continued)

(51) Int. Cl.
*G06F 3/01* (2006.01)
*G04G 21/02* (2010.01)

(52) U.S. Cl.
CPC .......... *G06F 3/015* (2013.01); *G04G 21/025* (2013.01); *G06F 3/017* (2013.01)

(58) Field of Classification Search
CPC ........ G06F 3/015; G06F 3/017; G04G 21/025
See application file for complete search history.

(56) References Cited

U.S. PATENT DOCUMENTS 10,152,082 B2 * 12/2018 Bailey ................... G06F 1/1656
10,765,859 B2 * 9/2020 Bouton ................... A61B 5/686
(Continued)

FOREIGN PATENT DOCUMENTS

CN 113423341 A 9/2021

OTHER PUBLICATIONS

International Preliminary Report on Patentability for International Application No. PCT/US2023/36709, mailed May 15, 2025, 13 pages.

(Continued)

*Primary Examiner* — Amy Onyekaba
(74) *Attorney, Agent, or Firm* — Morgan, Lewis & Bockius LLP

(57) ABSTRACT

An example band structure is provided which includes a first portion having an embedded structural member for holding one or more signal-processing components in fixed positions within the first portion of the band structure. The first portion also includes the one or more signal-processing components, which are coupled to the embedded structural member, and the one or more signal-processing components are configured to at least partially process neuromuscular signals. And the first portion includes one or more neuromuscular-signal-sensing electrodes attached to the first portion of the band structure and electrically coupled to the one or more signal-processing components. The band structure also includes a second portion that does not include any electrical compo- (Continued)

nents, where the first portion of the band structure and the second portion of the band structure are each configured to couple directly to one another to form a loop sized to accommodate a wrist of a user.

20 Claims, 42 Drawing Sheets

Related U.S. Application Data filed on Sep. 1, 2023, provisional application No. 63/421,972, filed on Nov. 2, 2022, provisional application No. 63/421,971, filed on Nov. 2, 2022, provisional application No. 63/421,970, filed on Nov. 2, 2022, provisional application No. 63/421,969, filed on Nov. 2, 2022.

(56) References Cited

U.S. PATENT DOCUMENTS

| | | | |
|---|---|---|---|
| 11,045,137 B2 | 6/2021 | Barbre et al. | |
| 11,150,730 B1* | 10/2021 | Anderson | G06F 3/017 |
| 2014/0257129 A1* | 9/2014 | Choi | A61B 5/7225 |
| | | | 600/546 |
| 2015/0025355 A1* | 1/2015 | Bailey | A61B 5/681 |
| | | | 361/749 |
| 2015/0057770 A1* | 2/2015 | Bailey | A61B 5/389 |
| | | | 700/83 |
| 2015/0070270 A1* | 3/2015 | Bailey | A61B 5/1123 |
| | | | 345/156 |
| 2015/0148641 A1* | 5/2015 | Morun | H05K 1/167 |
| | | | 600/372 |
| 2015/0169074 A1* | 6/2015 | Ataee | G06F 3/017 |
| | | | 345/156 |
| 2015/0370326 A1* | 12/2015 | Chapeskie | G06F 1/163 |
| | | | 345/156 |
| 2016/0322343 A1* | 11/2016 | Scanlan | H01L 24/19 |
| 2018/0020951 A1* | 1/2018 | Kaifosh | A61B 5/389 |
| | | | 607/48 |
| 2018/0154132 A1* | 6/2018 | Bouton | A61N 1/36031 |
| 2019/0227627 A1* | 7/2019 | Kaifosh | A61B 5/1128 |
| 2019/0357787 A1* | 11/2019 | Barachant | G06F 3/011 |
| 2019/0365318 A1* | 12/2019 | Guo | A61B 5/296 |
| 2019/0384901 A1* | 12/2019 | Osborn | G06F 3/017 |
| 2020/0046265 A1* | 2/2020 | Kaifosh | A61B 5/1126 |
| 2020/0097081 A1* | 3/2020 | Stone | G06F 3/015 |
| 2020/0097082 A1* | 3/2020 | Berenzweig | G06T 19/006 |
| 2020/0097083 A1* | 3/2020 | Mao | G06F 3/017 |
| 2020/0111260 A1* | 4/2020 | Osborn | A61B 5/4519 |
| 2020/0310540 A1* | 10/2020 | Hussami | G06F 3/017 |
| 2021/0064132 A1* | 3/2021 | Rubin | G06F 3/016 |
| 2021/0158630 A1* | 5/2021 | Muhammad | G06F 3/017 |
| 2021/0378571 A1* | 12/2021 | King | A61B 5/332 |
| 2021/0397256 A1* | 12/2021 | Barachant | A61B 5/389 |
| 2022/0019284 A1* | 1/2022 | Kaifosh | G06F 3/016 |
| 2022/0091564 A1* | 3/2022 | Vasavada | G06F 3/015 |
| 2022/0151554 A1* | 5/2022 | Jang | G06F 1/1698 |
| 2022/0191296 A1* | 6/2022 | Stefanini | H04L 67/535 |
| 2023/0019413 A1* | 1/2023 | Stern | H04W 4/029 |
| 2023/0105223 A1* | 4/2023 | Dogrusoz | G06F 1/163 |
| | | | 345/156 |
| 2023/0185381 A1* | 6/2023 | Cho | G06F 3/014 |
| | | | 345/156 |

OTHER PUBLICATIONS

International Search Report and Written Opinion for International Application No. PCT/US2023/36709, mailed Jun. 19, 2024, 19 pages.

\* cited by examiner

500 ⟶

510 Overmold a carrier component onto two neuromuscular signal contact points to produce the neuromuscular signal sensor structure.

512 After the overmolding, each of the two neuromuscular signal contact points has a first shape and the carrier component has a second shape.

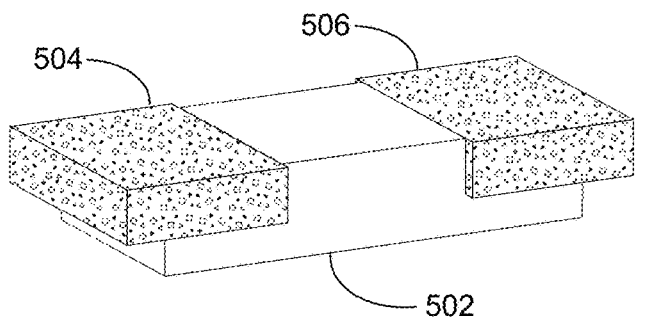

520 Mill the neuromuscular signal sensor structure such that each of the two neuromuscular signal contact points has a third shape and the carrier component has a fourth shape distinct from the second shape.

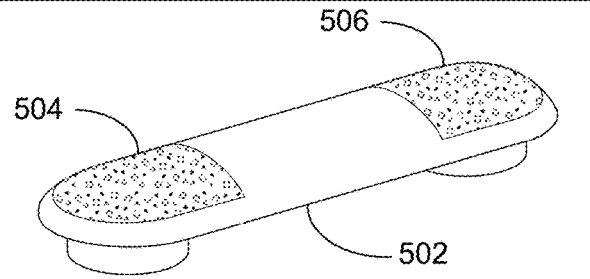

522 After the milling, the neuromuscular signal sensor structure becomes a seamless structure that is configured to allow multiple neuromuscular signal sensors to be placed on a wearable device.

524 Each of the two neuromuscular signal contact points extends above a wrist-facing surface of the wearable device, such that when the wearable device is worn each of the two contact points is at a predetermined skin depression depth.

530 Coat the machined dual-channel neuromuscular signal sensor to prevent corrosion.

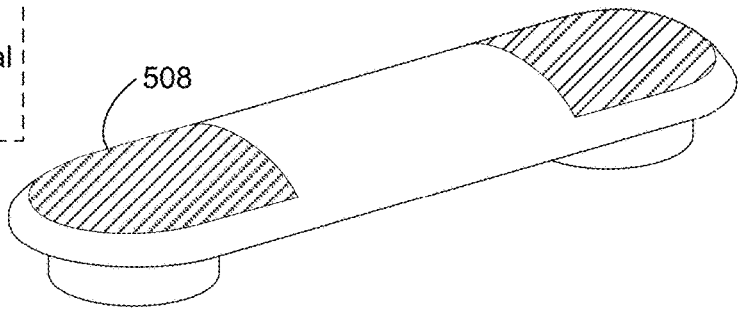

Figure 5

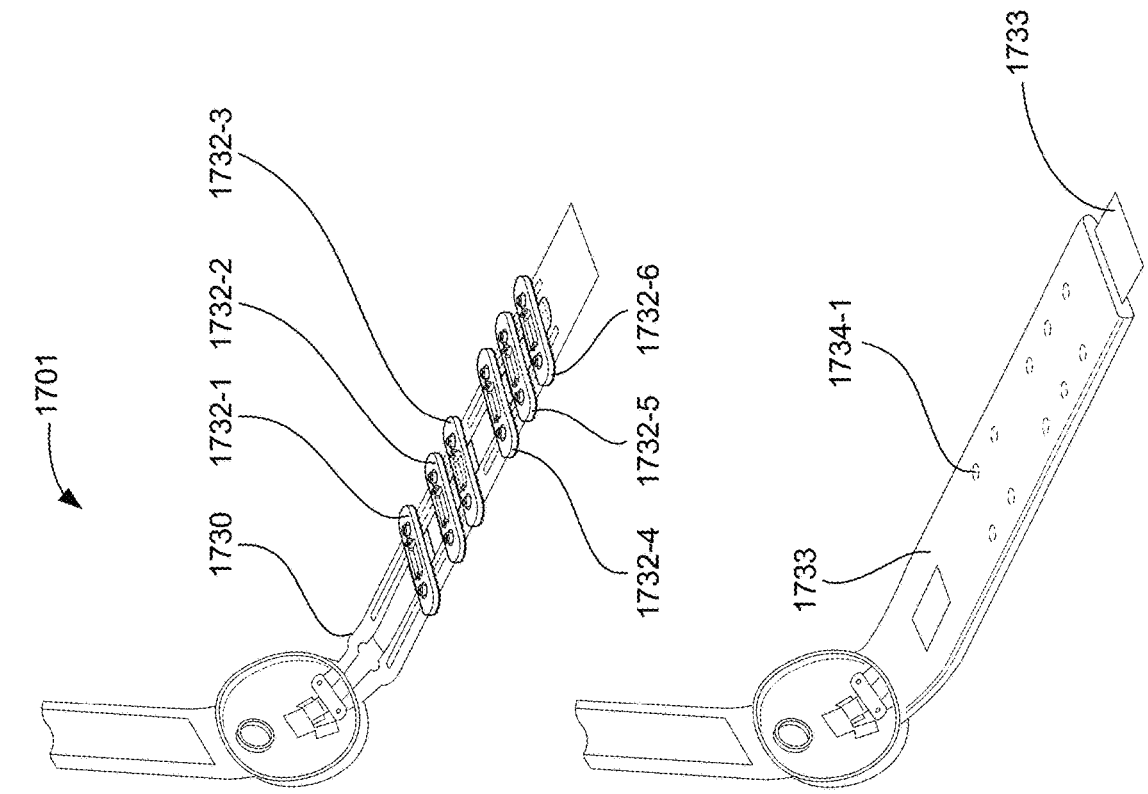
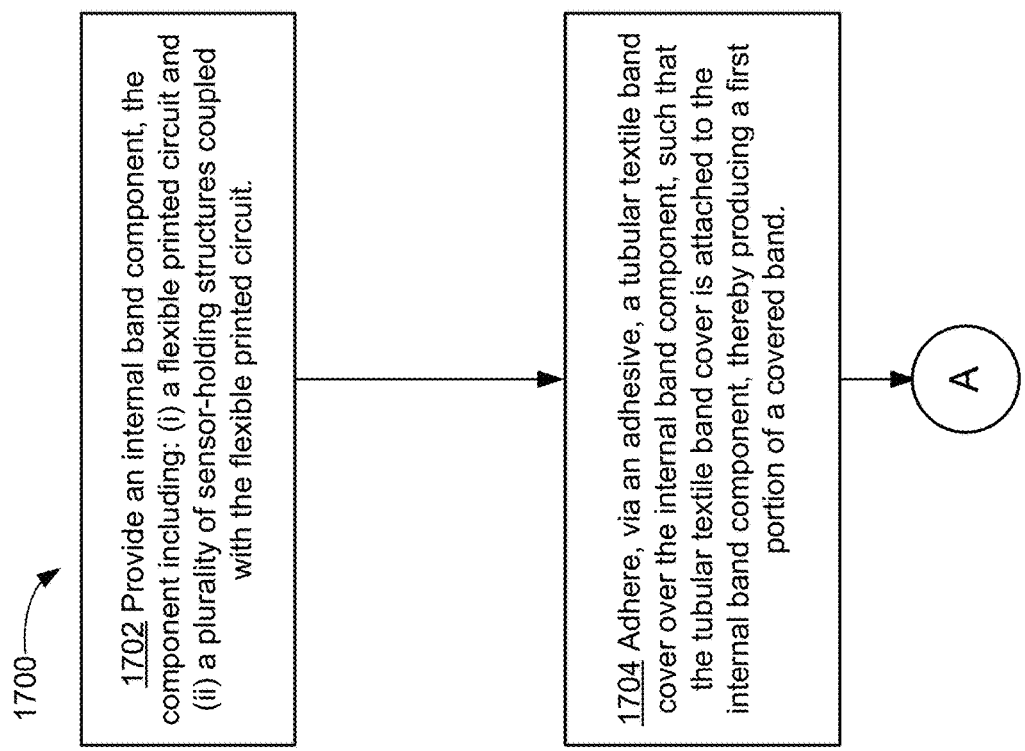
Figure 17A

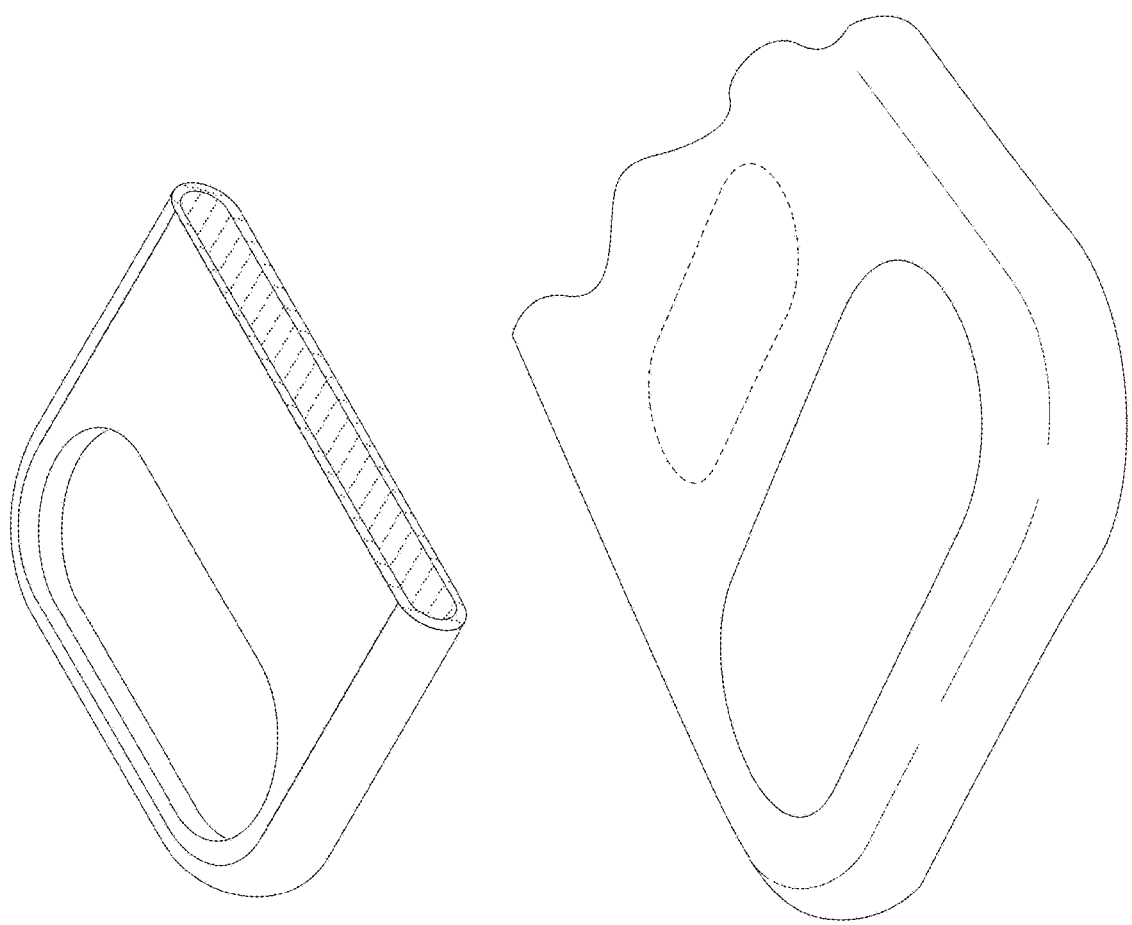
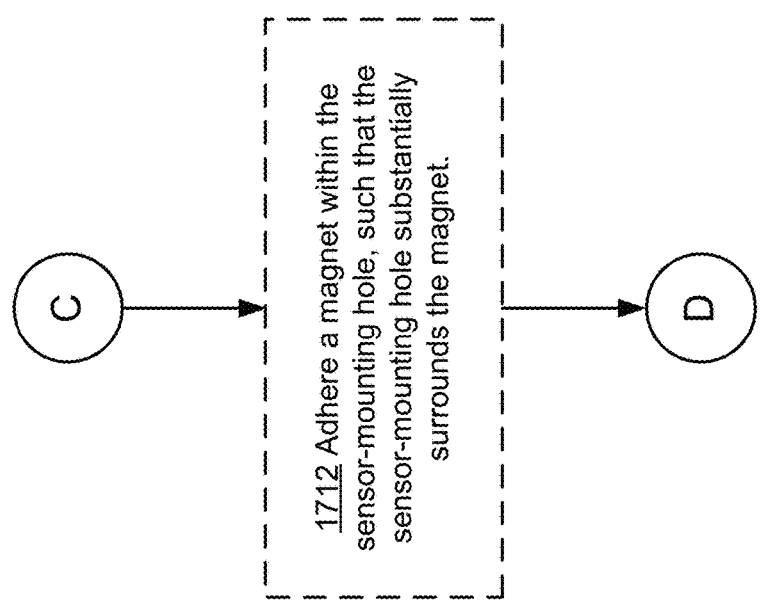
Figure 17D

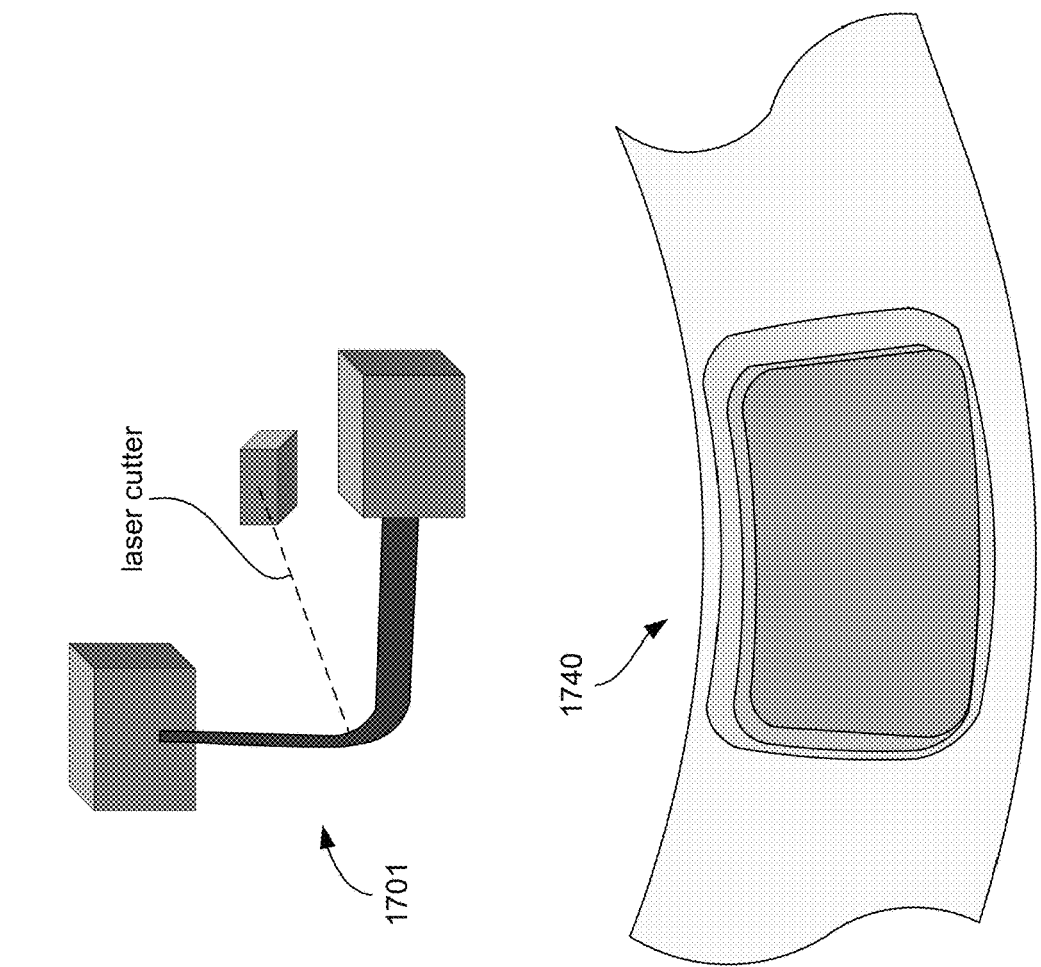
Figure 17E
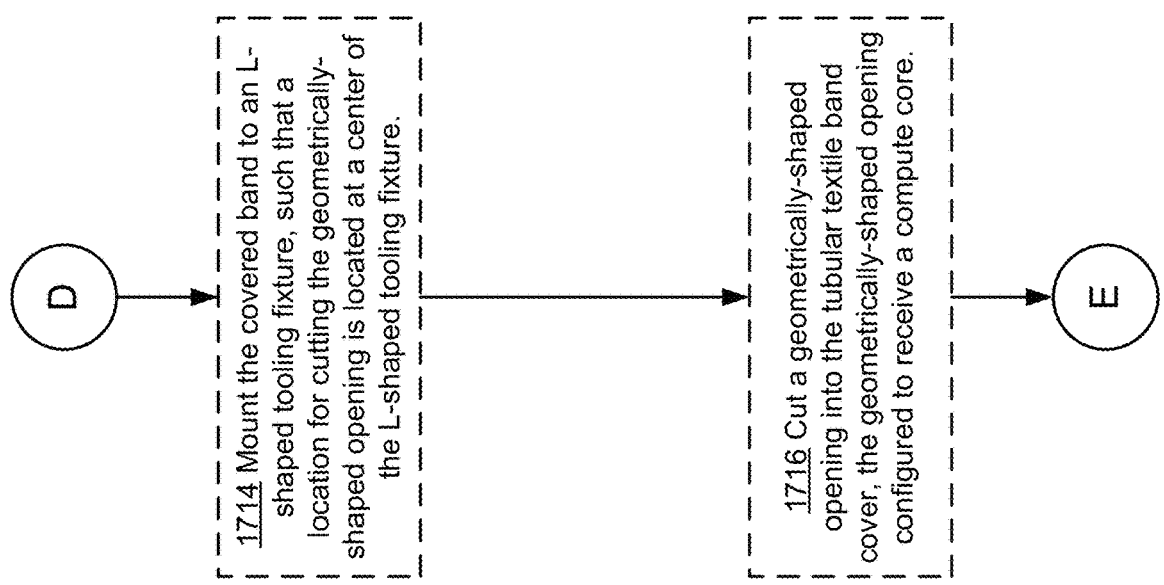

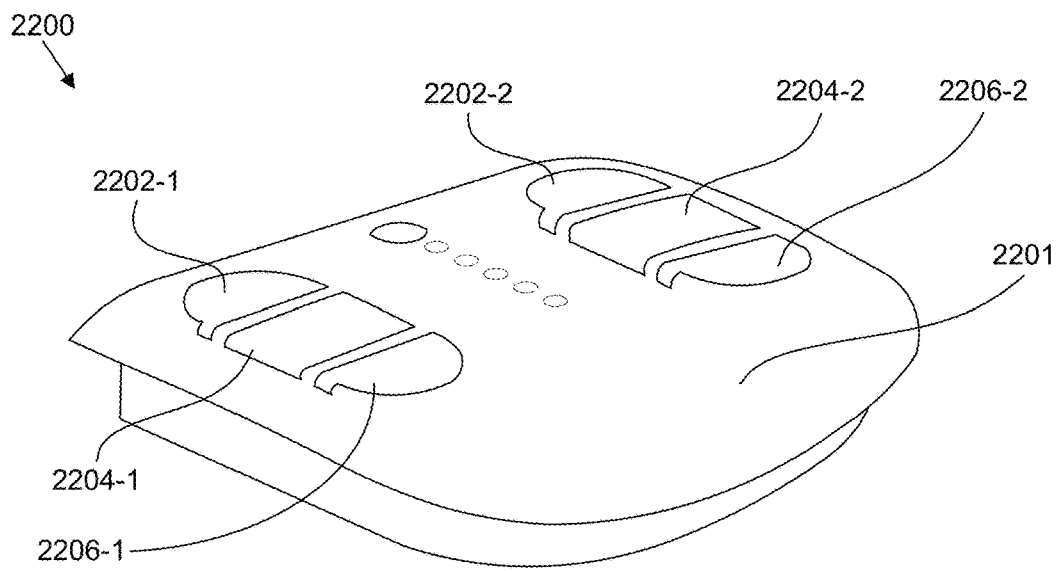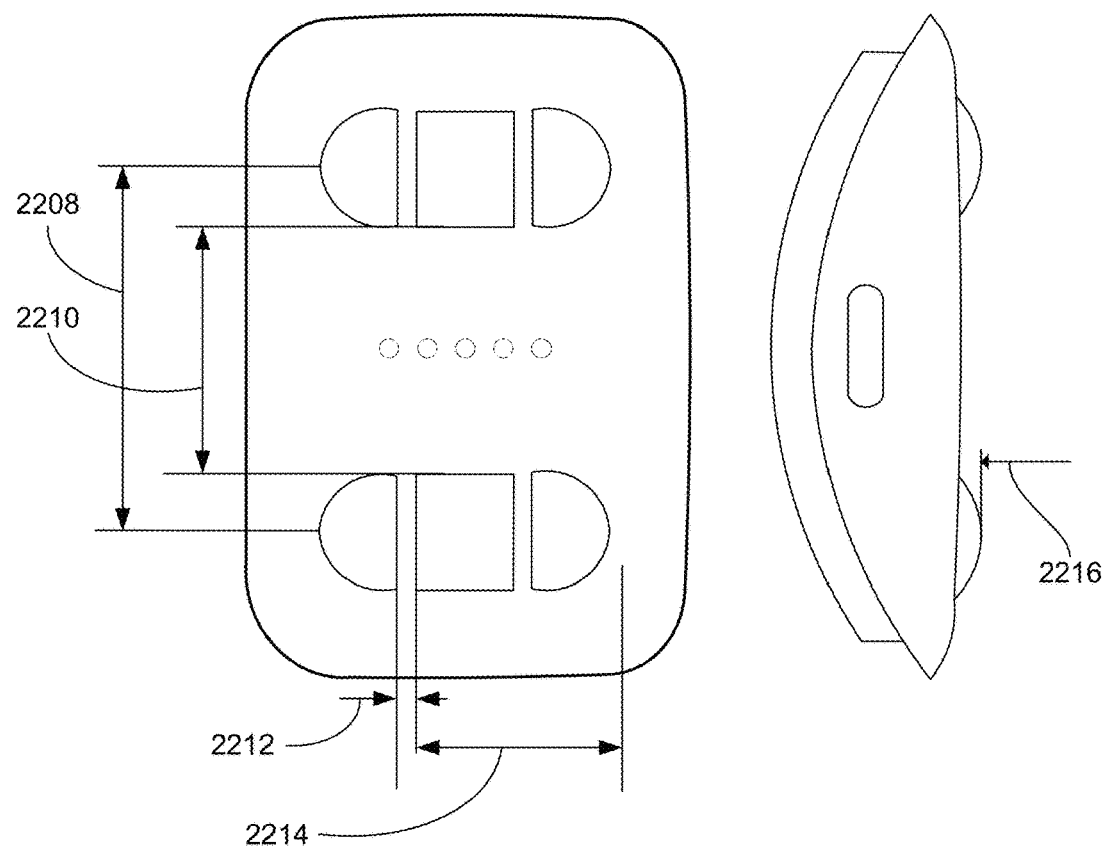
Figure 21

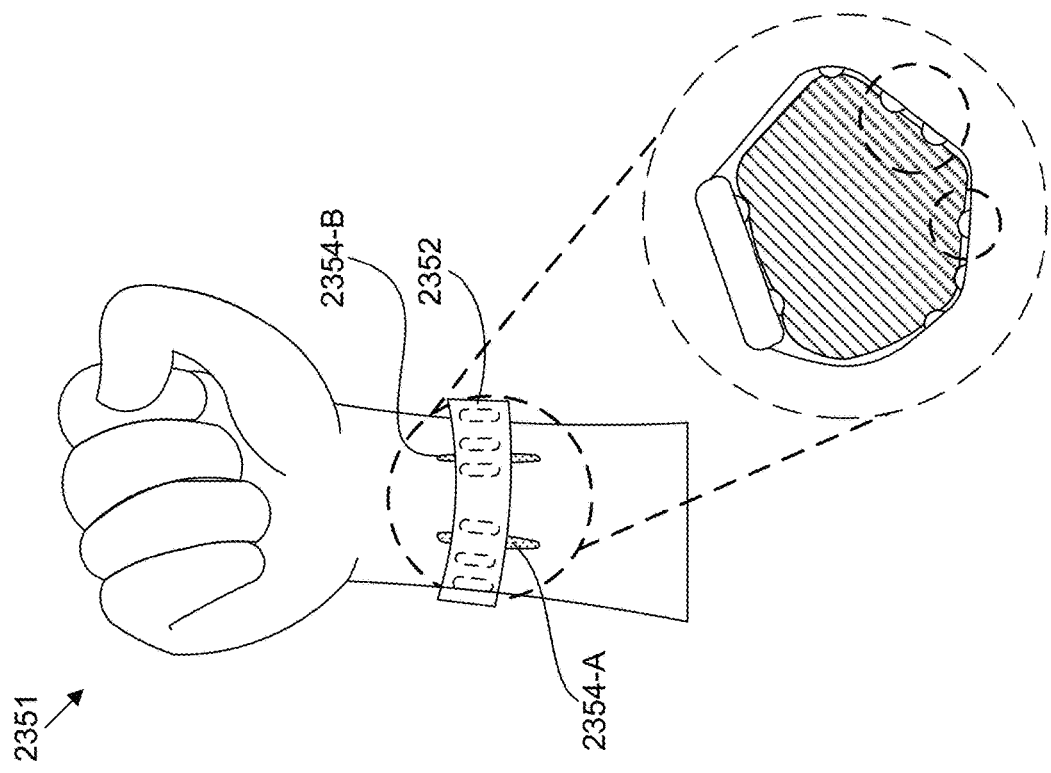
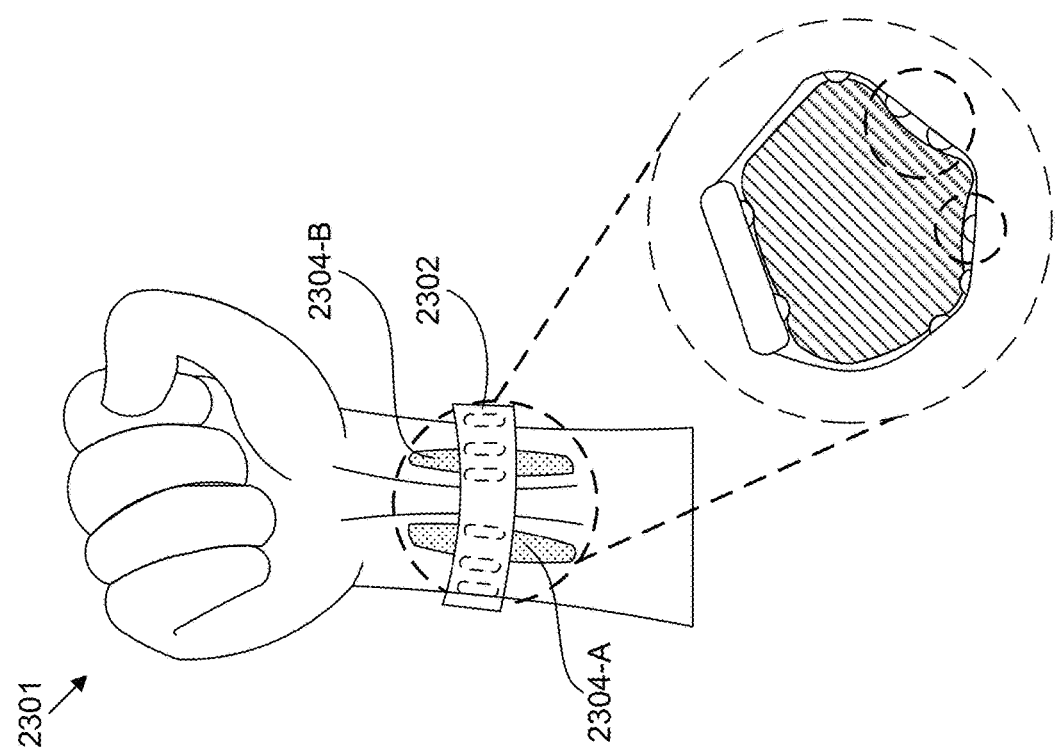
Figure 22

WEARABLE BAND STRUCTURE HAVING A BAND PORTION INCLUDING EMBEDDED STRUCTURAL MEMBERS WITH SIGNAL-PROCESSING COMPONENTS AND ANOTHER BAND PORTION NOT INCLUDING ANY ELECTRICAL COMPONENTS, AND SYSTEMS, DEVICES, AND METHODS OF MANUFACTURING THEREOF

RELATED APPLICATIONS

This application claims priority to U.S. Prov. App. No. 63/421,972, filed on Nov. 2, 2022, and entitled "Wearable Band Structure with an Integrated Flexible Circuit for Communicating Spatially-Distributed Sensor Signals to a Centralized Compute Core, and Systems and Methods of Assembly thereof"; U.S. Prov. App. No. 63/421,971, filed on Nov. 2, 2022, and entitled "Adjustable Band With a First Band Portion Having a Cinch Structure for an Adjustment Length of a Second Band Portion To Be Fed Therethrough, and Systems and Methods Thereof"; U.S. Prov. App. No. 63/421,970, filed on Nov. 2, 2022, and entitled "Elongated Neuromuscular-Signal Sensor Structure With Electrode Contact Points for Detecting Signals at Discrete Locations of a Wrist of a User, and Systems and Methods of Manufacturing Thereof"; U.S. Prov. App. No. 63/421,969, filed on Nov. 2, 2022, and entitled "Techniques for Housing a Compute Core Within a Textile Portion of a Wearable Band Structure That Includes Embedded Electronic Components for Communicating Detected Signals to the Compute Core, and Systems and Methods Thereof"; U.S. Prov. App. No. 63/580,346, filed on Sep. 1, 2023, and entitled "Method of Manufacturing a Covered Band Portion of an Adjustable, Form-Fitting Wearable Electronic Device with Biopotential-Signal-Sensing Structures and Associated Signal Processing Components, and Devices, Systems, and Methods of Use thereof"; and U.S. Prov. App. No. 63/594,892, filed on Oct. 31, 2023, and entitled "Compute Core Capsule Device for Processing Biopotential Signals Detected by a Wearable Device, including a Dual-Purpose Electrical Base Plate, and Methods of Manufacturing thereof," each of which is incorporated herein by reference.

TECHNICAL FIELD

The present disclosure relates generally to wearable electronic devices (e.g., wrist-worn wearable devices) and more specifically to wearable electronic devices having first band portions including components that detect and/or at least partially process biopotential signals of a user (e.g., neuromuscular signals, such as electromyography (EMG) signals detected at various positions of a wrist of a user), and second band portions that do not include any electronic components.

BACKGROUND

Some wearable electronic devices include signal-processing components for detecting signals of a body of the wearer (e.g., heart rate monitors). These devices, however, have shortcomings, namely with respect to comfort and ease of wear, which will be further described below. To meet specific sensing requirements of particular applications, some designs of wearable devices including such signal-processing components can be large and bulky, often including a large number of sensors to detect certain signals. The large and bulky wearable devices can be uncomfortable to users due to the size and weight of such wearable devices, which can also make the devices less practical and socially-acceptable for day-to-day use. Further, some current designs have inadequate form factors for providing a comfortable experience to a wearer while avoiding deleterious consequences to electronic components of the respective wearable electronic device. As such, it would be desirable to provide wearable electronic devices with user-friendly form factors, such as being less bulky, for sensing biopotential signals.

Further, functional considerations related to such wearable electronic devices can be complicated by design requirements for accommodating use with various different users having different body types, sizes, and/or compositions. For example, sensors of wearable electronic devices having electrodes or other electronic components that are specifically configured to contact a portion of a user's body may necessitate use of sensors having different heights, such that the respective sensing components can make sufficient electrical contact with users' skin to detect biopotential signals of the user (e.g., neuromuscular signals, such as electromyography (EMG) signals). As one example of such a constraint related to wrist-wearable devices, users having body mass indices (BMIs) that are within a particular range may be more susceptible to contact loss for electrodes that are configured to contact inner portions of those users' wrists, since tendons of such individuals may be more pronounced in this region of the users' wrist as a result of their lower BMIs.

SUMMARY

The wearable electronic devices and components thereof described herein address the deficiencies described above. The improved comfort in the design of the wearable bands and constituent components described herein has the added benefit of improving users' interactions with computing systems, including artificial-reality environments. For example, the embodiments described herein can improve users' adoption of artificial-reality environments, by providing form factors that are comfortable, socially acceptable, compact, and durable, withstanding wear and tear. The efficient form factors can allow users to wear the wearable bands throughout their daily lives. A few example embodiments that describe the advances of these wearable bands and their constituent components are detailed below.

In a first example, an adjustable band of a wearable electronic device (e.g., a wearable band) includes a first band portion having a first distal end, a second band portion having a second distal end, and a cinch structure coupled to the first distal end. The cinch structure defines an opening that extends beyond the first distal end in a direction substantially perpendicular to a longest dimension of the first band portion. The opening is configured to (i) have an adjustment length of the second band portion, including the second distal end, be fed therethrough, and (ii) cause the cinch structure to apply a frictional force adjacent to the adjustment length of the second band portion (e.g., while the adjustment length is being fed through, and after the adjustment length has been completely fed through the opening). After the adjustment length of the second band portion is fed through the opening defined by the cinch structure, an adjustable loop is formed having a first circumference sized to fit around a wrist of a user. The frictional force applied by the cinch structure is configured to be maintained adjacent to the adjustment length of the second band portion while the adjustable band is worn by the user such that the first circumference of the adjustable loop is also maintained.

The cinch mechanism allows users to more efficiently fasten and secure the wearable device to their wrist, which improves the donning and doffing user experience. The cinch mechanism is also further configured to not let the wearable device to loosen around an appendage (e.g., a wrist, ankle, etc.) of a user while being worn or performing activities.

In a second example, a band structure (e.g., a covered band) includes a first portion. The first portion of the band structure includes an embedded structural member (e.g., an internal band component) configured to hold one or more signal-processing components in respective fixed positions within the first portion of the band structure. The first portion of the band structure further includes the one or more signal-processing components (e.g., biopotential-signal-sensing components, including carrier components (e.g., receiving structures)), which are coupled to the embedded structural member, and the one or more signal-processing components are configured to at least partially process biopotential signals of the wearer of the band structure (e.g., neuromuscular signals, such as EMG signals, corresponding to performances of user actions and/or physical activities). The band structure further includes a second portion that does not include any electrical components. The first portion of the band structure and the second portion of the band structure are each configured to couple directly to one another to form a loop and the loop is sized to accommodate a wrist of the user (e.g., the wearer).

In a third example, a biopotential-signal sensor structure includes a carrier component (e.g., a receiving structure), an analog front end (AFE), and one or more attachment mechanisms (e.g., mounting pins). The carrier component is configured to hold two biopotential-signal-sensing contact points (e.g., EMG electrodes) that are configured to be in contact with the skin of a user. The carrier component electrically separates the two biopotential-signal-sensing contact points from one another. The carrier component and the biopotential-signal-sensing contact points combine to produce a seamless structure that is configured to allow multiple sensors to be placed on a wearable device. Each of the two biopotential-signal-sensing contact points extends above a wrist-facing surface of the wearable device, such that when the wearable device is worn, each of the two biopotential-signal-sensing contact points is at a predetermined skin depression depth. The AFE is coupled to the two biopotential-signal-sensing contact points for processing a component of a received signal from the two biopotential-signal-sensing contact points. The one or more attachment mechanisms are configured to secure the seamless structure to the wearable device.

In a fourth example, a textile-based material has a geometrically shaped opening that defines a compute-core region. The compute-core region is configured to seamlessly surround a perimeter of a compute core of a wearable electronic device, the compute core being configured to process electrical signals of the wearable electronic device. The geometrically shaped opening includes a portion of textile material that is angled relative to a first adjacent portion of the geometrically shaped opening to allow for coupling the geometrically shaped opening with a connection point of the compute core.

In a fifth example, a method of manufacturing a wearable band is provided. The method includes providing an internal band component that includes a plurality of sensor-holding structures coupled with the internal band component (e.g., an embedded structural member). The method further includes sheathing the internal band component with a tubular textile band cover, such that the tubular textile band cover substantially surrounds each respective sensor-holding structure of the plurality of sensor-holding structures, thereby producing a covered band portion of the wearable band. The method further includes providing a plurality of sensing components configured to be coupled to respective sensor-holding structures of the plurality of sensor-holding structures. The method further includes cutting, via a first laser-cutting operation, sensor-placement openings at respective sensor locations of the covered band portion (e.g., corresponding to respective mounting pins of receiving structures coupled to the internal band component), each respective sensor location corresponding to a respective sensor-holding structure of the plurality of sensor-holding structures. And the method further includes coupling the plurality of sensing components to the respective sensor-holding structures of the plurality of sensor-holding structures, while the sensor-holding structures are located at the respective sensor locations.

In a sixth example, a wearable electronic device is provided. The wearable electronic device includes a compute core. The compute core includes a skin contact surface and defines a cavity. The cavity is at least partially configured to house a battery, an electrode assembly located at the skin contact surface, an analog front end associated with the electrode assembly, a main logic board, and a metallic baseplate. The electrode assembly is configured to sense neuromuscular signals. The analog front end is configured to partially process the sensed neuromuscular signals into partially processed neuromuscular signals. The main logic board is configured to receive the partially processed neuromuscular signals, and determine gestures based on the partially processed neuromuscular signals. The metallic base plate is configured to provide an electrical ground for the electrode assembly, and electrically shield the electrode assembly from electrical and magnetic noise. At least some of the electrical and magnetic noise is from at least one of the main logic board and the battery. And the analog front end is placed on a first side of the metallic base plate and the main logic board is placed on a second side that is opposite to the first side of the metallic base plate.

In some embodiments of the present disclosure, electrodes of wearable electronic devices are configured with particular electrode dimensions, which are determined based on physical aspects of wearers of such electronic devices. For example, protrusion depths of one or more sets of electrodes disposed along a band portion of a wearable electronic device may be sized and/or arranged based on bodily aspects of the respective wearer of the electronic device. Such customizations in sizes may be based on the sensitivity required for particular use cases. For example, a first set of operations may be made available using a particular set of stock keeping units (SKUs), where each SKU is associated with a range of BMIs (e.g., a first SKU for users with less than 20 BMI, a second SKU for users with a BMI of between 20 and 25, and a third SKU for users with BMIs of greater than 25).

The features and advantages described herein are not necessarily all-inclusive. Some additional features will be apparent to one of ordinary skill in the art in view of the drawings, specification, and claims provided in this disclosure. At times, language used in the specification has been intentionally selected for readability and/or to convey a specific aspect of the subject matter, and not necessarily to delineate or circumscribe the subject matter.

BRIEF DESCRIPTION OF THE DRAWINGS

So that the present disclosure can be understood in greater detail, a more particular description can be had by reference to the features of various embodiments, some of which are illustrated in the appended drawings.

FIG. 5 illustrate an example method for machining an example biopotential-signal sensor structure, in accordance with some embodiments.

FIGS. 17A-17F show an example method of manufacturing a wearable band that includes a tubular textile band cover surrounding an internal component, in accordance with some embodiments.

FIG. 21 shows aspects of a skin-contacting surface of a compute core for a wearable electronic device, in accordance with some embodiments.

FIG. 22 shows examples of different wrist-wearable devices having different relative dimensions based on physical aspects of respective wearers of the different wrist-wearable devices, in accordance with some embodiments.

In accordance with common practice, the various features illustrated in the drawings are not necessarily drawn to scale, and like reference numerals can be used to denote like features throughout the specification and figures.

DETAILED DESCRIPTION

Numerous details are described herein, to provide a thorough understanding of the example embodiments illustrated in the accompanying drawings. However, some embodiments can be practiced without many of the specific details, and the scope of the claims is only limited by those features and aspects specifically recited in the claims. Furthermore, well-known processes, components, and materials have not necessarily been described in exhaustive detail, to avoid obscuring pertinent aspects of the embodiments described herein.

Figure 1A:
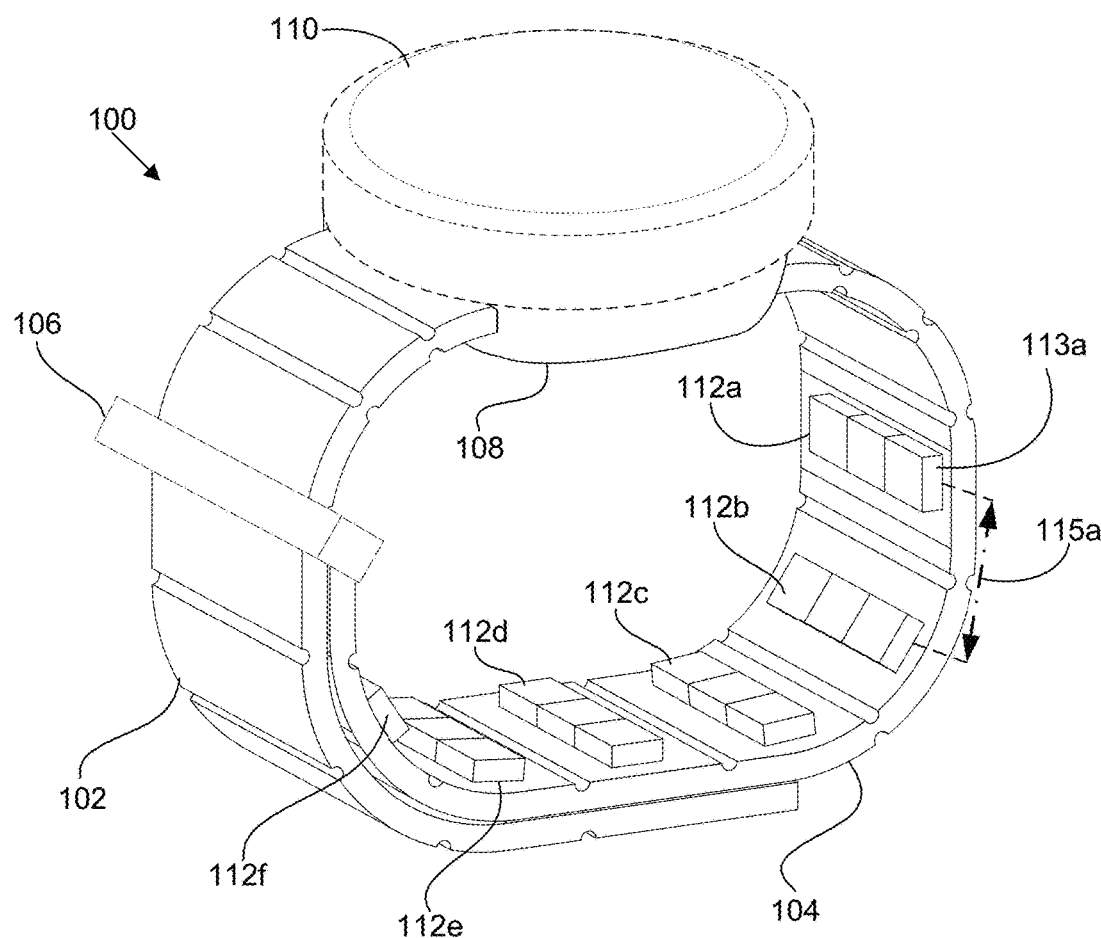
FIGS. 1A-1C illustrate an example wearable electronic device for sensing biopotential signals of a user, in accordance with some embodiments.
Figure 1B:
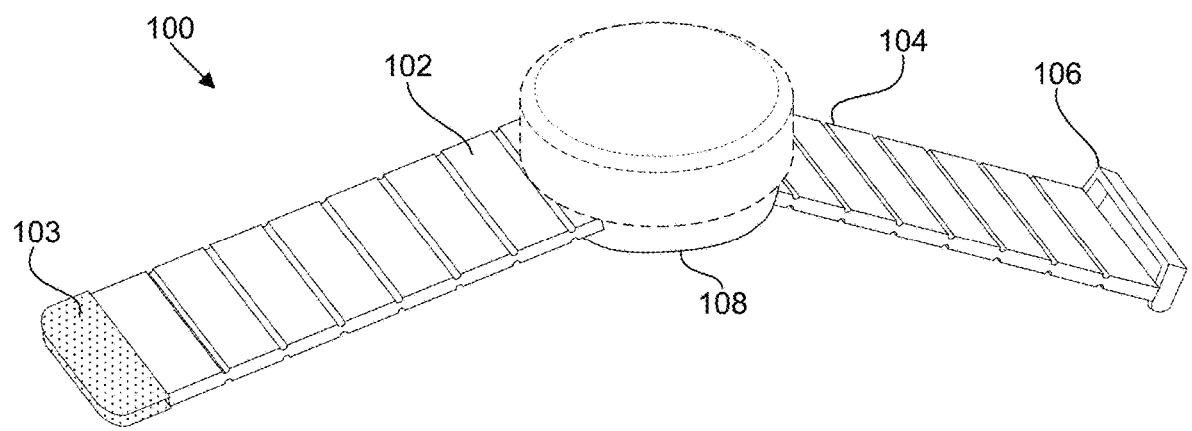
Figure 1C:
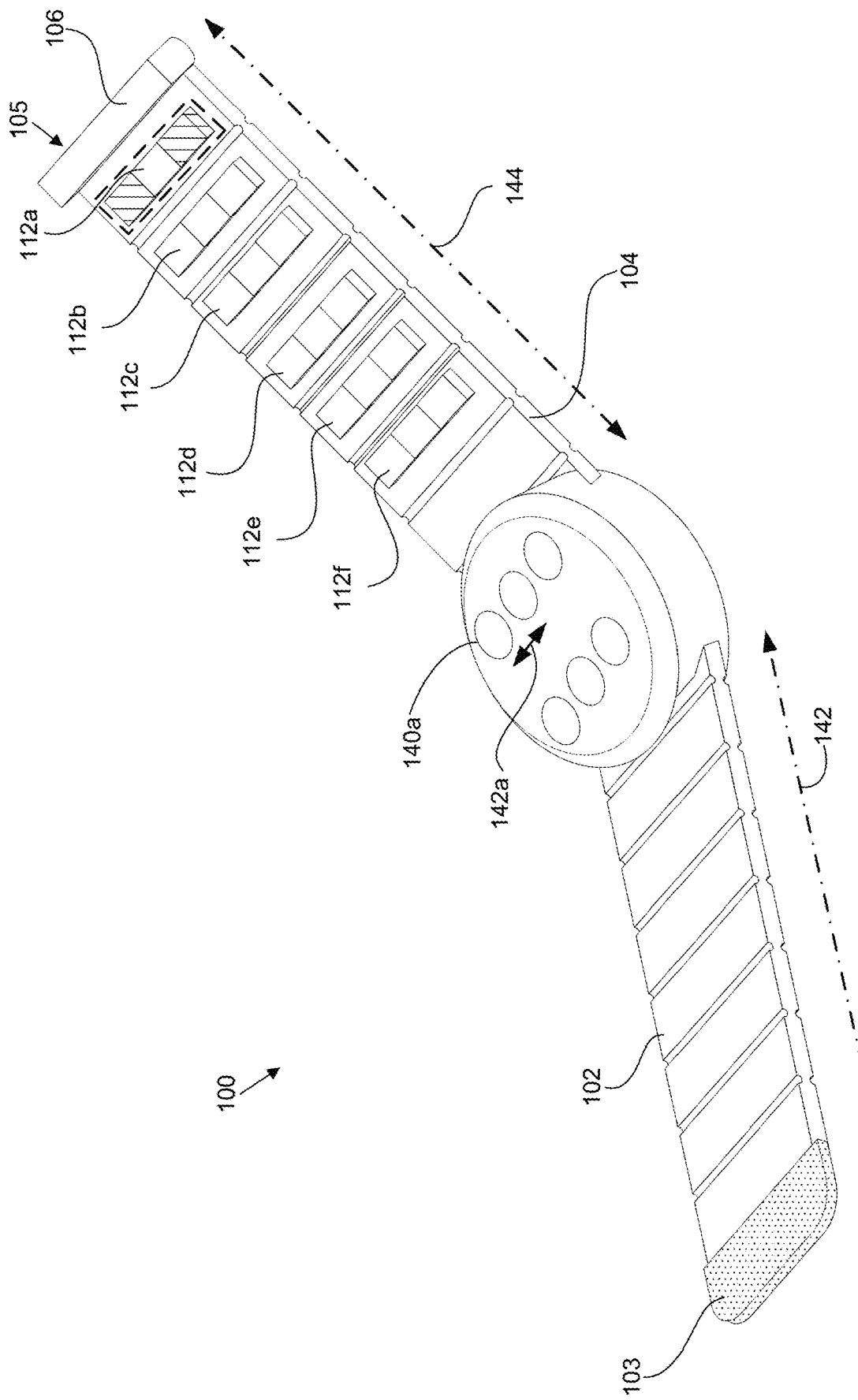

FIGS. 1A-1C illustrate an example of a wearable electronic device 100 (which may be described herein as a wrist-wearable device) that is configured to sense biopotential signals of a user, in accordance with some embodiments. The wearable electronic device 100 is a band-shaped electronic device (e.g., a smart watch, a band) that can be configured to be worn on a wrist of a user (e.g., a wearer). In some embodiments, the wearable electronic device includes a display 110, which may be configured to display user interfaces related to the biopotential signals of the wearer. In some embodiments, the wearable electronic device 100 does not include the display 110. In some embodiments, the display 110 is detachable from the wearable electronic device 100 (e.g., as an accessory item). In some embodiments, other accessory items can be removably detached from the wearable electronic device 100 (e.g., additional and/or upgraded sensing components, haptic devices).

FIG. 1A illustrates a perspective view of the wearable electronic device 100. The wearable electronic device 100 has a band portion 102, a band portion 104, a cinch structure 106, a compute core 108, an optional display 110, and a plurality of biopotential-signal sensing structures 112*a*-112*f* distributed along a length of the band portion 104. In some embodiments, the band portion 102 and the band portion 104 are separated by a compute core 108. The band portion 102 and the band portion 104 are secured via the cinch structure 106 to form an adjustable loop that has a circumference, which can be sized to fit around a user's wrist. In some embodiments, one or both of the band portions 102 and 104 can be made of elastic or partially elastic materials that can stretch to accommodate different wrist sizes of wearers of the wearable electronic device 100.

As discussed below with respect to FIG. 18, different band portions and sub-portions of band portions can have different amounts of elasticity. For example, the band portion 104 may have a first sub-portion having biopotential-signal-sensing components configured to detect portions of wearers' wrists associated with higher levels of biopotential activity, and a second sub-portion having biopotential-signal-sensing components configured to detect portions of the wearers' wrists associated with lower levels of biopotential activity. And the first sub-portion may be comprised of a substantially rigid material such that a fixed spacing is maintained between the biopotential-signal-sensing components of the first sub-portion. And the second sub-portion can be comprised of an elastic or partially elastic material that is configured to stretch to accommodate varying wrist sizes of wearers of the wearable electronic device 100.

FIG. 1B illustrates a perspective top view of the wearable electronic device 100, where the wearable electronic device 100 is unstrapped (e.g., doffed, that is, removed from the wrist of the user). That is, the band portion 102 and the band portion 104 are shown uncoupled and extending outward in substantially opposite directions. The first band portion 102 has a distal end 103 that is made of a different material and/or has a different geometry than a separate part of the length of the first band portion, such that it is configured to be fed through an opening defined by the cinch structure 106. The distal end 103 is made of a different material than the rest of the length of the band portion 102 (e.g., an elastomer material). The elastomer material can be stiffer than the rest of the band portion 102, which can make the distal end 103 easier to feed the distal end 103 through an opening of the cinch structure 106 without bending or otherwise causing deformation of the distal end 103 while it is fed through the cinch structure 106.

FIG. 1C illustrates a perspective bottom view of the wearable electronic device 100. In addition to the biopotential-signal sensing structures 112a-112f distributed across the band portion 104, the wearable electronic device 100 includes a plurality of sensing components (e.g., an EMG electrode 140a) on a bottom surface of the compute core 108. In some embodiments one or more of the sensing components on the bottom surface of the wearable electronic device 108 are also biopotential-signal-sensing components (EMG-sensing electrodes). In some embodiments, there is a minimum separation distance 142a between each contact point on the bottom surface of the compute core 108. In some embodiments, the contact points are proud, that is, they protrude slightly from a lower surface of the compute core 108 and/or a covered band portion surrounding the compute core 108.

The band portion 102 and the band portion 104 can have respective lengths 142 and 144, which can be sized from 75-175 millimeters, respectively (e.g., SKUs associated with particular ranges of wearers' wrist sizes). In some embodiments, the respective lengths of each of the band structures can be distinct, but still sum to a total length of between 150-350 millimeters based on the respective stock keeping unit (e.g., small, medium large) of the wearable electronic device that includes the band portion 102 (e.g., the first band portion) and the band portion 104 (e.g., the second band portion).

FIGS. 2A-2E illustrate example cinch structures (e.g., a cinch structure 200, a cinch structure 220, and a cinch structure 250), each of which can be used to affix an example wearable electronic device to a user, in accordance with some embodiments. In some embodiments, other closure structures (e.g., D-ring closures, such as the D-ring closure 1808 shown in FIG. 18) may be used in addition or alternatively to the cinch closure embodiments described with respect to FIGS. 2A-2E.

Figure 2B:
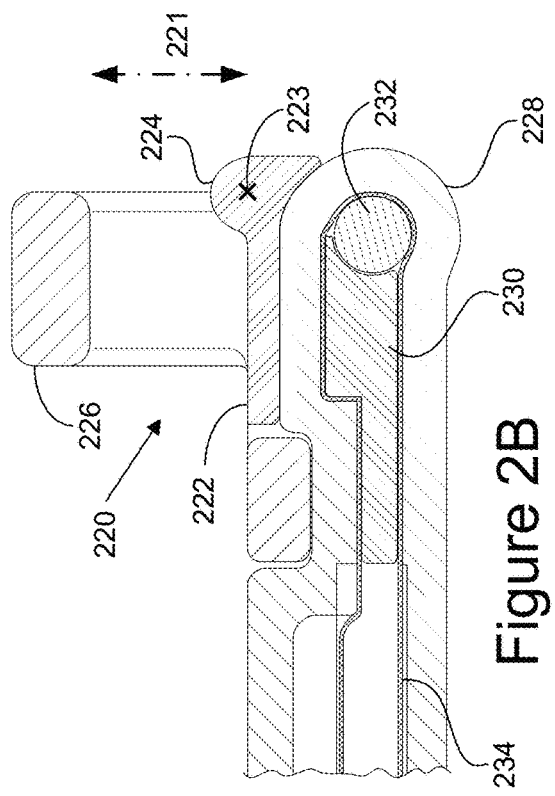
FIGS. 2A-2E illustrate an example cinch structure, which can be used to affix an example wearable electronic device to a user, in accordance with some embodiments.
Figure 2C:
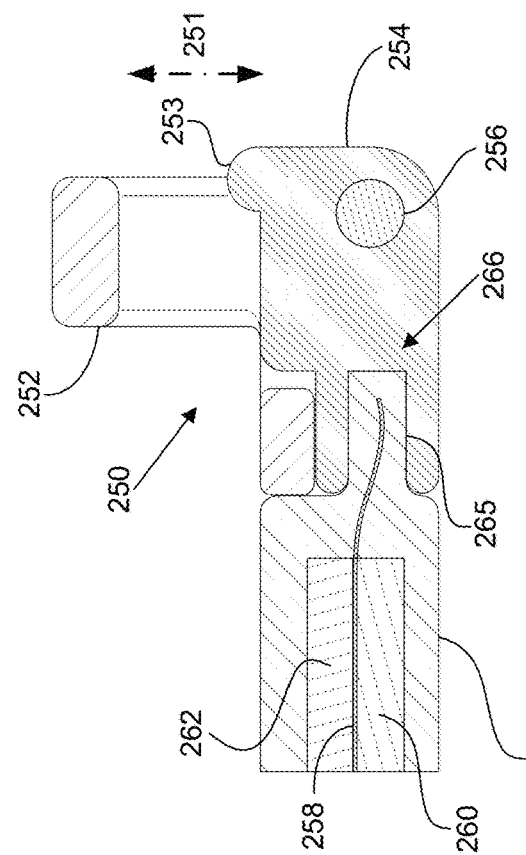
Figure 2A:
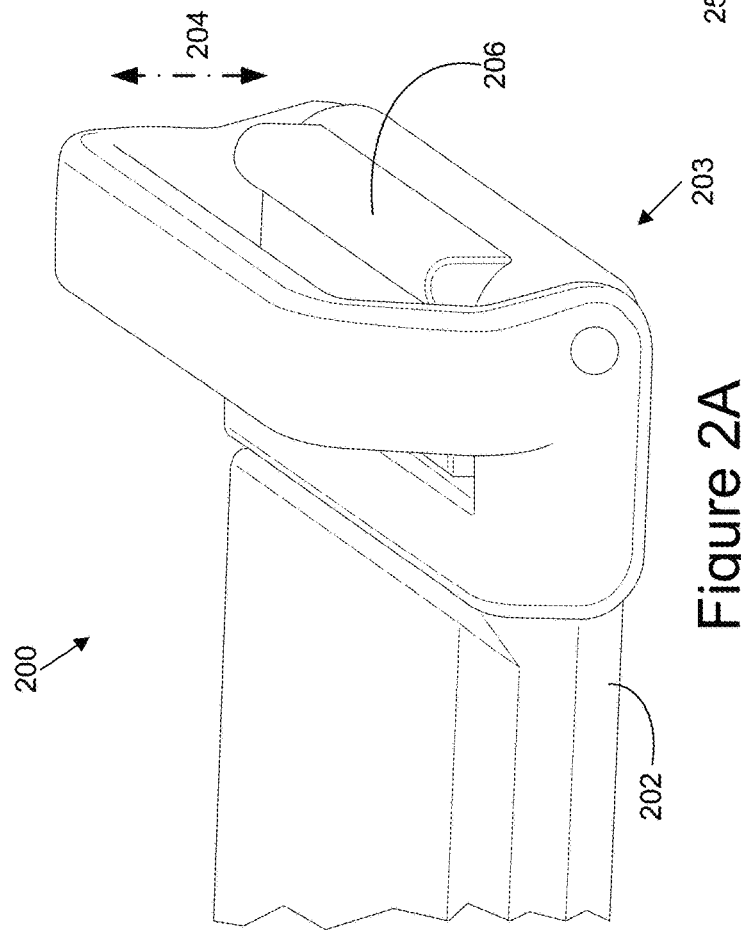

FIG. 2A shows a perspective view of a cinch structure 200 attached to a distal end 203 of a first band portion 202. The cinch structure 200 is coupled to a distal end of the first band portion 202 and is configured for another distal end of a second band portion (e.g., the distal end 103, which is coupled with the second band portion 104 of the wearable electronic device 100 in FIGS. 1A-1C) to be fed through an opening 204 of the cinch structure 200. Feeding the distal end 103 of the second band portion 102 through the opening 204 allows for the user to fasten, secure, and/or tighten the wearable device around their wrist, and as will be discussed below, the cinch structure 200 is also configured to stop the second band portion from moving after it has been adjusted to its desired tightness. The cinch structure 200 defines an opening 204 that is configured to receive at least a portion of an adjustment length of the second band portion. The opening 204 extends beyond the distal end 203 in a direction that is substantially perpendicular (e.g., vertical, orthogonal to a lengthwise direction of the band portion) to a direction of the longest dimension of the first band portion 202 (e.g., lengthwise, horizontal). That is, the opening 204 of the cinch structure 200 is not just an extension of the first distal end 203, according to some embodiments. The cinch structure 200 may be a separate structure from the band portion that includes the first distal end 203. The cinch structure 200 may be detachably or permanently coupled to the distal end 203, and may extend vertically beyond (e.g., protruding above with respect to a skin contact surface of an inner portion of the band) the first distal end 203 of the cinch structure 200 also includes a protrusion 206 adjacent to the opening 204. The opening 204 is configured to receive a second band portion, and the second band portion includes another distal end (e.g., the distal end 103 of the second band portion 102 in FIGS. 1A-1C). In some embodiments, when the second band portion is fed through the cinch structure 200, the cinch structure 200 and/or a component associated therewith is caused to apply a frictional force adjacent to the second band portion to keep the second band portion in place. The protrusion, as will be discussed later, secures the second band portion from unintentionally loosening the wearable electronic device around a user.

FIG. 2B shows a cross-sectional side view of a first example cinch structure 220, which includes a compression plate 222. FIG. 2B illustrates that a top surface of the compression plate 222 can be flush with a top surface of a band portion 228. The compression plate 222 includes a protrusion 224 (i.e., protrusion 206 in FIG. 2A) that extends upward from the flush surface of the compression plate 222 into the opening 204. In some embodiments, a top surface of the protrusion 224 is configured to protrude above the flush surface by at least 0.5 millimeters. In some embodiments, the compression plate 222 is made of machined 6061 stainless steel. The protrusion 224 is configured to further secure the second band portion at a particular circumference (e.g., by increasing the friction force) allowing for the user selected tightness level to be maintained while the wrist wearable device is worn. In accordance with some embodiments, the protrusion 224 is configured such that it does not cause additional friction while the cinch structure 220 is in a first configuration (e.g., while a cinch loop 226, described in more detail below, is rotated such that it is parallel with a major dimension of the band portion 228. And the protrusion 224 is also configured to provide additional friction force while the cinch structure 220 is in a second configuration, as illustrated by FIG. 2B.

The cinch structure 220 also includes a cinch loop 226 that is configured to couple with the compression plate 222 via a shoulderless spring bar 232, in accordance with some embodiments. The shoulderless spring bar 232 is coupled with an interior loop mount 230 that is substantially embedded within the band portion 228. The cinch loop 226 of the cinch structure 220 can define an opening 221 (e.g., an opening having the same dimensions as the opening 204 in FIG. 2A) between a top inner surface of the cinch loop 226 and a flush section of the compression plate 222 (e.g., that is flush with a top surface of the band portion 228). In some embodiments, the opening 221 is between two millimeters and four millimeters wide. In some embodiments, the cinch structure 220 includes the interior loop mount 230 that is embedded in the band portion 228, which is used as a mounting point for the compression plate 222. In some embodiments, a polymer material 234 encases the interior loop mount 230 and the shoulderless spring bar 232 to partially secure the shoulderless spring bar 232 to the interior loop mount 230. In some embodiments, the polymer material is constructed of a spun polymer fiber (e.g., Vectran). The spun polymer fiber can be configured to maintain a fixed position of the interior loop mount 230 and/or the cinch structure 220.

FIG. 2C shows a cross-sectional side view of a second type of cinch structure 250 that includes a lower cinch-coupling piece 254 that is configured to couple with a tapered portion of the band portion 264 (e.g., within a pocket 265 of the cinch coupling piece 254). That is, FIG. 2C shows a second type of cinch structure, different than the cinch structure 220 shown in FIG. 2B, where the lower cinch-coupling piece 254 is a single component, whereas FIG. 2B shows this component being made of two pieces screwed together (e.g., interior loop mount 230 and compression plate 222). FIG. 2C shows that the lower cinch-coupling piece 254 includes a protrusion 253 that extends into an opening 251 that is defined by a cinch loop 252. The lower cinch-coupling piece 254 is coupled with a distal end 266 of a band portion 264. The lower cinch-coupling piece 254 is coupled with the cinch loop 252 via a shoulderless spring bar 256 that is embedded within the lower cinch-coupling piece 254. The lower cinch-coupling piece 254 includes a pocket 265 (e.g., a keeper) that is configured to receive a tapered portion (or a portion with a shorter height) of a distal end of the band portion 264. The band portion 264 includes an interior that has a top layer 262 and a bottom layer 260, which can include elastomeric material, in accordance with some embodiments. In some embodiments, an adhesive is applied to the tapered portion 265 of the distal end 266, such that the tapered portion can be securely coupled with the lower cinch-coupling piece 254. A polymer material 258 extends between the top layer 262 and the bottom layer 260 and into the tapered portion 265 of the distal end 266. In some embodiments, the polymer material 258 is made of one or more of the same materials as the polymer material 234 shown in FIG. 2B. The polymer materials 234 and 258 can be configured to reduce and/or prevent elongation stress of the respective band portions 228 and 264.

Figure 2D:
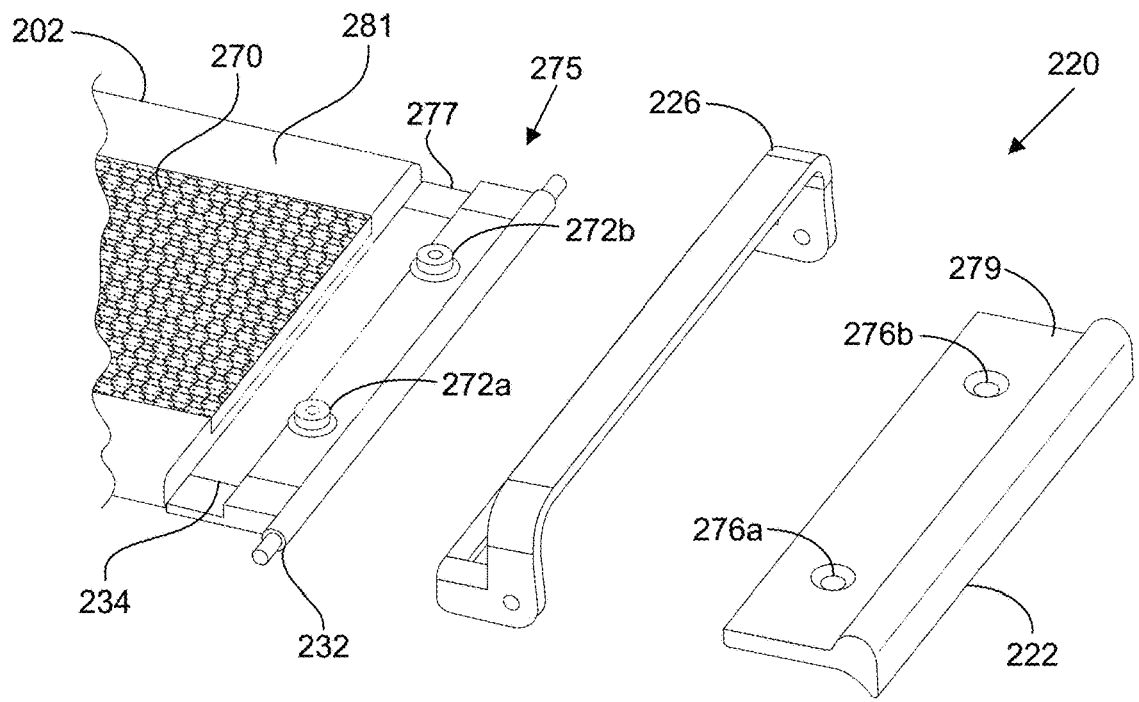

FIG. 2D shows an exploded view of the first example cinch structure 220 shown in FIG. 2B. The first band portion 202 includes a magnetic chain component 270 that extends along the longest dimension of the first band portion 202, in accordance with some embodiments. The magnetic chain component 270 can be configured to couple with one or more magnets and/or metal components of a second band portion (e.g., the second band portion 104 in FIGS. 1A-1C) that can be fed through the cinch structure 220. A distal end 275 is configured (e.g., shaped) to receive the cinch loop 226 and the compression plate 222 of the cinch structure 220. The distal end 275 defines an inset 277 that is configured to receive a lower surface of the cinch loop 226 of the cinch structure 220. In some embodiments, when the lower surface of the cinch loop 226 is placed in the inset 277, a top surface 279 of the cinch loop 226 is configured to be flush with a top surface 281 of the first band portion 202. The distal end 275 also includes attachment pins 272a and 272b. The attachment pins 272a and 272b are configured to couple with respective attachment holes 276a and 276b defined by the compression plate 222 of the cinch structure 220. In some embodiments, the attachment pins are bolts or self-tapping screws that are screwed into holes 276a and 276b.

Figure 2E:
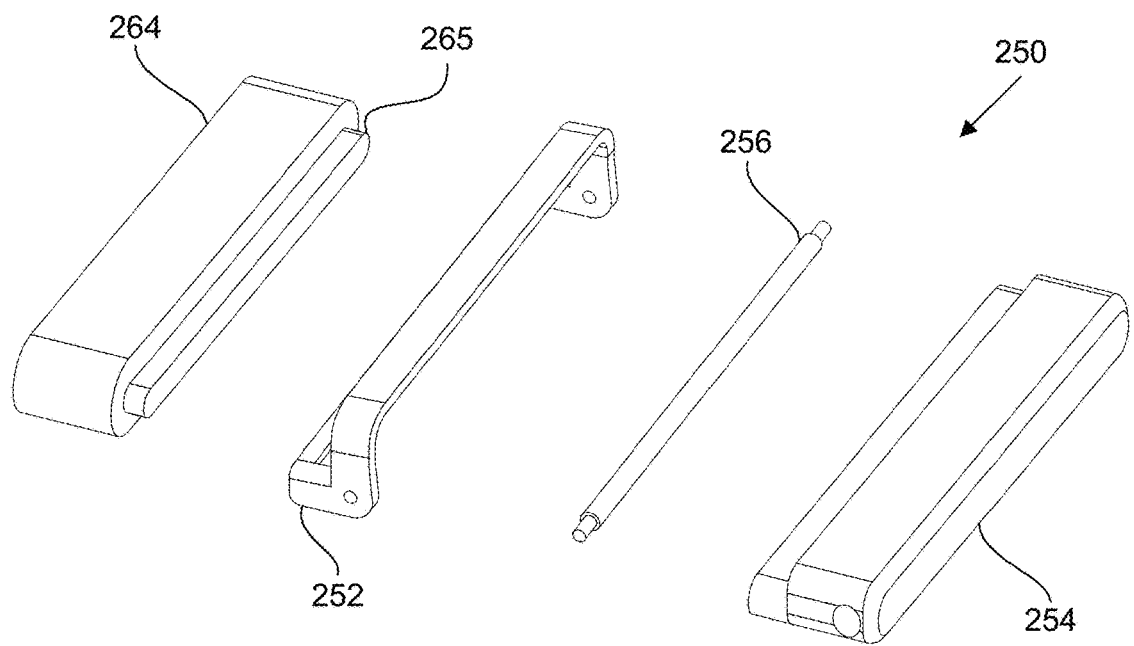

FIG. 2E shows an exploded view of the second example cinch structure 250, which is shown in FIG. 2C. In this second example cinch structure, the shoulderless spring bar 256 can be configured to couple directly with the lower cinch-coupling piece 254. The shoulderless spring bar 256 is then coupled with the cinch loop 252 to keep the lower cinch-coupling piece 254 with the cinch loop 252 in order to produce a combined cinch structure. The combined cinch structure can be coupled with the tapered portion 265 of the distal end 266.

Figure 3A:
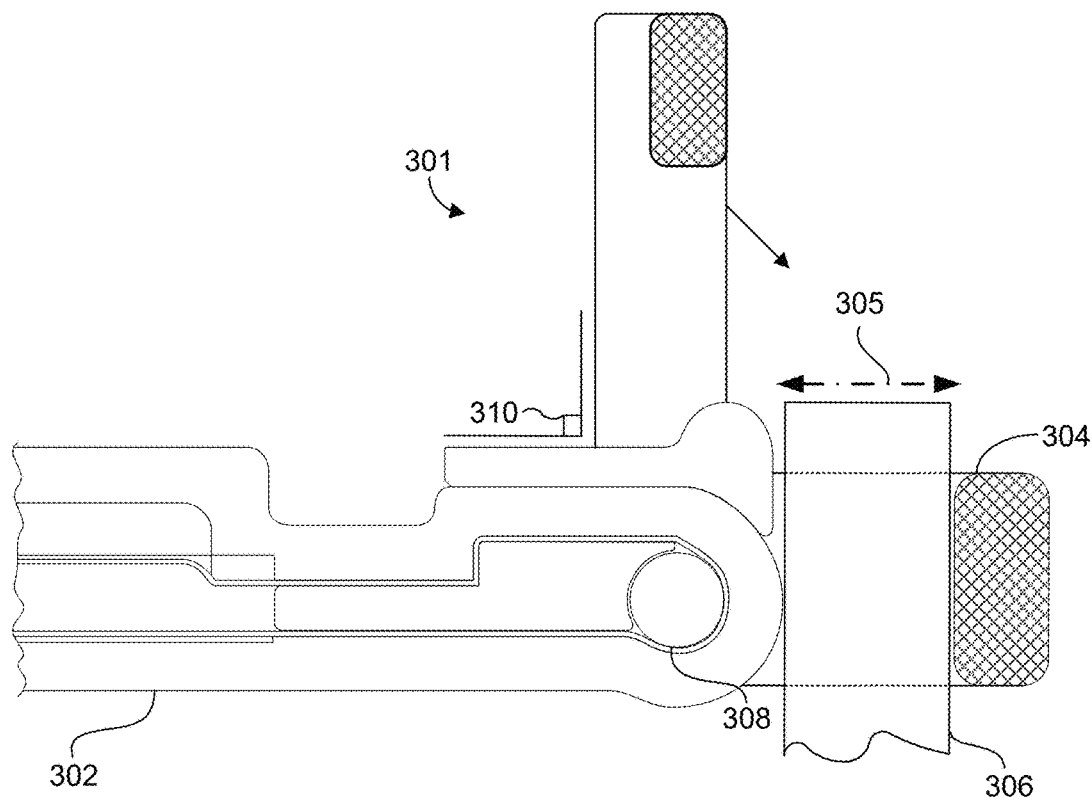
FIGS. 3A-3B illustrate an example coupling sequence for affixing an example wearable electronic device to a user, in accordance with some embodiments.
Figure 3B:
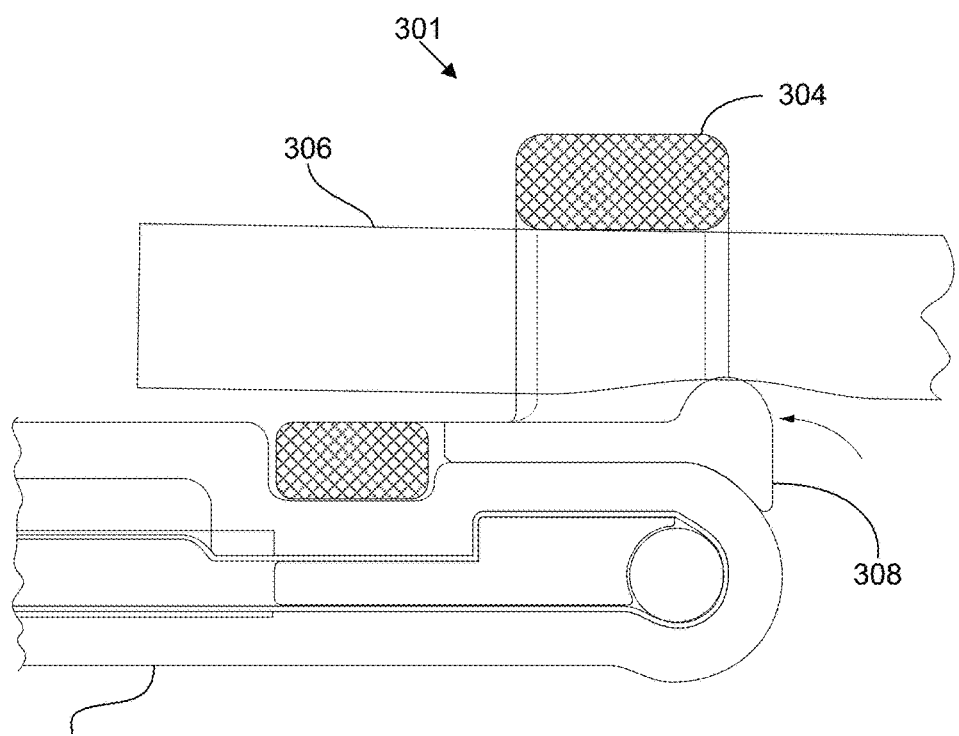

FIGS. 3A-3B illustrate a cross-sectional view of an example coupling sequence for affixing an example wearable electronic device to a user, in accordance with some embodiments. The wearable electronic device can include some or all of the components of the wearable electronic device 100 in FIGS. 1A-1C and 2A-2E. In some embodiments, the cinch loop 304 of the cinch structure 301 is configured to rotate (e.g., pivot) about the shoulderless spring bar 308 of the cinch structure 301. By such rotation of the cinch loop 304, the amount of force applied to the second band portion by the cinch structure 301 as the second band portion is fed through is reduced. In some embodiments, at least part of the reduction in force can be based on reducing the surface area of the frictional surface modifier that is in contact with the adjustment length. In some embodiments, at least part of the reduction in force can be based on minimizing how far the protrusion extends into the opening 305 defined by the cinch loop 304.

FIG. 3A also shows a first band portion 302 that includes the cinch structure 301. The cinch loop 304 of the cinch structure 301 is positioned in a first configuration (e.g., rotated at an angle 310 (e.g., a 90-degree angle) with respect to a closed position (e.g., a 0-degree angle) of a second configuration of the cinch loop 304. FIG. 3A also shows that the second band portion 306 is fed through the opening 305 that is defined by the cinch loop 304 with a reduced amount of force while the cinch loop 304 is in the first configuration at the 90-degree angle with respect to the closed position. For example, a first frictional force can be applied by the cinch structure 301 (e.g., based on a surface material of a top surface of the interior loop mount 308 and/or a surface of the cinch loop 304) when the second band portion is fed through the opening while the cinch loop 304 is in the flush position. A second force, less than the first force, can be applied by the cinch structure 301 when the second band portion is fed through the opening 305 while the cinch loop 304 is rotated at the angle 310 with respect to the flush position.

In some embodiments, the second frictional force is at least 0.3 Newtons less than the first frictional force that is caused to be applied to the respective band portion that is fed through the cinch structure 301. In some embodiments, the second frictional force is less than the first frictional force, at least in part, based on a reduced surface area of a frictional modifier on one or more surfaces of the cinch structure 301 that is in contact with the second band portion as the adjustment length is fed through the opening 305 defined by the cinch loop 304.

In some embodiments, the cinch structure 301 includes a bistable locking mechanism, which may be configured to secure the cinch loop 304 in each of the first and second configurations (based on the cinch loop being rotated within a particular angular range of being in the first and/or second configurations). The bistable locking mechanism can have a first equilibrium state in the flush position, and a second equilibrium state at a full rotation angle of the cinch loop 304 (e.g., at or beyond the angle 310). In some embodiments, while the cinch loop 304 is rotated away from the flush position, a reverse rotation force can be applied (e.g., by a spring in physical communication with the cinch loop 304) to the cinch loop 304, where the reverse locking force is configured to rotate the cinch loop 304 back to the flush position. That is, in some embodiments, while the cinch loop 304 is arranged in the first configuration, a force is applied to the cinch loop 304 to cause it to return to the second configuration (e.g., the closed position).

FIG. 3B shows the cinch structure 301 after the adjustment length of the second band portion has been fed through cinch loop 304 and the cinch loop 304 has rotated back to the closed flush position. In some embodiments, the second frictional force, greater than the first frictional force, is applied to the second band portion 306, after the cinch loop 304 has been rotated back to the flush position. For example, a greater amount of normal force can be applied by the protrusion of the interior loop mount 308 while the cinch loop is in the closed flush position, since the protrusion extends further into the opening 305 defined by the cinch loop 304 when in the closed flush position. Additionally, as discussed above with respect to FIG. 3A, the cinch structure 301 can also include frictional modifiers to further secure the second band portion 306 at a particular circumference of a wrist of a wearer.

FIGS. 4A-4E illustrate an example compute core 402 that can be used in conjunction with an example wearable electronic device, in accordance with some embodiments. As will be discussed in greater detail below, the compute core 402 can receive partially processed neuromuscular signals from AFEs distributed along an FPC (e.g., an internal band component). In some embodiments, the compute core 402 performs additional computing functions, including additional sensing proud electrodes disposed on a lower surface of the compute core 402. In some embodiments, the compute core 402 performs computing functions for causing an LED light to be displayed (e.g., from an upper surface of the compute core 402), which may be used to indication a detection state of biopotential-signal sensing components of the wearable electronic device 400. For example, a first LED signal may indicate that one or more of the biopotential-signal-sensing components of the wearable electronic device 400 are not forming sufficient contacts with skin of the wearer for proper biopotential-signal sensing to occur.

Figure 4A:
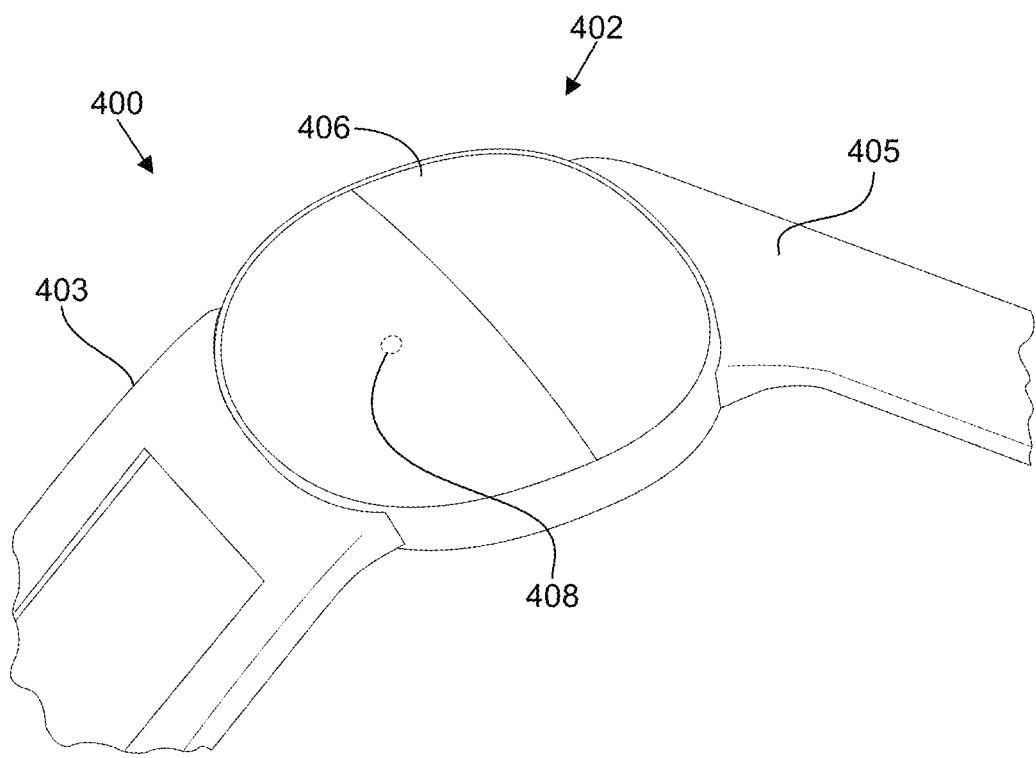
FIGS. 4A-4E illustrate an example compute core that can be used in conjunction with an example wearable electronic device, in accordance with some embodiments.

FIG. 4A shows a perspective view of a wearable electronic device 400 that includes an example compute core 402. In some embodiments, the compute core 402 can be connected to a single unitary band structure, according to some embodiments. In some embodiments, the compute core 402 can separate two band portions 403 and 405. The compute core 402 has a bottom case 404, which is configured to be coupled with a top case 406 in order to form a single unitary structure. In some embodiments, the unitary structure has flush edges.

The top case 406 defines an opening for displaying a light-emitting diode (LED) (LED opening 408), which can be configured to allow light from an LED to be pass through a top surface of the top case 406. In some embodiments, the top case 406 is made of polycarbonate (e.g., Makrolon 2405 MAS048). In some embodiments, the top case 406 is made of a different material than the bottom case 40, which may be based on a desired form factor of the wearable electronic device 400. In some embodiments, there is a shading mask surrounding an area defined for the LED light to passthrough (e.g., a ring of hard plastic embedded beneath the top surface of the top case 406, where the shading mask is configured to localize the area that LED light passes through on the top case 406. In some embodiments, indications related to neuromuscular signal sensing activity and/or battery life can be presented via LED light through the LED opening 408.

Figure 4B:
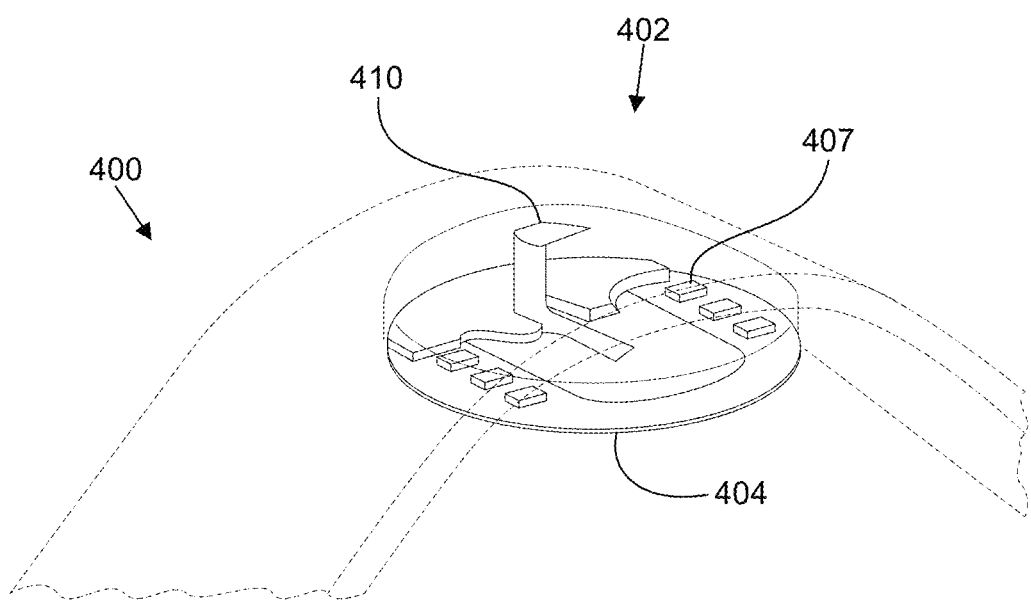

FIG. 4B shows a perspective view of the wearable electronic device 400, including a plurality of components housed in the cavity defined by the bottom case 404 and the top case 406. For example, the bottom case 404 can include one or more electronic components of the compute core 402. In some embodiments, the bottom case 404 is manufactured via a two-shot molding process. In some embodiments, the first shot of the molding process includes molding stamped contacts (e.g., contact points of neuromuscular signal sensing electrodes) to the bottom surface of the bottom case 404. In some embodiments, the second shot of the two-shot molding process includes molding an enclosure over electronic components of the bottom case 404. In some embodiments, the bottom case 404 is molded to include one or more sensor-placement openings defined on a lower surface of the bottom case 404, such that the proud electrodes can be placed into the sensor-placement openings.

In accordance with some embodiments, the bottom surface of the bottom case 404 includes plated through hole (PTH) pin mounts. Charging pins can be coupled (e.g., laser-soldered) to the PTH pin mounts. There can be between 4 and 16 charging pins on the bottom surface of the bottom case 404. The bottom case includes keepout blocks such as a component keepout block 407 to prevent electrical components from being placed within a threshold distance of the charging pins. The keepout blocks can have a maximum height profile of between 0.5 millimeters and 0.75 millimeters.

The bottom case 404 includes a flex assembly 410 (e.g., a dome flex), which can be configured to secure assembled components of the compute core 402 in a particular position and/or orientation (e.g., one or more baseplates, mid-plates, and/or components configured to rest on the respective plate structures). In some embodiments, the lower surface of the bottom case 404 defines one or more openings corresponding to the location of one or more charging pins. In some embodiments the charging pins are configured to attach to the PCB (e.g., via fuzz buttons, and/or flex assemblies configured to define conductive paths between particular locations within the compute core 402). In some embodiments, one or more stiffener components (e.g., a stiffener component 408) are placed on a top surface of the PCB, which can be configured to reduce flex of the PCB.

Figure 4C:
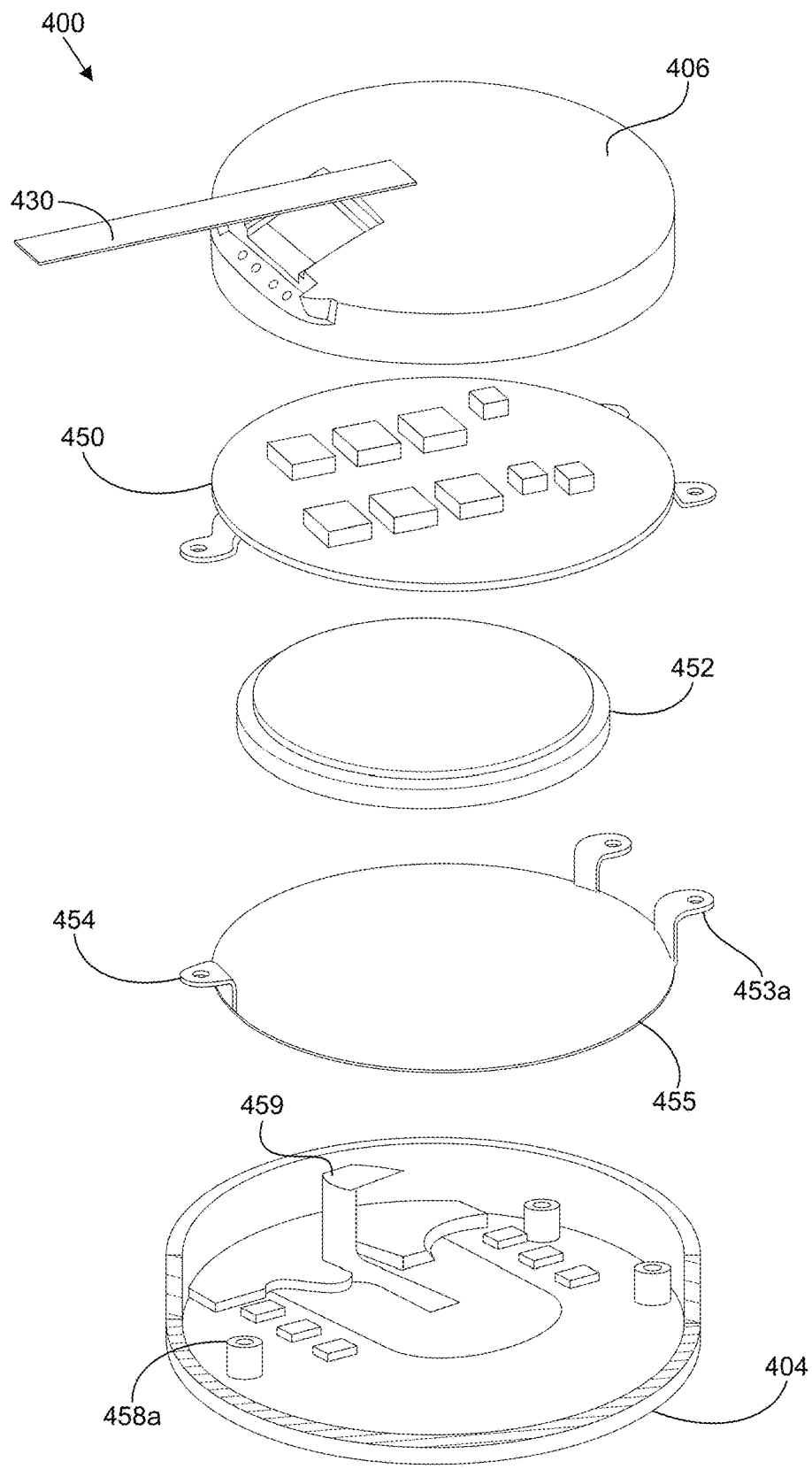

FIG. 4C shows a perspective exploded view of components of the compute core 402. As discussed in FIGS. 4A-4B, the compute core 402 includes the bottom case 404 and the top case 406. A PCB 450 can be housed within the compute core 402 by the top case 406 and/or the bottom case 404. In some embodiments, the compute core 402 further includes a battery 452 configured to power electronic components, including electronic components of the compute core 402 and electronic components located in the band portion(s) described above. In some embodiments, the battery is configured to provide between 100-200 milliampere hours of power on a full charge (e.g., a 148 mAh battery pack capacity). In some embodiments, the battery 452 has a height of between 15-40 millimeters. In some embodiments, an insulating shim (e.g., an Fr-4 epoxy resin shim) is coupled to a top surface of the battery 452 to shield the battery 452 from components of the PCB, and vice versa. In some embodiments, a pressure-sensitive adhesive is used to couple the insulating shim to the top surface of the battery 452. In some embodiments, one or more pressure sensitive adhesives having respective thicknesses of at least 50 micrometers are pre-assembled to a bottom-side of the battery 452 or a pack containing the battery (e.g., an insulating sleeve surrounding the battery 452), and the battery can be pressed into a stainless-steel carrier on the bottom case 404 of the compute core 402. In some embodiments, a layer of polyether ether ketone (PEEK) is wrapped around the battery 452. In some embodiments, the layer is between 10 and 30 micrometers thick (e.g., 20 micrometers).

In some embodiments, the compute core 402 includes a baseplate 454 configured to seat the battery 452 while it is coupled with the PCB 450. In some embodiments, the baseplate 454 is configured to couple with an interior surface of the bottom case 404. In some embodiments, the PCB 450, and the baseplate 454 have distinct fastening structures (e.g., a fastening structure 453a) in corresponding locations, such that the PCB 450 and the baseplate 454 can, when fastened together, encapsulate the battery 452. In some embodiments, the carrier is stamped stainless steel that is configured to shield electrodes on the bottom case 404 from the PCB 450. In some embodiments, the baseplate 454 includes one or more ledges on a top edge 455, and the ledges can be configured to mount the PCB 450. In some embodiments, the PCB 450 is configured to be electrically connected to the baseplate 454, which can further shield the PCB 450 from electrodes on the bottom case 404 of the compute core 402.

In some embodiments, the PCB 450 is a double-sided breadboard that has electrical components on both of a top side and a bottom side. In some embodiments, the bottom side of the PCB has a maximum component height of between half a millimeter and one millimeter. In some embodiments the PCB 450 is configured to fit within a 26-millimeter height. In some embodiments, the top surface of the PCB 450 and the bottom surface of the PCB 450 include clips configured to receive the ends of the service loops 482 and 484. In some embodiments the PCB 450 includes at least one power management integrated circuit (PMIC) that controls power delivered from the battery 452. In some embodiments, the PCB includes at least one sensor data processing unit configured to process data from EMG sensors of the wearable electronic device. In some embodiments the PMIC is configured to communicate with the sensor data processing unit to determine how much power to supply to each of the EMG sensors based on the respective EMG sensors' fidelity. In some embodiments, the PCB includes a flash memory unit. In some embodiments, the PCB includes one or more antenna clips configured to receive and secure antennas extending from the FPC (e.g., antennas configured to transmit biopotential signal data from the biopotential-signal-sensing electrodes to the PCB). In some embodiments, one or more of the antenna clips is configured to contact and form an electrical connection with one or more laser device structuring (LDS) components etched into an interior surface of the top case 406.

In some embodiments, one or more of the components shown in FIG. 4C are fastened to the bottom case 404. In some embodiments, the bottom case 404 includes various mounting structures (e.g., a mounting structure 458a) for receiving the one or more components that are configured to be fastened to the bottom case. A component shelf 459 extends upward from an inner surface of the bottom case 404, where the component shelf can be configured to surround components that are fastened to the bottom case 404. In some embodiments, pressure-sensitive adhesive is applied to one or more of the components that are fastened to the bottom case. In some embodiments, a textile material is wrapped around some or all of a coupling edge of a bottom surface of the top case 406, such that the bottom case 404 is coupled with a portion of the top case 406 that is surrounded by a textile material. In some embodiments, a glue channel is applied to a coupling edge of the top case and/or textile material that surrounds the coupling edge of the top case 406, and the glue channel is configured to be pressed against a coupling edge of the bottom case 404. In some embodiments, a total coupling width of the top case 406 and the bottom case 404 (e.g., a thickness of the combined coupling edge formed by the top case and the bottom case is configured to be less than five millimeters. In some embodiments, the total coupling width is configured to be less than 3.5 millimeters. In some embodiments, the total coupling width is configured to be less than 2.75 millimeters. In some embodiments, a flex stiffener structure is mounted to the bottom case to reduce bending of electrical components configured to be housed within the bottom case.

Figure 4D:
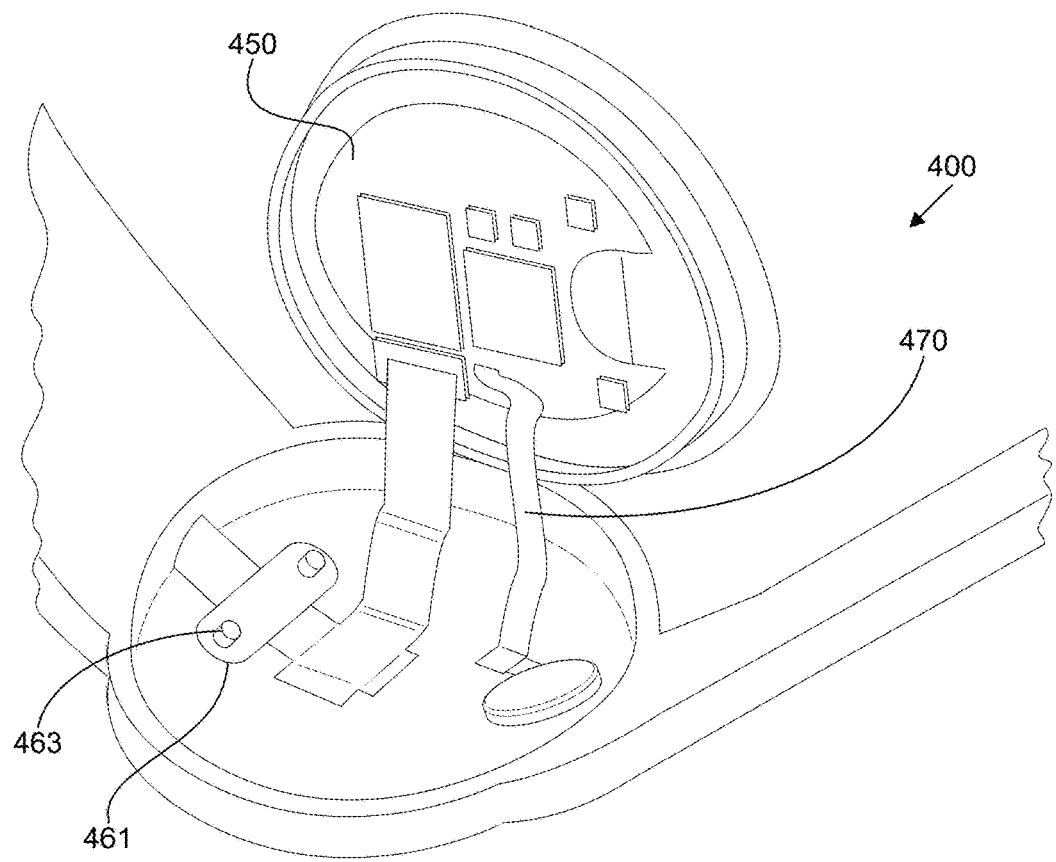

FIG. 4D illustrates a connection of electronic components to a back side of the PCB 450 of the compute core 402. In some embodiments, the compute core includes a laser direct structuring (LDS) antenna component 470, wherein the LDS antenna component 470 is configured to be communicably coupled with one or more electronic components that are not physically connected with the PCB 450 or the LDS antenna component 470. In some embodiments, a service loop 472 connects the LDS antenna component 470 with the PCB 450. In some embodiments, the service loop is bent so as to remain flush against an inner surface of the top case 406. In some embodiments the service loop coupling the LDS antenna component 470 with the PCB is greater than 20 millimeters. In some embodiments, a distinct and separate service loop connects an FPC 474 to the PCB 450. In some embodiments, the service loop that connects the FPC 474 to the PCB 450 is a portion of the FPC 474 that extends beyond a fastening structure 476 that fastens the FPC to the top case 406 of the compute core 402. In some embodiments, the back side of the PCB 450 includes a debug connector, such that hardware and/or software of the PCB 450 can be tested and/or verified without removing the front side of PCB 450 from the bottom case.

Figure 4E:
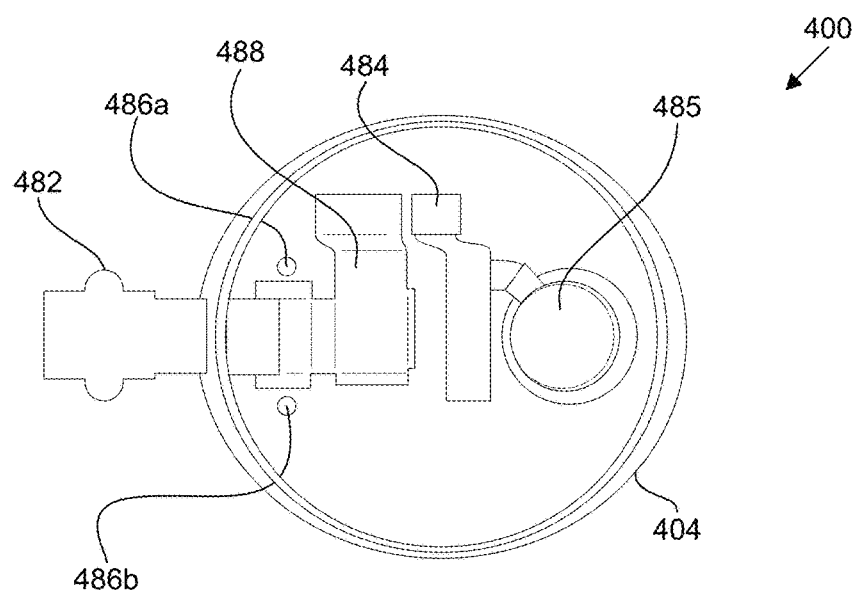

FIG. 4E illustrates a bottom view of the top case 406 of the compute core 402. There can be various geometries etched or otherwise disposed onto and/or into an interior surface of the top case 406. In some embodiments, the geometries include paths for service loops that connect electronic components within the compute core 402 (e.g., a service loop 482 and the service loop 484). In some embodiments, the service loop 482 extends from an FPC and is configured to fold over itself to fasten to adhesive attached to the top case 406. In some embodiments, the service loop is 482 is configured to include a bent edge 488 that is configured to extend downward and form a contact with an antenna pin mounted to the PCB 450. In some embodiments the service loop 482 is configured to be threaded through a portion of the top case 406. In some embodiments, the service loop 482 of the FPC includes an LED and/or a capacitive touch-sensing device. In some embodiments, the service loop 482 is configured to house wiring for more than one component; for example, the service loop 482 can house wiring from one or more neuromuscular-signal sensors (e.g., EMG sensors having electrodes that are coupled to a band portion of a wearable electronic device), as well as wiring from a power source for the LED. In some embodiments, a linear resonant actuator (LRA) 485 is configured to mount to the top case 406. In some embodiments, there is a corresponding notch in the PCB 450 to accommodate a height of the LRA 485. In some embodiments, at least one LDS is etched into an inner surface of the top case 406, such that contact pins of the circuit board 450 are configured to couple with at least one LDS on the top case 406 to form a connection with an FPC.

FIG. 5 illustrate an example method for manufacturing an example biopotential-signal sensor structure, in accordance with some embodiments.

FIG. 5 illustrates a first assembly process 500, after an operation of the method 500 that includes overmolding (510) two biopotential-signal-sensing contact points 504 and 506 onto a carrier component 502. The carrier component is configured to electrically separate the two biopotential-signal-sensing contact points 504 and 506 (e.g., electrodes) from each other. In some embodiments, there are electronic contact points on a bottom surface of the carrier component 502, such that electrical contacts of a respective AFE, which can be directly under the carrier component 502 or in proximity thereto, can form electrical connections with each of the biopotential-signal-sensing contact points.

After the overmolding, each of the two biopotential-signal-sensing contact points 504 and 506 has (512) a first shape and the carrier component 502 has a second shape. In some embodiments, the biopotential-signal-sensing contact points are arranged such that the first shape of each of the two biopotential-signal-sensing contact points extends beyond each outer edge of the second shape of the carrier component. In this way, the two biopotential-signal-sensing contact points 504 and 506 are able to be milled down, such that they will be flush with the outer edges of the carrier component 502.

Turning now to FIG. 5B, the method 500 includes milling (520) the biopotential-signal sensor structure such that each of the two biopotential-signal-sensing contact points 504 and 506 have a third shape, which can be the same shape facing in different directions while mounted on the carrier component 502. In some embodiments, the carrier component 502 has a fourth shape distinct from the second shape.

After the milling, the neuromuscular sensor structure becomes (522) a seamless structure that is configured to allow multiple neuromuscular signal sensors to be placed on a wearable device. In some embodiments, the wearable device is a wearable electronic device. As described with respect to this method, "seamless" can mean substantially flush.

After the milling, each of the two biopotential-signal-sensing contact points extends (524) above a wrist-facing surface of the wearable device, such that when the wearable device is worn each of the two biopotential-signal-sensing contact points is configured to protrude into the skin of a user (e.g., of the user's wrist) at a predetermined skin depression depth.

Turning to FIG. 5C, in some embodiments, the method further includes coating (530) the machined dual-channel neuromuscular signal sensor with a coating material. In some embodiments, the coating is applied so as to reduce corrosion (e.g., based on material properties of the coating and/or a way that the coating is applied), ensuring the neuromuscular signal sensor performs consistently over its lifespan. In some embodiments, the coating is configured to insulate the electrodes from mechanical abrasion.

Figure 6A:
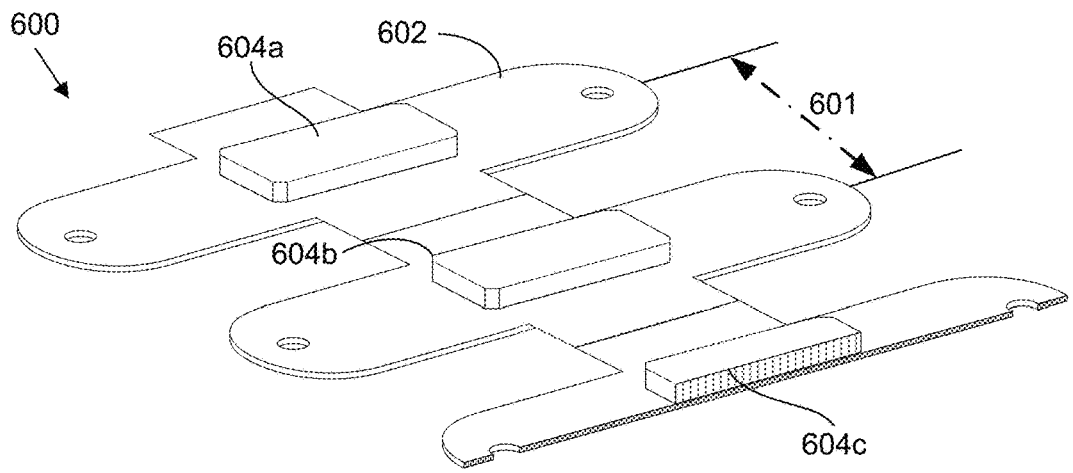
FIGS. 6A-6C illustrate an example band structure for housing example biopotential-signal sensor structures, in accordance with some embodiments.
Figure 6B:
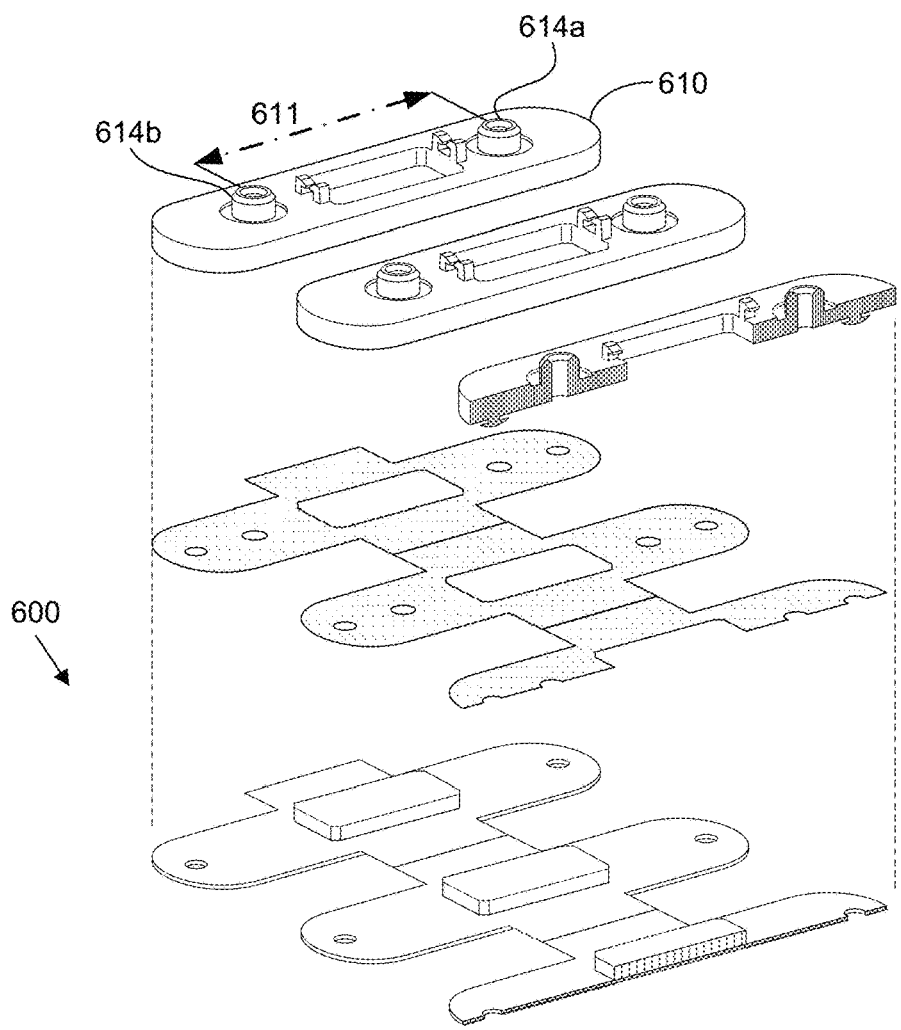
Figure 6C:
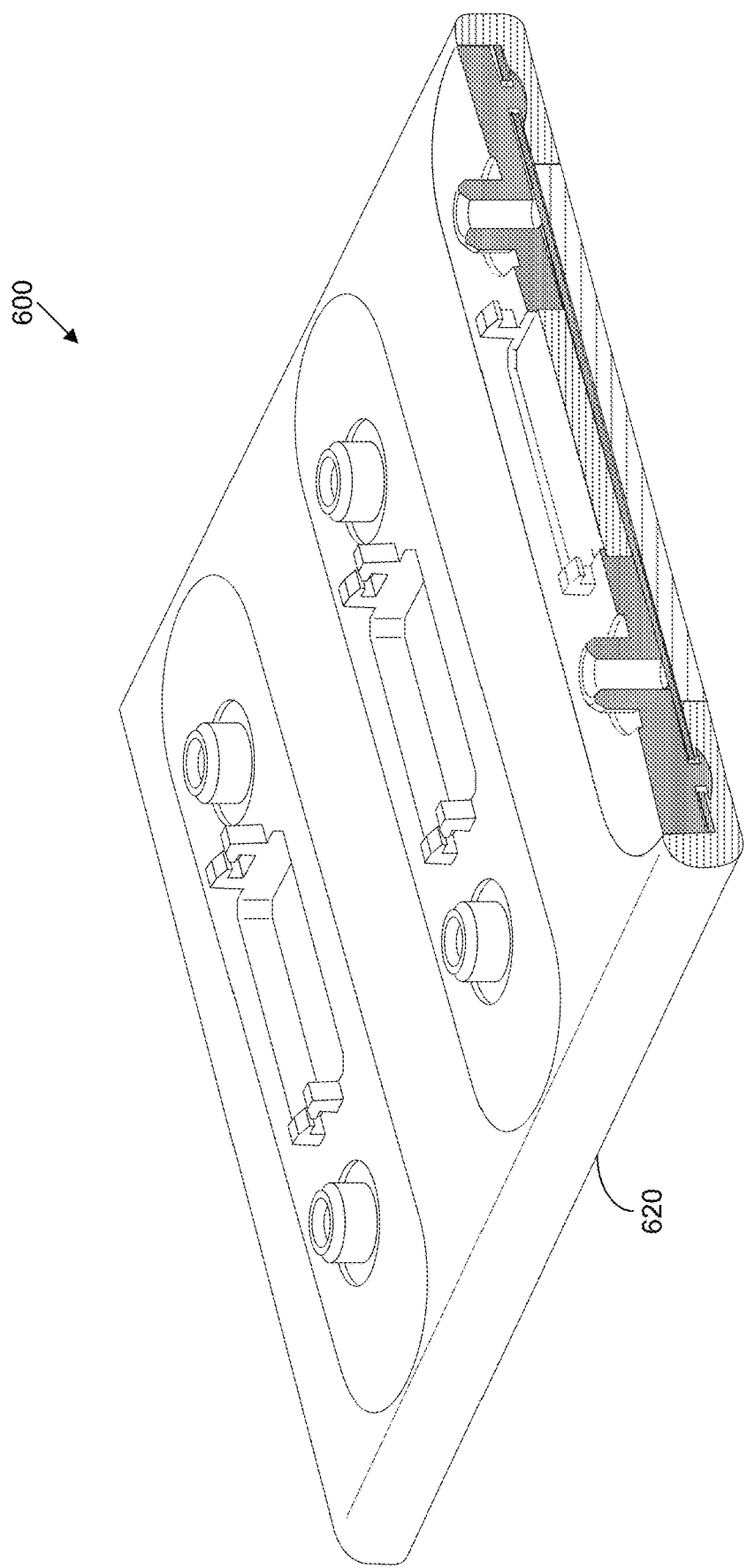

FIGS. 6A-6C illustrate a sub-component view of an example of a band structure 600 for housing example biopotential-signal sensor structures, in accordance with some embodiments. Various components that are not present in one figure of the FIGS. 6A-6C but are present in another figure of the FIGS. 6A-6C, should be understood to be optionally included in each illustration of the band structure 600.

FIG. 6A shows a first illustration of the band structure 600, including a portion of an FPC 602 configured to be embedded within the band structure 600. The portion of the FPC 602 includes several horizontal structure mounts for receiving signal-processing components (e.g., the AFEs 604a-604c) and/or biopotential-signal sensor structures. In some embodiments, the receiving structures have fixed separation distances (e.g., a separation distance 601). In some embodiments, the fixed separation distances are configured to be greater than the minimum separation distance d2 discussed below with respect to FIGS. 16A-16B. In some embodiments, a longest dimension of each of the horizontal structure mounts is at least 60% of a shortest dimension of a band portion of the band structure 600. In some embodiments, the horizontal structure mounts can be more than half as long as the band portion is wide, such that a maximum surface area of the user's body is used for detecting neuromuscular signals. The shape and dimension of the horizontal structure mounts can be configured to ensure that respective electrodes located on the band structure 600 maintain minimum separation distances in at least two directions while the band structure 600 is being worn by the user. In some embodiments, each of the biopotential-signal sensing structures 112a-112f is at least 10 millimeters from any other biopotential-signal sensing structures on the wearable electronic device 100. As shown in FIG. 18, the signal sensing structures 112a-112f can be distributed at particular points along the circumference of a wrist of a user such that electrodes mounted to and/or molded to the biopotential-signal sensing structures 112a-112f are configured to detect neuromuscular signals at certain locations along the user's wrist.

FIG. 6B shows a second illustration of the band structure 600, including receiving structures 610a-610c. Each of the receiving structures 610 includes two coupling components 614a and 614b. In some embodiments the coupling components 614a and 614b are configured to have a separation distance 611. In some embodiments the separation distance 611 is configured to reduce wear on the AFEs 604a-604c. In some embodiments the receiving structures are adhered to the receiving structures 610a-610c with an adhesive component 616.

FIG. 6C shows a third illustration of the band structure 600 after it has been overmolded with an outer material 620, which can include an outer layer of a band portion of the band structure 600 (e.g., the band portion 102 and/or the band portion 104 in FIGS. 1A-1C). The outer material 620 can be made of polyurethane, an elastomer, or another similar material.

Figure 7A:
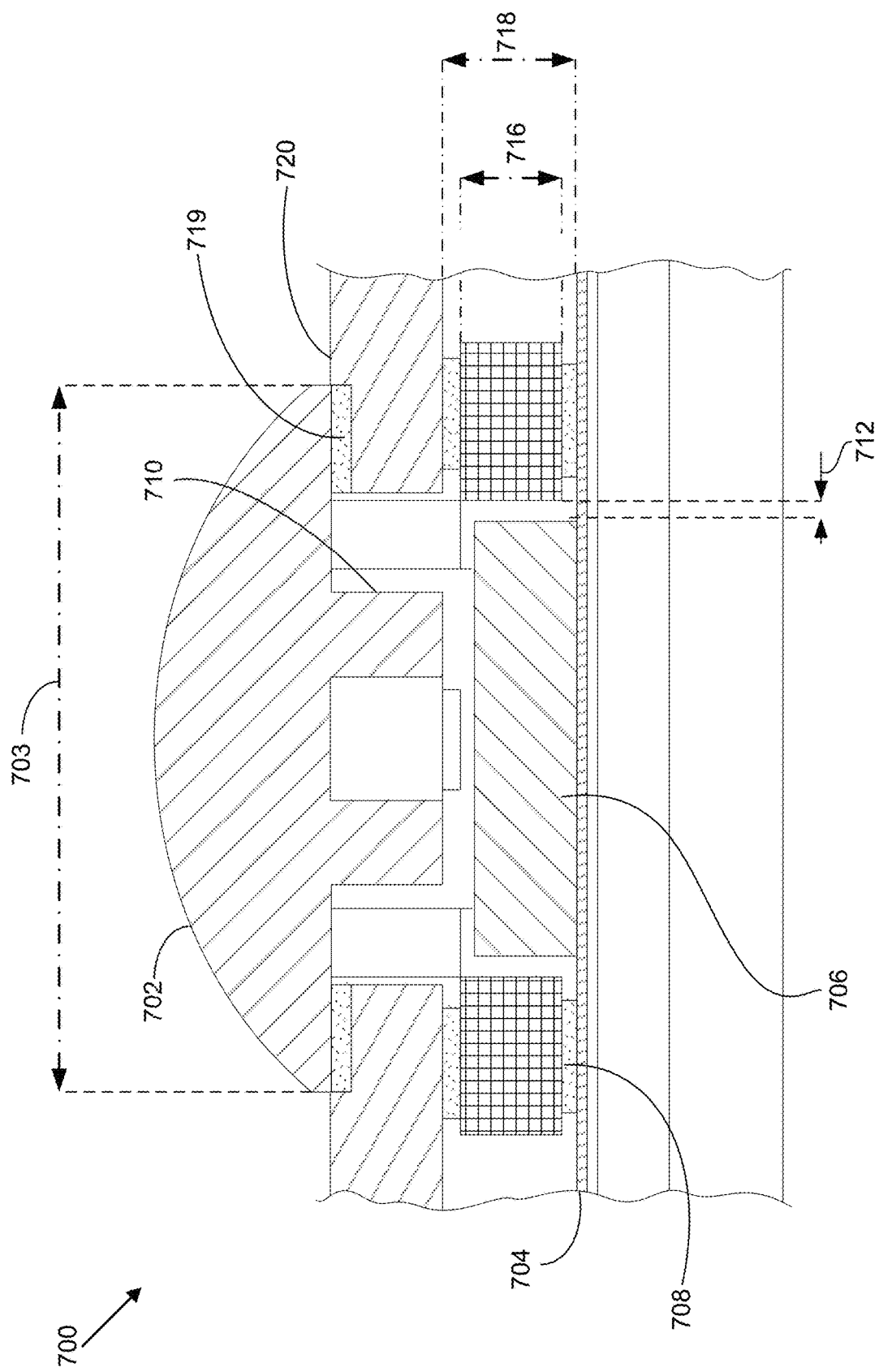
FIGS. 7A-7C illustrate an example band structure that includes a neuromuscular signal sensor coupled with a flexible printed circuit (FPC), in accordance with some embodiments.
Figure 7B:
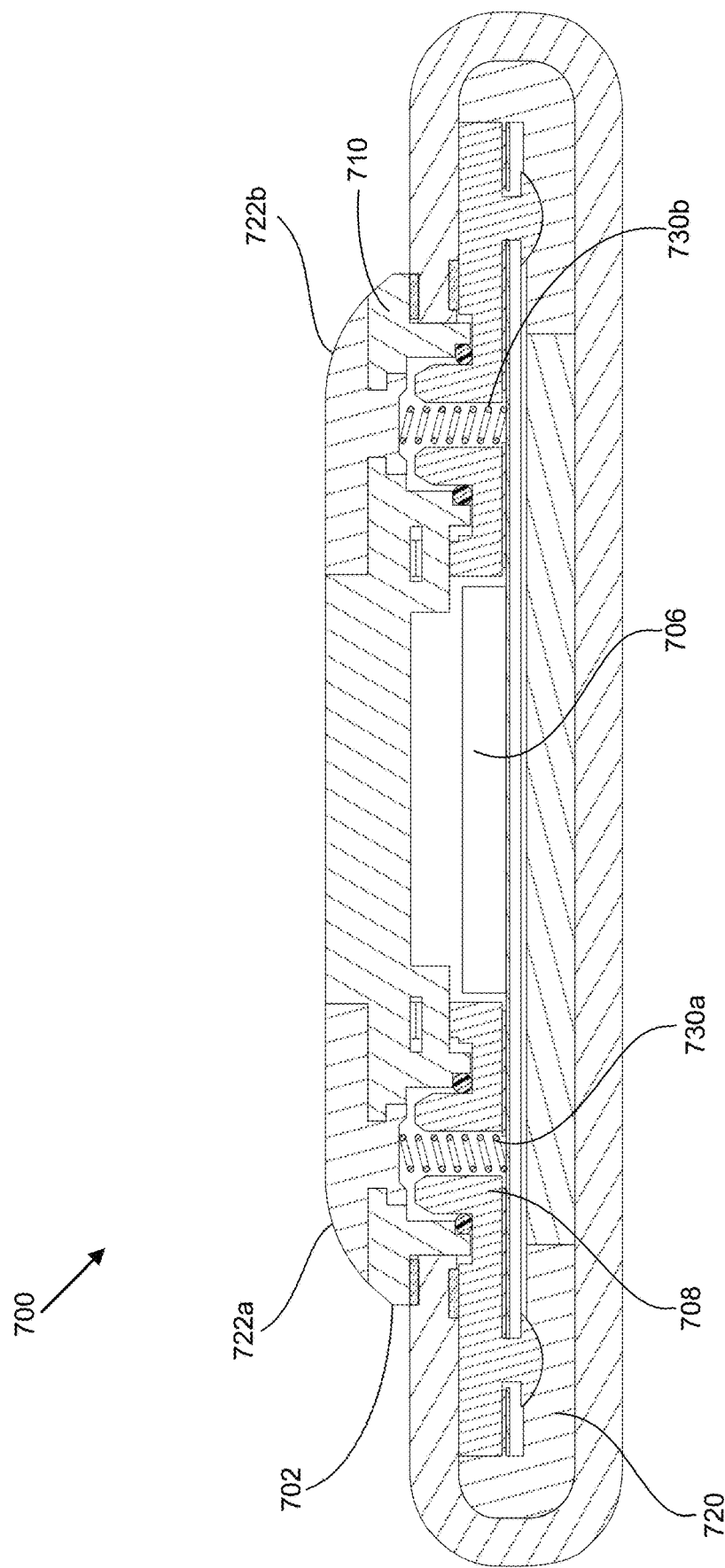
Figure 7C:
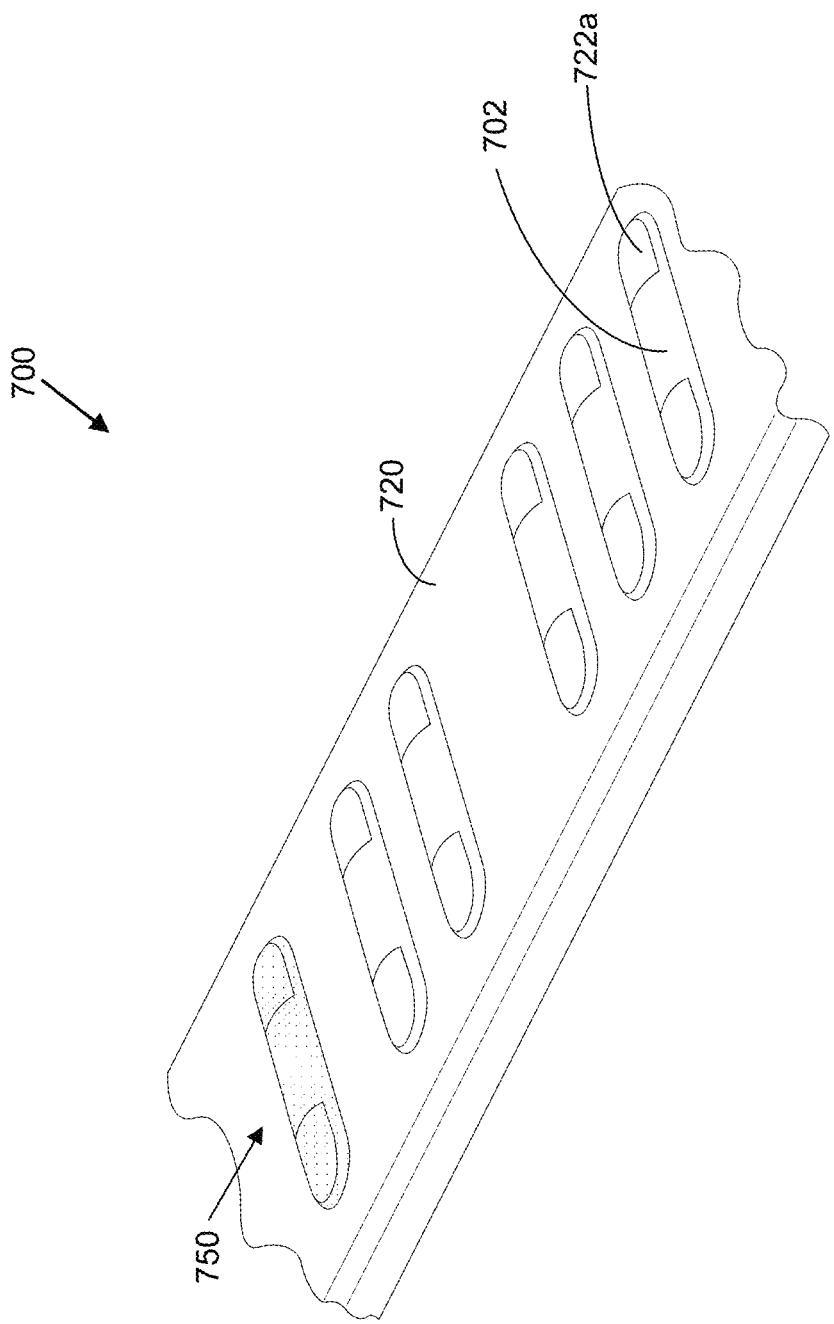

FIGS. 7A-7C illustrate a band 700 that includes a biopotential-signal sensor structure 702 coupled with a FPC 704, which can together be used to at least partially process neuromuscular signals of a wearer of the band 700.

FIG. 7A illustrates a cross-sectional front view of a band 700 that includes a biopotential-signal sensor structure 702 mounted to a receiving structure of the FPC 704. One of ordinary skill in the art will understand that FIG. 7A illustrates only a portion of a band 700, in accordance with some embodiments, and that a plurality of some or all of the components described with respect to FIG. 7A can be positioned at various locations of an embodiment of the band 700. In some embodiments, the biopotential-signal sensing structure has a width 703 between four millimeters and seven millimeters (e.g., five millimeters).

FIG. 7A shows that the FPC 704 includes an AFE 706. In some embodiments, the AFE 706 includes one or more signal-processing components, which can be configured to process neuromuscular signals that can be detected by contact points (e.g., electrodes) on the biopotential-signal sensing structure 702, in accordance with some embodiments. In some embodiments, as shown in FIG. 7A, the AFE 706 can be located proximally to a receiving structure 708. The receiving structure 708 can be configured to receive the biopotential-signal sensing structure 702, which can include one or more electrodes configured to detect neuromuscular signals of a user. In some embodiments, the biopotential-signal sensing structure 702 is configured to snap into the receiving structure 708. In some embodiments, the biopotential-signal sensor structure 702 includes a coupling structure 710 that corresponds to the receiving structure 708. In some embodiments, the coupling structure 710 is configured to have a snap fit with an upward-facing receiving hole defined by the receiving structure 708. In other words, the coupling structure 710 can have a larger size in at least one dimension such that the upward-facing receiving hole of the receiving structure 708 must flex outward, at least temporarily, to allow the coupling structure 710 to snap into the receiving structure 708. In some embodiments, the coupling structure 710 is sized such that the snap fit with the receiving structure does not require enough force to cause damage to any of the electronic components in the biopotential-signal sensing structure 702 and/or the receiving structure 710. In some embodiments, there is a gap 712 between an outer edge of the AFE 706 and an inner edge of the receiving structure 708. In some embodiments, the gap 712 is configured to prevent damage to the AFE 706 and/or the receiving structure 708. In some embodiments, the gap 712 is between 0.1 millimeters and 0.5 millimeters. In some embodiments, the AFE 706 has a width of between two millimeters and four millimeters (e.g., 3.25 millimeters). In some embodiments, the biopotential-signal sensor structure 702 has a width of five millimeters. In some embodiments, an outer edge of the biopotential-signal sensor structure 702 overlaps a textile material portion 719 of the band 700 by overlap distance 714 of between 0.5 millimeters and 1.5 millimeters. In some embodiments, the receiving structure has a height 716 that can be at least 1.6 millimeters. In some embodiments there is a total distance 718 between a top surface of the FPC 704 and a lower surface of an outer portion of the band surface of at least 2.1 millimeters. In some embodiments, there is a layer of structural adhesive between one or both of the top surface of the receiving structure and an inner surface of the band portion, and a lower surface of the receiving structure and the FPC 704.

FIG. 7B illustrates a cross-sectional side view of the band 700 that includes the biopotential-signal sensor structure 702 mounted into the receiving structure 708 attached to the FPC 704. As was shown in FIG. 7A, the receiving structure 708 can be configured to couple with the coupling portion 710 of the biopotential-signal sensor structure 702. In some embodiments, the neuromuscular sensor structure 702 includes a carrier component 720 and one or more biopotential-signal-sensing contact points (e.g., 722a, 722b) mounted to the carrier component 720. In some embodiments, the one or more biopotential-signal-sensing contact points are electrodes configured to sense neuromuscular signals based on contact with the skin of a user. In some embodiments, as illustrated in FIG. 7B, there are two biopotential-signal-sensing contact points on the carrier component 720, a first neuromuscular-signal contact point 722a, and a second neuromuscular-signal contact point 722b. In some embodiments, respective springs 730a and 730b are configured to connect a top surface of the FPC 704 with the respective contacts points 722a and 722b.

FIG. 7C illustrates a perspective view of the band 700 from a location external to all of the components of the band portion 700. Any of the internal components described with respect to FIGS. 7A-7B can be encased by a layer of elastomeric material and/or a layer of textile material as depicted by the perspective view of the band 700. In some embodiments, a metallic and or epoxy coating 750 is applied to one or more components of each biopotential-signal sensor structure of the band portion (e.g., the biopotential-signal sensor structure 702).

FIGS. 8A-8G illustrate a method of assembling a wearable electronic device, in accordance with some embodiments. The wearable electronic device can include some or all of any of the components of the wearable electronic devices described herein (e.g., the wearable electronic device 100). Likewise, the wearable electronic device 100 can include any components described with respect to FIGS. 8A-8G.

Figure 8A:
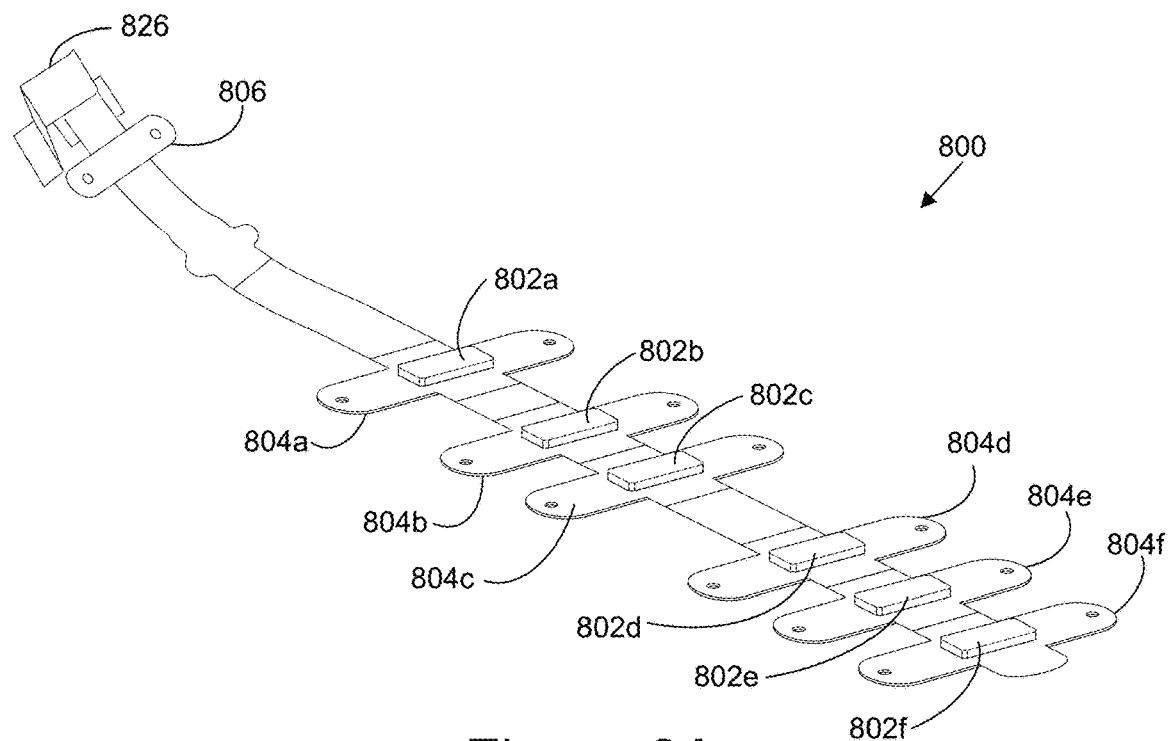
FIGS. 8A-8G illustrate a method of assembling a wearable electronic device, in accordance with some embodiments.

FIG. 8A illustrates an example FPC 800 after a first shot-molding operation. The FPC 800 includes six electrode-placement structures 804a to 804f. Each of the electrode-placement structures 804a-804f is configured to receive a carrier component of a neuromuscular signal-sensing structure (e.g., the biopotential-signal sensing structure 702 shown in FIGS. 7A-7C). Each of the electrode-placement structures 804a to 804f includes at least one signal-processing component (e.g., AFEs 802a to 802f). In some embodiments, the FPC 800 is configured to provide electrical signals from one or more biopotential-signal sensing structures (e.g., the biopotential-signal sensing structures 112a-112f) to a compute core which can be detachably coupled with the electrode-placement structures 804a-804f.

In some embodiments, each biopotential-signal sensing structure of the biopotential-signal sensing structures to be attached to the placement structures 804a-804f is configured to partially process neuromuscular signals that are sensed (e.g., detected) by the respective AFEs 802a-802f. In some embodiments, the FPC 800 is configured to adjust power to one or more of AFEs 802a-802f based on the signal being received at the respective neuromuscular signal sensors.

In some embodiments, the first shot-molding operation includes coupling a bend-stiffening component to the FPC 800, which causes the FPC 800 to have a higher resistance to axial rotation around the longest dimension of the FPC 800. In some embodiments, a fastening structure 806 (e.g., an anchoring structure) is molded to the FPC 800. The fastening structure 806 is configured to attach the FPC 800 to a housing structure (e.g., the compute core 402 in FIG. 4A). A service loop 826 extends past the fastening structure 806, and the service loop 826 is configured to form an electronic connection between the FPC 800 and one or more processing components of the compute core coupled with the fastening component 806. In some embodiments, a first end of the service loop 826 of the FPC 800 is to be coupled (e.g., fastened) to an inner coupling portion of a compute core (e.g., the compute core 402 in FIGS. 4A-4E) via one or more stainless steel micro-fasteners. In some embodiments a portion of the service loop 826 extends beyond the coupling point of the FPC 800 to a location inside the compute core 108, such that a portion of the service loop 826 physically contacts a coupling component of a centralized processor within the compute core 108.

Figure 8B:
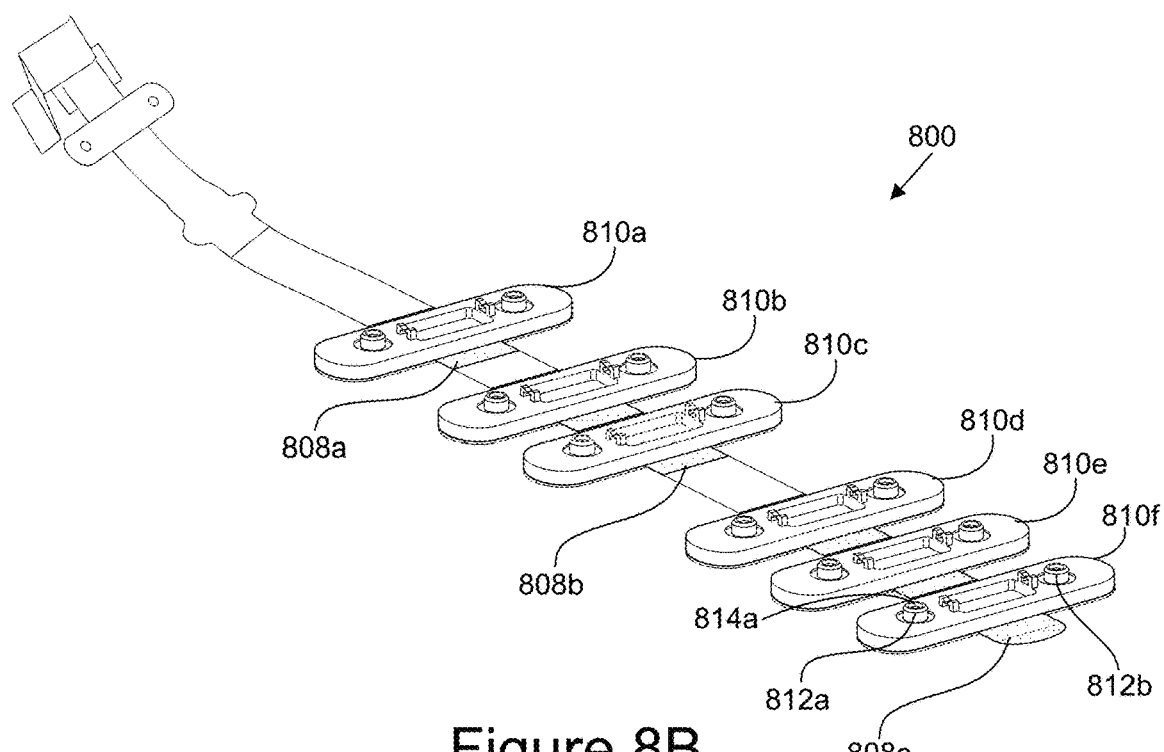

FIG. 8B illustrates an example FPC 800 after a second shot-molding operation. During the second shot-molding operation, one or more pressure-sensitive adhesive sections 808a-808c can be attached to one or more of the electrode-placement structures 804a-804f such that they can be pressed into the FPC 800. In some embodiments the adhesive interfaces include a low dielectric and/or loss tangent adhesive film, which can also be configured to be a thermosetting film (e.g., it can be detachable when applied to the FPC 800, but it becomes permanently adhered to the FPC 800 when heated). In some embodiments, there are two layers of adhesive that are made of different materials. For example, one layer of the adhesive can be made of a material that is configured to be coupled with one or more of the electrode-placement structures 804a-804f, and another layer of the adhesive can be made of a material that is configured to be coupled with one or more of the receiving structures 810a-810f. For example, there can be a first layer of adhesive that is a pressure-sensitive adhesive configured to form a detachable bond with the FPC 800 such that if the pressure-sensitive adhesive were ever removed from the FPC 800 there would be little to no residue remaining on the FPC 800. As shown in FIG. 8B, in some embodiments, two or more of the electrode-placement structures 804a-804f can be attached to the FPC 800 by the same pressure-sensitive adhesive section (e.g., the pressure-sensitive adhesive section 808c corresponds to three of the electrode-placement structures on the FPC 800 (e.g., electrode-placement structures 804d-804f)).

During the second shot-molding operation, one or more receiving structures 810a-810f are molded onto the FPC 800. Each of the receiving structures 810a-810f can include one or more mounting pins, such as mounting pins 812a and 812b. The mounting pins 812a and 812b can be used to snap into coupling portions of one or more biopotential-signal sensing structures (e.g., coupling portions 710 of the neuromuscular signal-sensing structure 702). In some embodiments, each of the mounting pins defines an electrical contact opening (e.g., an electrical contact opening 814a) which can house a metal spring (e.g., either of the springs 730a and 730b in FIG. 7B). The springs 730a and 730b can extend from a top surface of an electrode-placement structure of the FPC 800 to a bottom surface of a neuromuscular sensing contact point (e.g., either of the biopotential-signal-sensing contact points 722a and 722b). In some embodiments, the respective springs are configured to form an electrical connection between a respective neuromuscular signal sensing contact point and an AFE corresponding to a respective electrode-placement structure (e.g., the electrode-placement structure 802f).

Figure 8C:
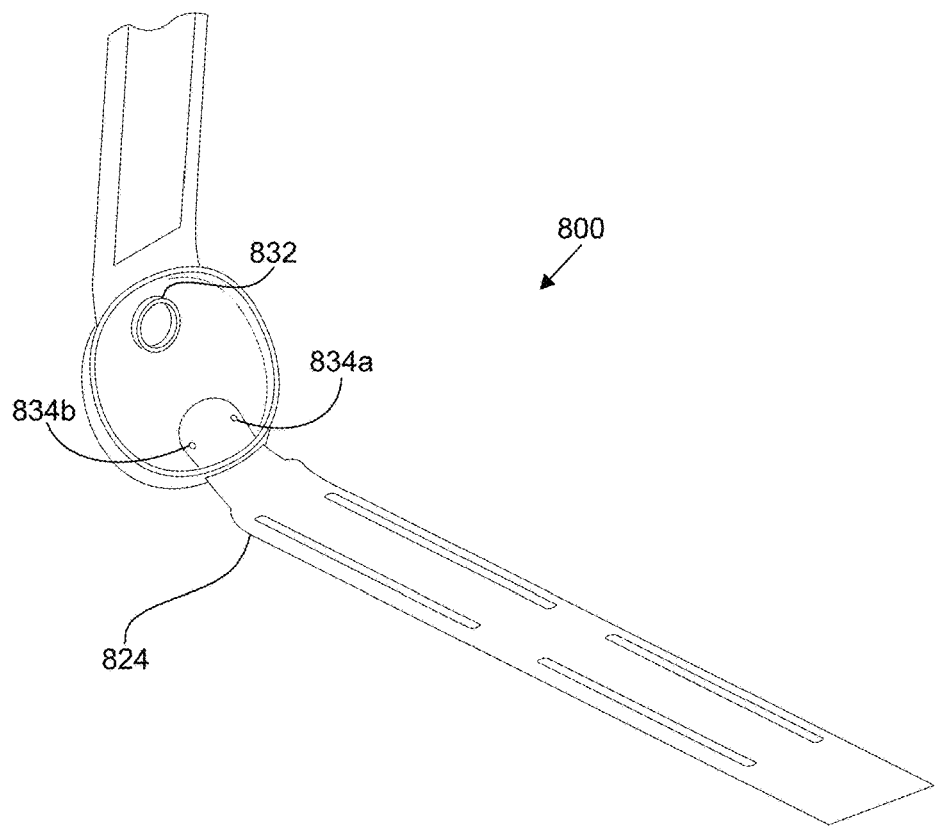

FIG. 8C shows a strain relief strand 824 that has a fastening end 832 that is configured to extend past the fastening structure 806 of the FPC 800. In some embodiments, the strain relief strand 824 extends past a fastening point of the fastening structure 806 by at least three millimeters, which can allow more strain force to be applied to the strain relief strand 824. The fastening end 832 defines two mounting holes 834a-834b which are configured to receive mounting pins of a compute core (e.g., the microfastener 463 in FIG. 4D).

Figure 8D:
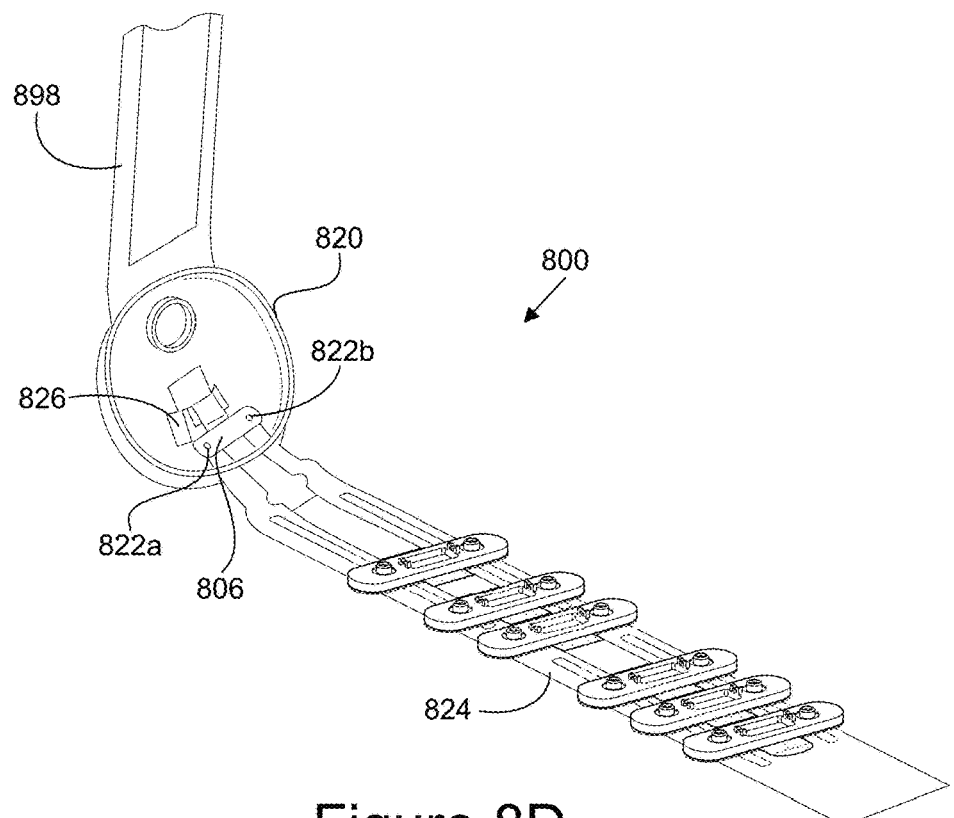

FIG. 8D shows the FPC 800 being attached to a top case 820 of a compute core. In some embodiments, the top case 820 includes two mounting pins for receiving the fastening structure 806 via a set of mounting holes 822a-822b of the fastening structure 806. In some embodiments, the FPC 800 is also attached to a strain relief strand 824 that extends from the top case 820 past the end of the FPC 800. The service loop 826 extends beyond the fastening structure 806. In some embodiments, the portion of the service loop 826 that extends beyond the fastening structure 806 is configured to form at least one electrical connection between two or more of the respective AFEs 802a-802f and processors of a compute core. The top case 820 is coupled to a band portion 898 that does not include any electronic components, in accordance with some embodiments. In some embodiments, the top case 820 is molded to the band portion 898 during one of the shot-molding operations described with respect to FIGS. 8A-8C.

Figure 8E:
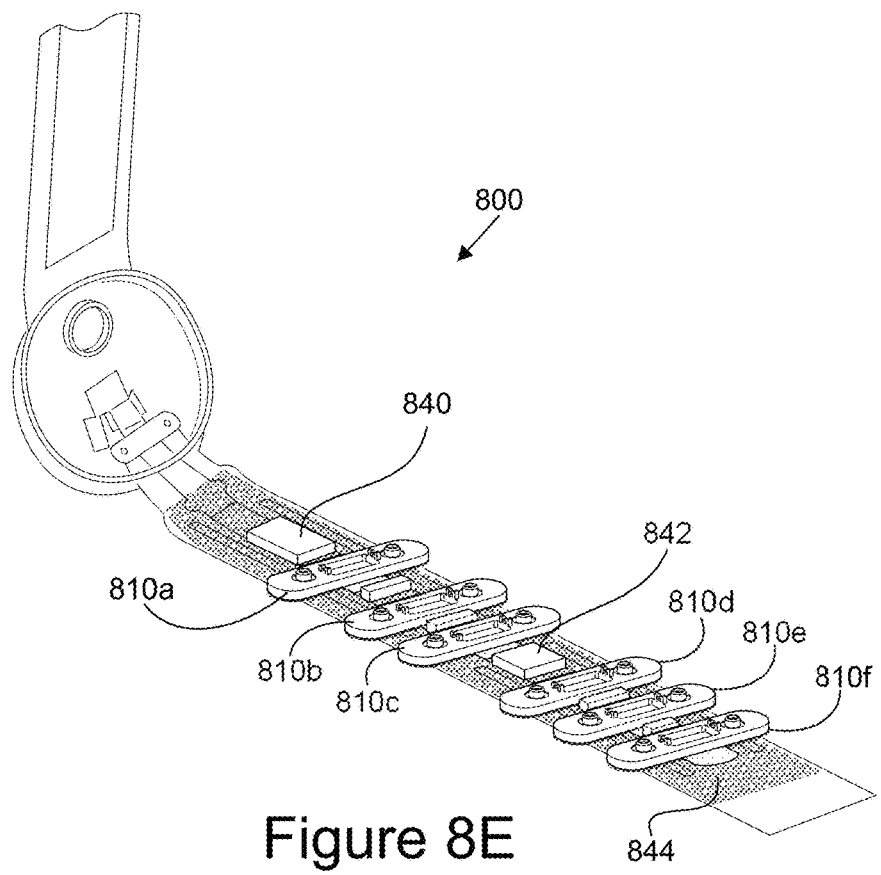

FIG. 8E shows an overmold tool 840 being placed over the FPC 800, such that the FPC is held down against the strain relief strand 824. The overmold tool 840 includes at least one hold-down block 842. The hold-down blocks are configured to secure one or more of the electrode placement structures 802a-802f to the strain relief strand 824. In some embodiments, one or more of the hold-down blocks are attached to the strain relief component 824 or are configured to couple with the electrode placement structures of the FPC 800, via one or more magnets disposed on a lower surface of the overmold tool 840. In some embodiments, the overmold tool 840 and its hold-down blocks (e.g., the hold-down block 842) are configured to ensure a separation distance between each respective receiving structure 810a-810f of the FPC 800. In some embodiments, there is paramagnetic chain 844 disposed beneath the FPC 800. The paramagnetic chain can be between 25-75% of the length of the FPC 800.

Figure 8F:
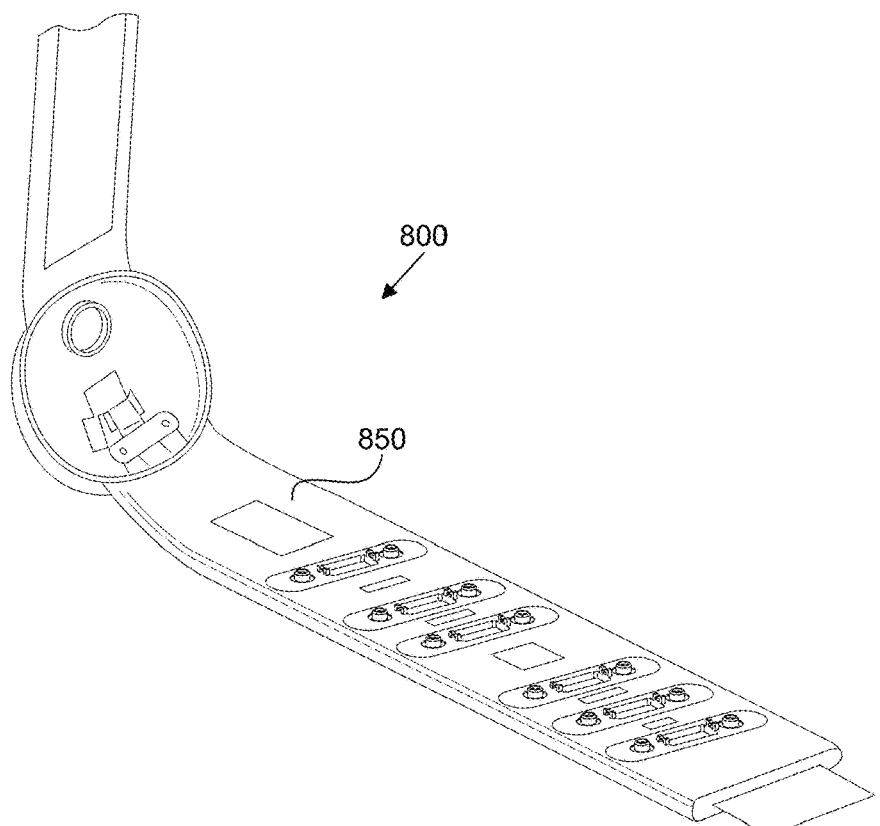

FIG. 8F shows an overmolding layer 850 encasing the FPC 800. The overmold layer 850 can be made of a soft material that is configured to secure components (e.g., receiving structures 810a-810f) in place while allowing the FPC 800 to bend in a latitudinal direction. In some embodiments, the hold-down blocks of the overmold tool 840 are configured to prevent some amount of latitudinal bending. In some embodiments, a bend-stiffening material is included in the overmold layer, which is configured to prevent the FPC from rotating around a longitudinal axis of its longest dimension.

Figure 8G:
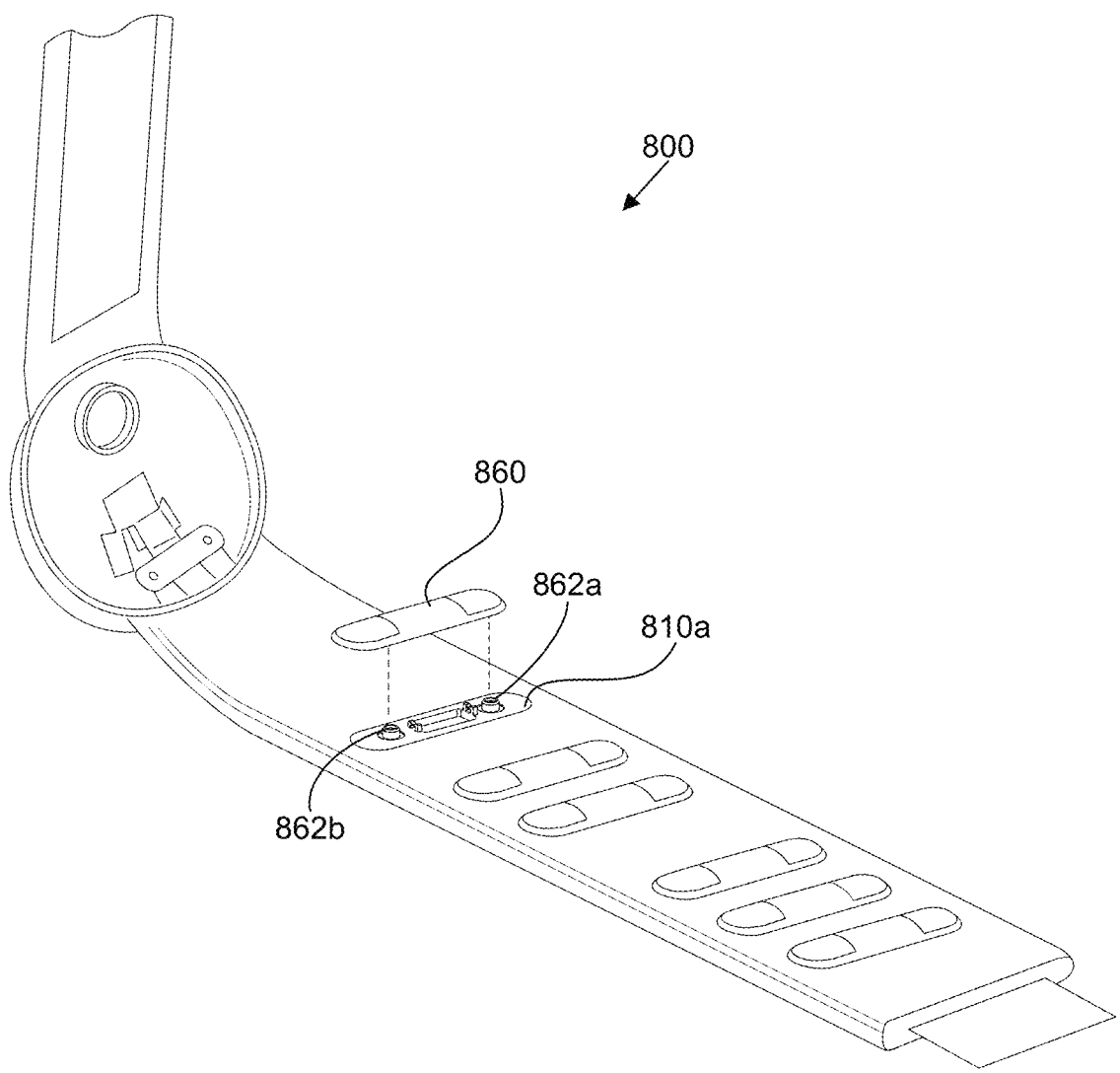

FIG. 8G illustrates an example of a biopotential-signal sensing structure 860 being placed onto an exposed portion of the receiving structure 810a. In some embodiments, respective coupling components of the receiving structures 810a-810f are configured to be exposed after the overmold layer 850 is applied to the FPC. In some embodiments, the coupling components are configured to couple with respective fastening structures located on the bottom of respective neuromuscular signal-sensing structures (e.g., the biopotential-signal sensing structure 810a). In some embodiments, there are two radial fastening structures on a bottom surface of the biopotential-signal sensing structure 860, and there is at least one additional fastening structure that extends parallel to a major dimension of the biopotential-signal sensing structure. In some embodiments, each of the radial fastening structures on the bottom surface of the biopotential-signal sensing structure 860 is configured to couple with respective coupling components 862a and 862b of the receiving structure 810a. In some embodiments, there is a plurality of snapping engagement surfaces on one or more of the biopotential-signal sensing structure 860 and the receiving structure 810a.

FIGS. 9A-9I illustrate example bands (e.g., a band 900, a band 910, a band 920, a band 930, a band 940, a band 950, a band 960, a band 970, a band 980) that include a textile-based material with a compute-core region sized to surround a compute core, in accordance with some embodiments. Each of the examples shown in FIGS. 9A-9I illustrates example embodiments of a compute core of a respective unitary band that includes a textile structure encapsulating the compute core. In some embodiments, the textile-based material is configured to encapsulate a lip of a component of the compute core (e.g., a lip of a top case of the compute core). The compute cores of the example wearable devices shown in FIGS. 9A-9I include different textile encapsulation techniques, which can be used alone or in combination.

In some embodiments, angled portions of the textile material (which can be composed entirely of textile material, or a composite of textile material and other material, such as plastic) are configured to define a geometrically shaped opening, which is referred to as a compute-core region according to some embodiments. In some embodiments, the compute-core region defined by the textile material is configured to seamlessly surround a perimeter of a compute core of a wearable electronic device (e.g., when the compute core is attached to a band of the wearable electronic device). For the purposes of this particular feature of the bands described herein, seamless should be interpreted as meaning that the textile material completely surrounds the respective perimeter of the compute core, without any gaps or raised edges along the perimeter.

In some embodiments, the geometrically shaped opening includes a portion of textile material that is angled relative to a first adjacent portion of the geometrically shaped opening to allow for coupling the geometrically shaped opening with the perimeter of the compute core. In some embodiments, the perimeter of the compute core includes a connection point between a top case of the compute core and a bottom case of the compute core, as shown in in each of FIGS. 9A-9H (e.g., the top case 904 and the bottom case 906 have a connection point, and there is a lip at one end of the connection point that the textile material 908 is configured to be tucked into. In some embodiments, the connection point includes an adhesive for adhering the portion of textile material that is angled relative to the first adjacent portion of the geometrically shaped opening to the compute core. In some embodiments, at least a portion of the textile material is reinforced internally with an adhered polymer (e.g., an internal film layer 959), which can be useful for (i) maintaining the shape of the geometrically shaped opening and/or (ii) securing the compute core to the compute-core region of the geometrically shaped opening. In some embodiments, as discussed in more detail with respect to FIG. 9G below, a portion of the textile material, which can be proximal to the connection point between the top case and the bottom case of the compute core, can be reinforced both internally and externally by one or more adhered polymer layers and/or other film layers (e.g., an external film layer 967, and an internal film layer 969), which may be separate or continuous along the compute-core region of the geometrically shaped opening.

In some embodiments, the textile-based material is partially made of polymer-based yarn. In some embodiments, the polymer-based yarn is a thermoplastic polyurethane (TPU yarn). In some embodiments, the TPU yarn can be configured to allow for compression molding around the compute core. In some embodiments, one or more light-emitting diodes that are placed beneath an exterior surface of the textile-based material such that they are configured to transmit visible light through the exterior surface (e.g., either beneath the outer surface but configured to provide photonic light through the exterior layer or are physically disposed on the exterior surface of the textile material).

Figure 9B:
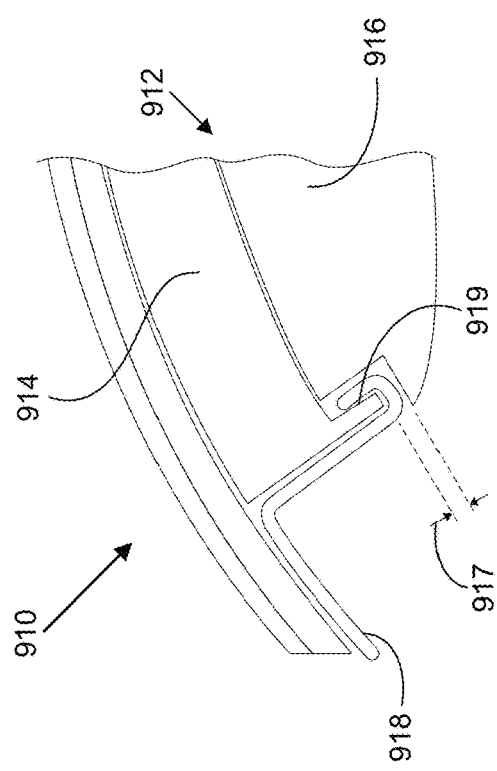
FIGS. 9A-9I illustrate example bands that include a textile-based material with a compute-core region sized to surround a compute core, in accordance with some embodiments.
Figure 9D:
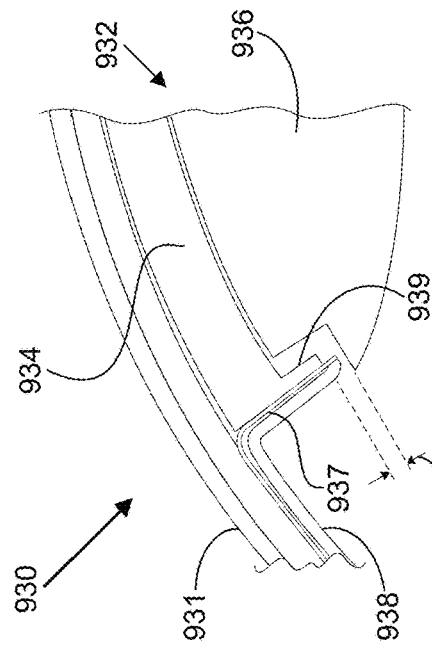
Figure 9A:
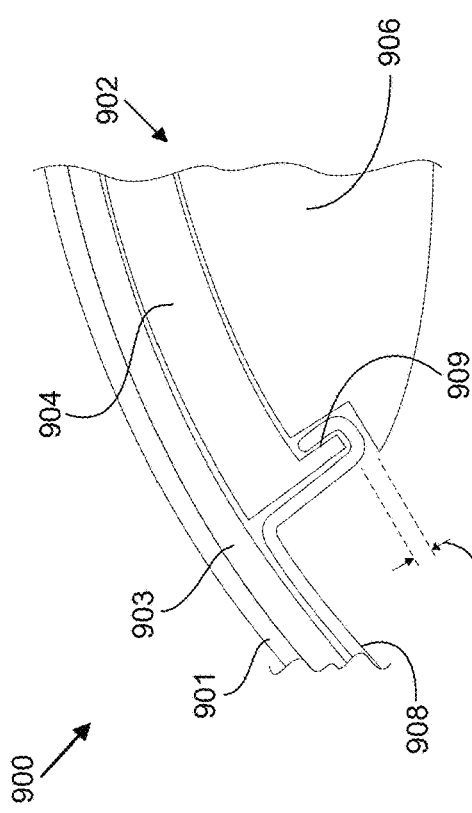

FIG. 9A shows a first example of a band 900 that has a compute core 902. The compute core 902 can include a top case 904 and a bottom case 906, in accordance with some embodiments. In some embodiments, the top case 904 fastens, adheres, or otherwise couples with a band portion of the unitary band 900. In some embodiments, the bottom case 906 is a dome structure configured to extend inward toward skin (e.g., on the wrist) of a user. In some embodiments, the dome structure of the bottom case 906 includes a flat portion that has contact points (e.g., stamped contact points) configured to detect neuromuscular signals of a user. In some embodiments, the contact points of the bottom case 906 are configured to be in electronic configuration with a multi-layer circuit board (e.g., a PCB, which can be a multi-layer board (MLB)) that is inside the compute core that is formed by the top case 404 and the bottom case 406.

In some embodiments, there are corresponding coupling portions of the top case and the bottom case, such that the top case 904 is configured to receive the bottom case 906 (e.g., a snap fit). In some embodiments, there is a gap 907 between an outer edge of a lip 909 of the bottom case 906 and an inner surface of the top case 904. In some embodiments, the gap 907 between the lip 909 and the top surface of the bottom case 906 is configured to receive a portion of textile material 908. In some embodiments, a method of assembling and/or manufacturing the band 900 includes manually adhering the textile material at a 180-degree angle on an inside surface of the lip of the top case 904. In some embodiments, the thickness of the textile material 908 is wider than the gap between the inner surface of the top case 904 and the outer edge of the coupling portion of the bottom case 906, such that the textile material is configured to be compressed to be fed through the gap 907. In some embodiments, the gap 907 has a width that accounts for a larger radius of the bend of the textile material 908 (e.g., a larger radius than is depicted in FIG. 9A). In some embodiments, the portion of the textile material 908 that is bent around lip 909 is configured to have different material properties than other sections of the textile material 908. In FIG. 9A, the gap 907 shown has a "J" shape, such that the textile material 908 can be fed through a first length of the gap, bent around a corner of the gap, and can then fed through a second length of the gap. In this way, the respective surfaces of the top case 904 and the bottom case 906 can apply a greater amount of friction to the textile material 908, such that the textile material 908 is more securely fastened to the compute core 902.

In some embodiments, the band 900 includes an exterior textile material 901 that encapsulates the outer surface of the compute core. In some embodiments one or both of the exterior textile material 901 and the interior textile material 908 are waterproof, or at least water-resistant. In some embodiments, the exterior textile material 901 is made of a different material than the interior textile material 908. For example, the interior textile material 908 can be configured to be more comfortable on a wrist of a user, while the outer textile material 901 can be configured to be more durable, waterproof, tear-proof, and the like. In some embodiments, the exterior textile material 901 and the interior textile material 908 have different thicknesses and are made of the same material. In some embodiments, the exterior textile material 901 and the interior textile material 908 are part of a single textile tube that encapsulates one or more band portions of the band 900. In some embodiments, the portion of the textile material 908 that is configured to be fit between the inner surface of the lip 909 and the outer surface of the bottom case 906 pre-laminated with adhesive. In some embodiments, adhesive is applied (e.g., pre-laminated) to portions of the lip 909 and/or the bottom case 906. In some embodiments, there is a rigid fastener attached to and/or coupled with an inner surface of the lip 909. In some embodiments, an outer surface of the textile material 908 is configured to be flush with an outer surface of the bottom case 906 at the connection point between the textile material 908 and the bottom case 906.

FIG. 9B shows a second example of a band 910 that has a compute core 912. The compute core 912 has similar structural elements to those shown in FIG. 9A, such as top case 924 and a bottom case 926. But in FIG. 9B, a height of the top case 904 is thicker than a height of the top case 904 in FIG. 9A. Similar to the components of the compute core 902 shown in FIG. 9A, the components of the compute core 912 shown in FIG. 9B can include a gap 917 between a lip 919 of the top case 924 and an outer surface of the bottom case 926, which can be configured to receive a portion of the textile material 918. In some embodiments, properties of the gap or the lip in FIG. 9B are different than the corresponding structures in FIG. 9A, based on the top case 924 having a greater width than the top case 904 in FIG. 9A. In some embodiments, there is a gap between the end of the textile material that is fed between the lip 919 and the bottom case 916.

Figure 9C:
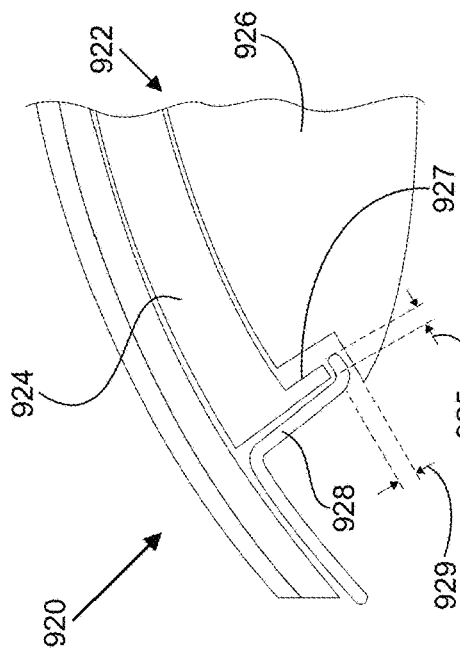

FIG. 9C shows a third example of a band 920 that has a compute core 922. The textile material 928 is wrapped at 90 degrees around the lip 927 of the top case 924 of the compute core 922. In some embodiments, there is a vertical gap 929 between a lower surface of the lip 927 of the compute core 922 and an upper surface of the bottom case 926. In some embodiments, the gap 929 is narrower than the thickness of the textile material 928. In some embodiments, another gap between the inner surface of the lip 927 and the outer surface of the lower case 926 is narrower than the same respective gaps in the example bands shown in FIGS. 9A and 9B, since there is no textile material fed through to that portion of the compute core. In some embodiments, the top case 924 and/or the bottom case 926 include a soft material (e.g., elastomer) such that the top case 924 and the bottom case 926 can be compressed together, which can increase a retention force of the textile material 928 that is fed through the gap 929. In some embodiments, the width of a bond affordance excess (e.g., additional textile material configured to be in the gap between the lip and the outer surface of the bottom case) of the textile material 928 is the same as the width 925 of the lip 927. In some embodiments, the bond affordance excess of the textile material 928 is between 0.6 millimeters and 1.2 millimeters. In some embodiments, the textile material 928 is not fed past the inner edge of the lip 927. In some embodiments, the portion of the textile material 928 is fed through the gap 929 is made of a different material than other portions of the textile material 928.

FIG. 9D shows a fourth example of a band 930 that has a compute core 932. The textile material 938 is reinforced with a polyurethane carrier 937, which can be adhered between an inner surface of the textile material 938 and an outer surface of the lip 939. In some embodiments the polyurethane carrier 937 stabilizes the edge of the lip 939 and allows it to be formed. In the example shown by FIG. 9D, an exterior textile material 931 and an interior textile material 938 are made of the same material (e.g., black textile material that prevents the band from overheating).

In some embodiments, the textile material 938 is reinforced internally with the polyurethane carrier 937 such that the polyurethane carrier 937, in combination with the reinforced portion of the textile material 938 are configured to form an edge that extends into at least a portion of the gap 935. In some embodiments, the edge formed by the textile material 938 and the polyurethane carrier 937 is stabilized through a combination of the thermoplastic backer and laser cutting cauterization. In some embodiments, the thermoplastic backer is configured to sharpen the bend radius of the textile material 938 at or near the edge. In some embodiments, the portion of the textile material 938 that forms the edge is treated so as to minimize the chance of fraying or breakage. In some embodiments, a dimension of the edge formed by the textile material 938 and the polyurethane carrier 937 is dependent on tolerances of laser cutting and/or die cutting manufacturing processes. In some embodiments, the portion of the textile material 938 that forms the edge is hidden by component geometry of the band 930, and/or is encapsulated by one or more coating materials.

Figure 9E:
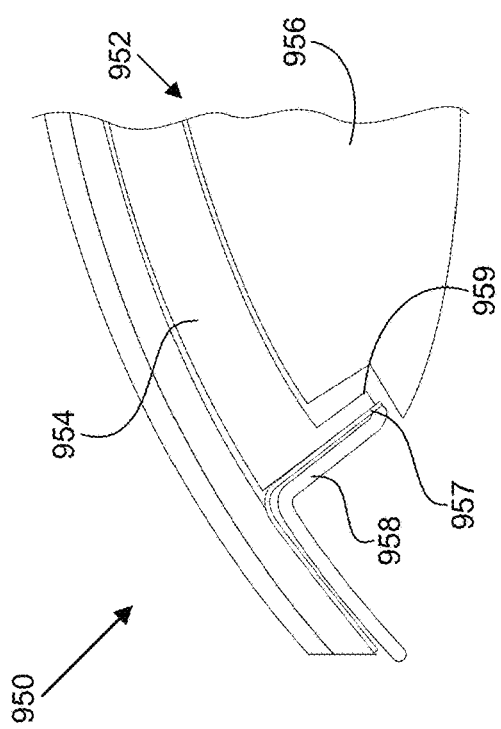

FIG. 9E shows a fifth example of a band 940 that has a compute core 942. The textile material 948 is reinforced with a polyurethane carrier 947, which can be adhered between an inner surface of the textile material 948 and an outer surface of the lip 949. In some embodiments the polyurethane carrier 947 stabilizes the edge of the lip 949 and allows it to be formed. The textile material 948 is thicker and coarser than the textile material 938 in FIG. 9D, in accordance with some embodiments. In some embodiments, any of the components shown and/or discussed with respect to FIG. 9D can be used in the example shown in FIG. 9E.

Figure 9F:
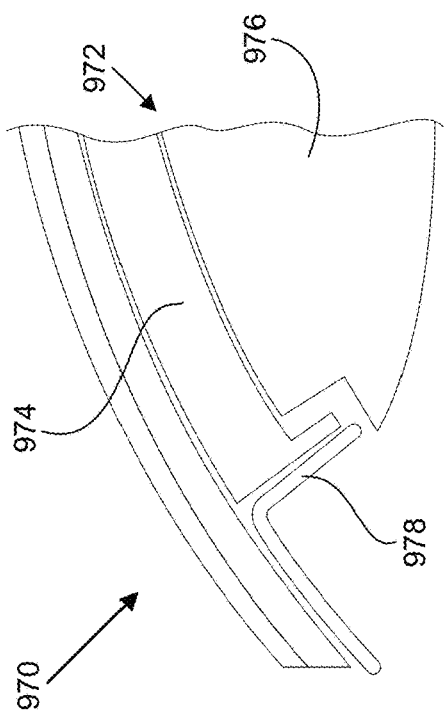

FIG. 9F shows a sixth example of a band 950 that has a compute core 952. The textile material 958 is reinforced with a polyurethane carrier 957, which can be adhered between an inner surface of the textile material 958 and an outer surface of the lip 959. In some embodiments the polyurethane carrier 957 stabilizes the edge of the lip 959 and allows it to be formed. The textile material 958 is thicker and coarser than the textile material 938 and the textile material 948 in FIGS. 9D-9E, in accordance with some embodiments. In some embodiments, any of the components shown and/or discussed with respect to FIGS. 9D and/or 9E can be used in the example shown in FIG. 9F.

Figure 9G:
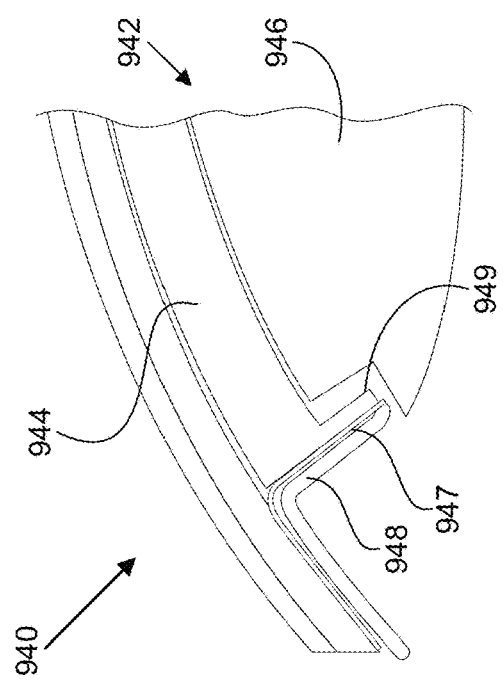

FIG. 9G shows a seventh example of a band 960 that has a compute core 962. The textile material 968 is reinforced at the corner with an inner film layer 969 and an outer film layer 967. In some embodiments, the inner film layer 969 and the outer film layer 967 are configured to sharpen the bend radius of the textile mater 968 at the formed corner. In some embodiments, the portion of the textile material 938 that forms the edge is treated so as to minimize the chance of fraying or breakage. In some embodiments, a dimension of the edge formed by the textile material 968, the inner film layer 969, and the outer film layer 967 is dependent on tolerances of laser cutting and/or die cutting manufacturing processes. In some embodiments, the portion of the textile material 968 that forms the edge is hidden by component geometry of the band 960, and/or is encapsulated by one or more coating materials.

Figure 9H:
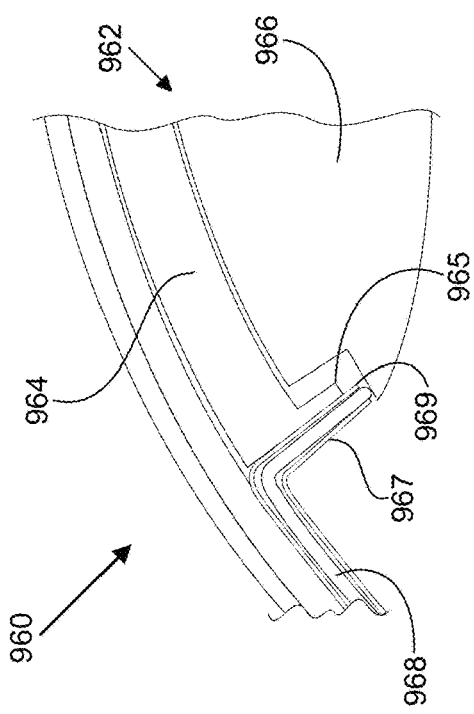

FIG. 9H shows an eighth example of a band 970 that has a compute core 972. The textile material 978 includes a formidable TPU yarn that allows the textile material to be compression-molded around one or more of the top case 974 and the bottom case 976 of the compute core 972.

Figure 9I:
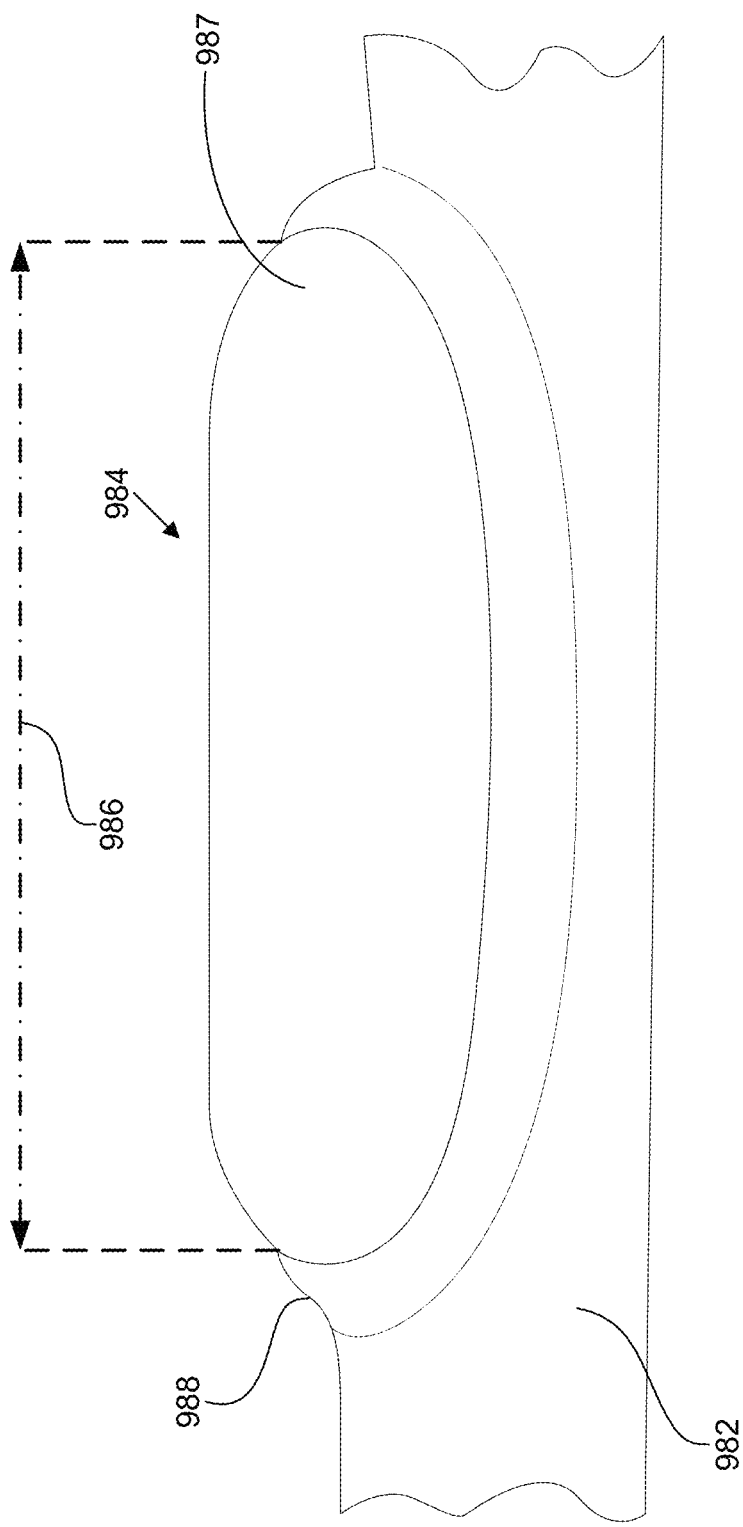

FIG. 9I shows a perspective view of a ninth example of a band 980 that has a compute-core region for receiving a compute core. The band 980 can include some or all of the components of the example bands described with respect to FIGS. 9A-9H. The band 980 includes a compute core region 984 that has an inner width 986. In some embodiments, a compute core (e.g., the compute core 108) is configured to be situated in the compute-core region 984. In some embodiments, the inner width 986 of the compute-core region 984 is configured to be less than the width of a compute core configured to be placed in the compute-core region 984. In some embodiments, the compute-core region is made of flexible material that is configured to stretch or otherwise be deformed while the compute core is being fed through the opening of the compute-core region 984. In some embodiments, there is an outer lip 988 of the of the compute-core region 984 that is made of different material than the textile material 982 surrounding the compute-core region 984. In some embodiments, the compute-core region 984 is configured to seamlessly surround a perimeter of a compute core (which can be configured to process electrical signals for a wearable electronic device, as discussed in more detail herein). In some embodiments, the compute-core region 984 includes a geometrically shaped opening 987.

In some embodiments the outer lip 988 is configured to be angled around the geometrically shaped opening 987 (e.g., angled inwardly), and the angled aspect of the geometrically shaped opening 987 is configured to seamlessly surround a compute core placed inside the geometrically shaped opening 987. In some embodiments the geometrically shaped opening defined by the compute-core region includes a portion of textile material that is angled relative to a first adjacent portion of the geometrically shaped opening within a seam of the compute core. For example, the textile material can define an outer lip around the perimeter of the compute-core region, such that the geometrically shaped opening extends along a vertical dimension of the compute core 108 when it is encased by the geometrically shaped opening of the compute-core region.

FIGS. 10A-10E illustrate other example bands that include a textile-based material with a compute-core region that can surround a compute core, in accordance with some embodiments. Specifically, FIGS. 10A-10E illustrate various methods for tapering a transition region between a rigid portion of the compute core and the band portion (e.g., soft-to-rigid transition zones). The user can experience different visual and physical effects (e.g., look and feel) based on the structure of the transition region between the compute core and the band portion.

In some embodiments, the compute core has a rounded bottom surface and a flat top surface, and the rounded bottom surface is configured to face inward towards a user's wrist, while the flat top surface is configured to face outward away from the wrist of the user. For example, the rounded portions corresponding to the respective compute cores (e.g., a compute core 1004, a compute core 1024, a compute core 1044, a compute core 1064, and a compute core 1084) can be facing downward towards skin of the user when the respective bands are worn by a user. This is just one way that the geometry has been altered for isolation of the specific components described with respect to FIGS. 10A-10E.

In some embodiments, as discussed below, a layer of material of the band portion can be attached to a flat upper surface of the compute core (e.g., the band portion 1006 in FIG. 10A). In some embodiments, respective bands include rigid structures (e.g., a hard plastic plate that extends directly outward from at least one side of the compute core into a length of the band portion). In some embodiments, the rigid material can cause a reduced circumferential strain to be applied to the user's wrist (e.g., a flatter surface profile associated with the region of the wearable electronic device that houses the compute core can cause there to be a flatter angle of the band portion at a connection point between the compute core and the band portion.

Figure 10A:
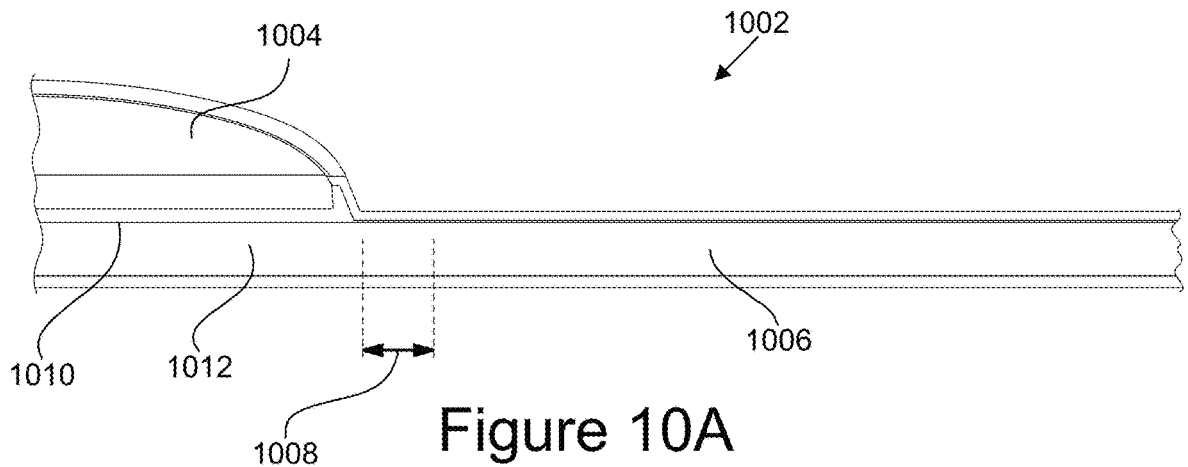
FIGS. 10A-10E illustrate other example bands that include a textile-based material with a compute-core region that can surround a compute core, in accordance with some embodiments.

FIG. 10A illustrates a first example embodiment of a band 1002 (which can be a wearable electronic device). The band 1002 includes a compute core 1004, and a band portion 1006. An exterior surface of the band portion 1006 includes a textile material (e.g., a textile-based material that also includes thermoplastic). In some embodiments, the same textile material surrounds the band portion 1006 and the compute core 1004. In some embodiments, an exterior surface of the compute core 1004 includes a different textile material than the material that surrounds the band portion 1004. The band portion 1006 also includes an inner material, which can be textile material. In some embodiments, the inner material of the band portion 1006 includes elastomer material. In some embodiments, there can be a transition zone 1008 between an outer edge of the compute core 1004 and a portion of the band portion 1006 that will be in contact with skin of the user when the band 1002 is worn by a user. The width of the transition zone 1008 can be based, at least in part, on the thickness of an overlapping portion 1012 of the band portion 1006 that is adjacent to the top surface 1010 of the compute core 1004, in accordance with some embodiments. In some embodiments, the thickness of the overlapping portion 1012 of the band portion 1006 can be different than the thickness of the band portion 1006 at other sections of the band portion's length. In some embodiments, the material of the overlapping portion 1012 and/or the portion of the band portion 1006 that coincides with the transition zone 1008 can be different than the material of other sections of the band portion 1006. In some embodiments, the volume of the compute core 1004 can be smaller than the compute cores of other compute cores described in FIGS. 10B-10E to account for the width of the overlapping portion 1012.

Figure 10B:
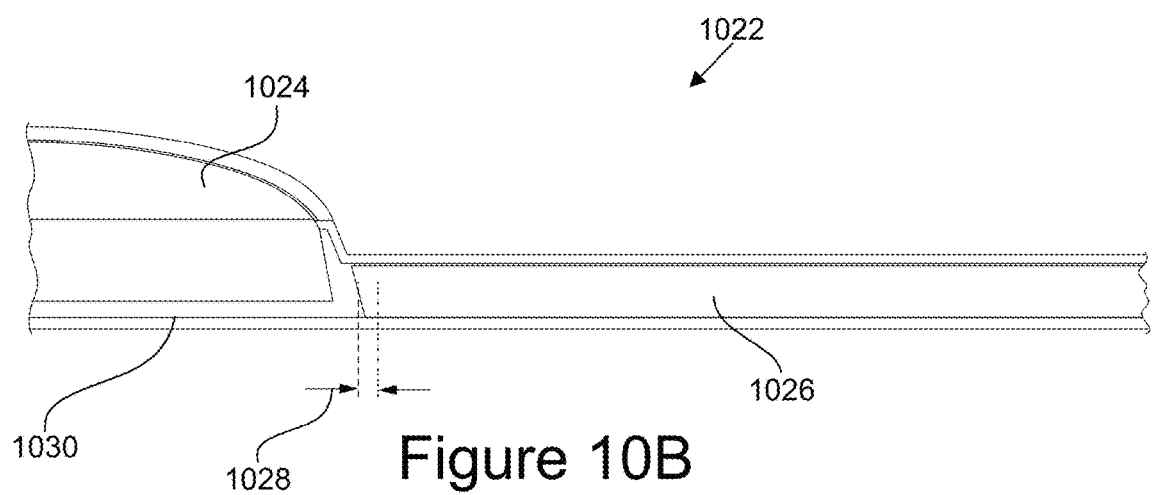

FIG. 10B illustrates a second example embodiment of a band 1022. The band 1022 includes a compute core 1024, and a band portion 1026. Exterior surfaces of the compute core 1024 and the band portion 1026 include textile material, which can be the same or different textile material than the textile material shown in FIG. 10A. There is no overlapping portion of the band portion 1026 in accordance with some embodiments (e.g., the only portion of the band that is adjacent to the top surface 1030 of the compute core 1024 is an outer textile material). In some embodiments, the textile portion of the band 1022 that is adjacent to the top surface 1030 of the compute core 1024 in FIG. 10B is made of a more durable material than other portions of the textile material to account for the proximity to the top surface 1030. In some embodiments, there is a transition zone 1028 between an outer edge of the compute core 1024 and a portion of the band portion 1026 that will be in contact with skin of the user when the band 1022 is worn by a user. In some embodiments, the width of the transition zone 1028 is substantially less than the transition zone 1008 of the band 1002. In some embodiments, the volume of the compute core 1024 is greater than the volume of the compute core 1004.

Figure 10C:
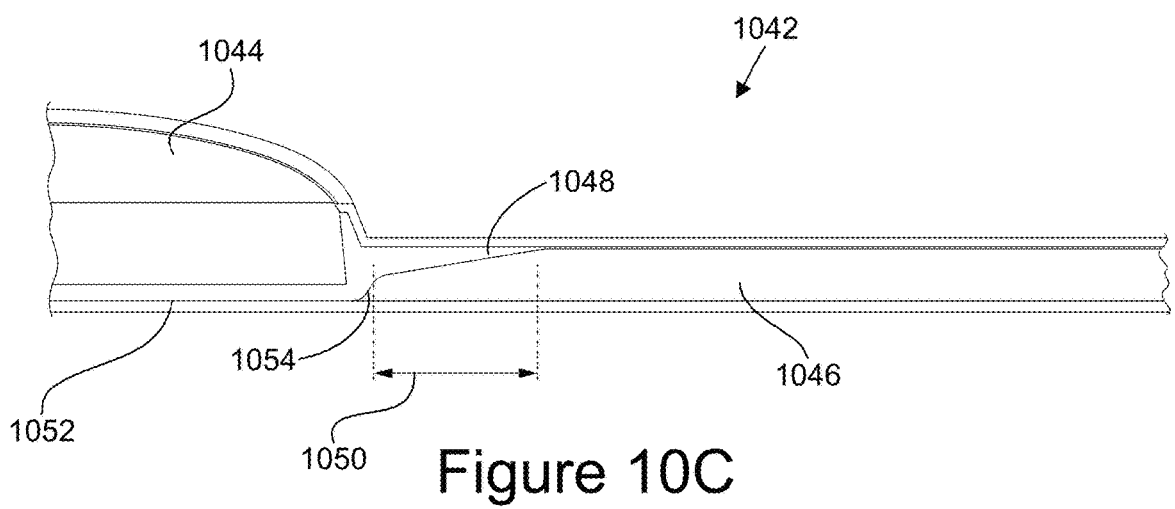

FIG. 10C illustrates a third example embodiment of a band 1042. The band 1042 includes a compute core 1044, a band portion 1046, and a tapered wing 1048 that extends from the compute core 1044 into the transition zone 1050 of the band portion 1046. In some embodiments, the top surface 1052 of the compute core 1044 includes a beveled edge 1054 that extends downward to a starting depth of the tapered wing 1048. In some embodiments, the width of the transition zone corresponds to one or more sides of the tapered wing 1048.

Figure 10D:
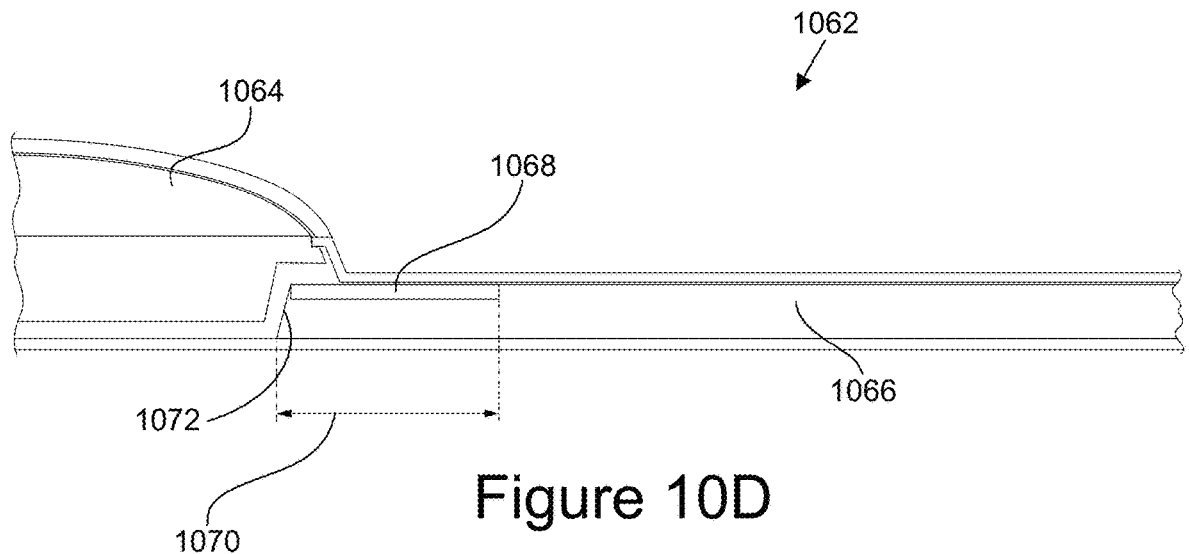

FIG. 10D illustrates a fourth example embodiment of a band 1062. The band 1062 includes a compute core 1064, a band portion 1066, and a panel 1068 that extends from the compute core 1064 into the transition zone 1070 of the band portion 1066. In some embodiments, a portion of the panel 1068 extends under an overhanging portion of the outer edge of the compute core 1064. In some embodiments, the panel 1068 is made of a rigid material (e.g., hard plastic, stainless steel, etc.). In some embodiments, the panel 1068 is made of a coarse fiber material (e.g., scrim). In some embodiments, the outer edge of the compute core 1064 includes an angled edge 1072 that extends upward to the overhanging portion of the compute core 1064. In some embodiments, the width of the transition zone 1070 corresponds to one or more sides of the panel 1068.

Figure 10E:
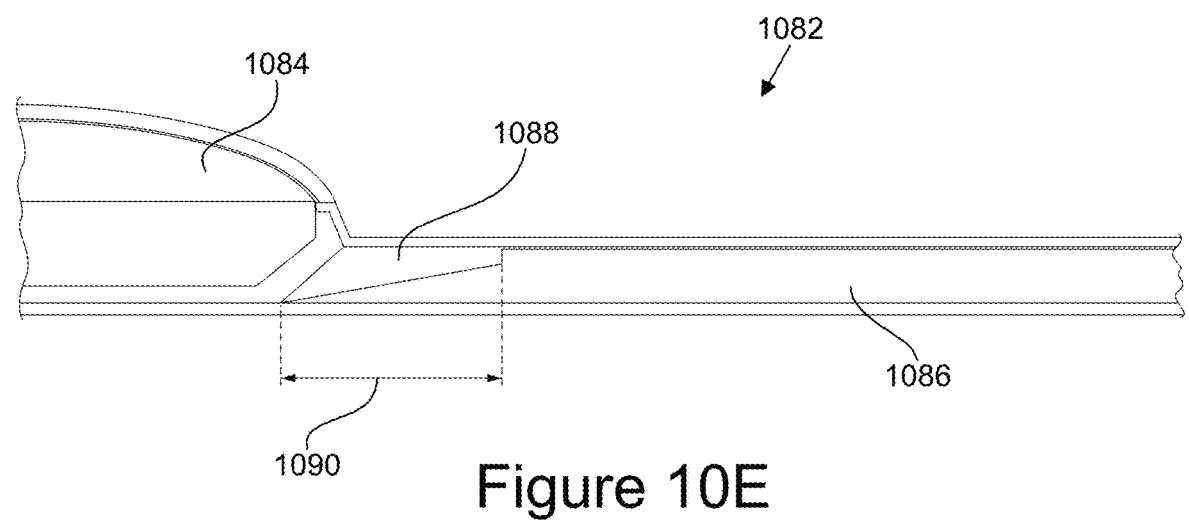

FIG. 10E illustrates a fifth example embodiment of a band 1082. The band 1082 includes a compute core 1084, a band portion 1066, and an elastomeric wing 1090 that extends into the transition zone 1090 of the band portion 1086. In some embodiments, the elastomeric wing 1090 is co-molded with one or more of the compute core 1084 or the band portion 1086. In some embodiments, the elastomeric wing 1088 is joined (e.g., via molding, soldering, adhesive, etc.) with the band portion 1086 during the manufacturing and/or assembly of the band 1082.

One of ordinary skill in the art will understand that the same structures described with respect to FIGS. 10A-10E (e.g., the respective components in the transition zones of the respective bands) can be identical to other components on the other outer edge of the respective compute core.

Figure 11A:
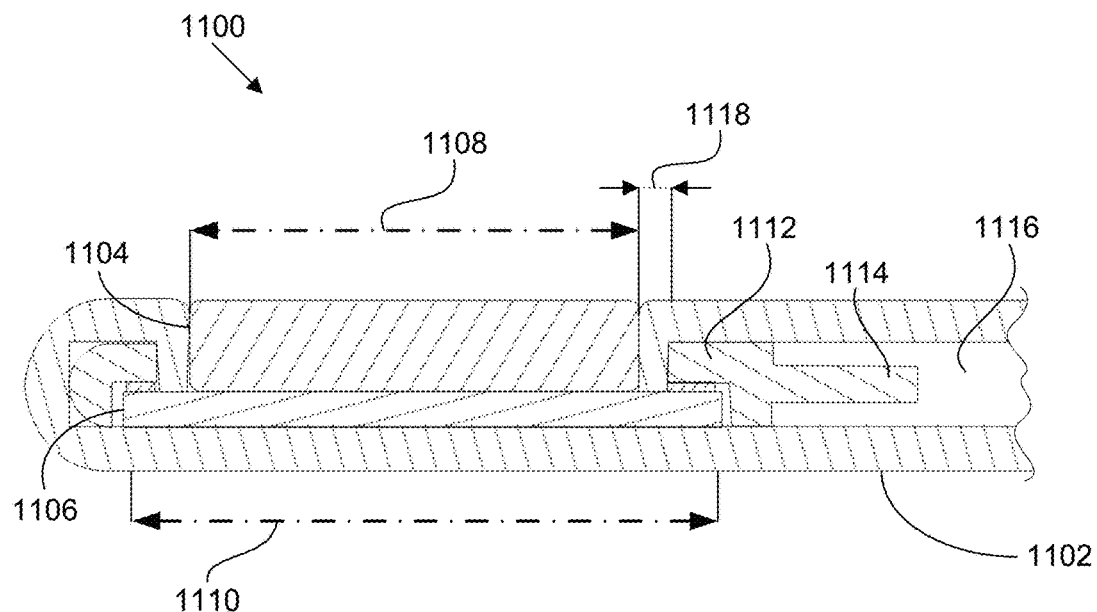
FIGS. 11A-11B illustrate fastening components integrated into a band of an example wearable electronic device, in accordance with some embodiments.
Figure 11B:
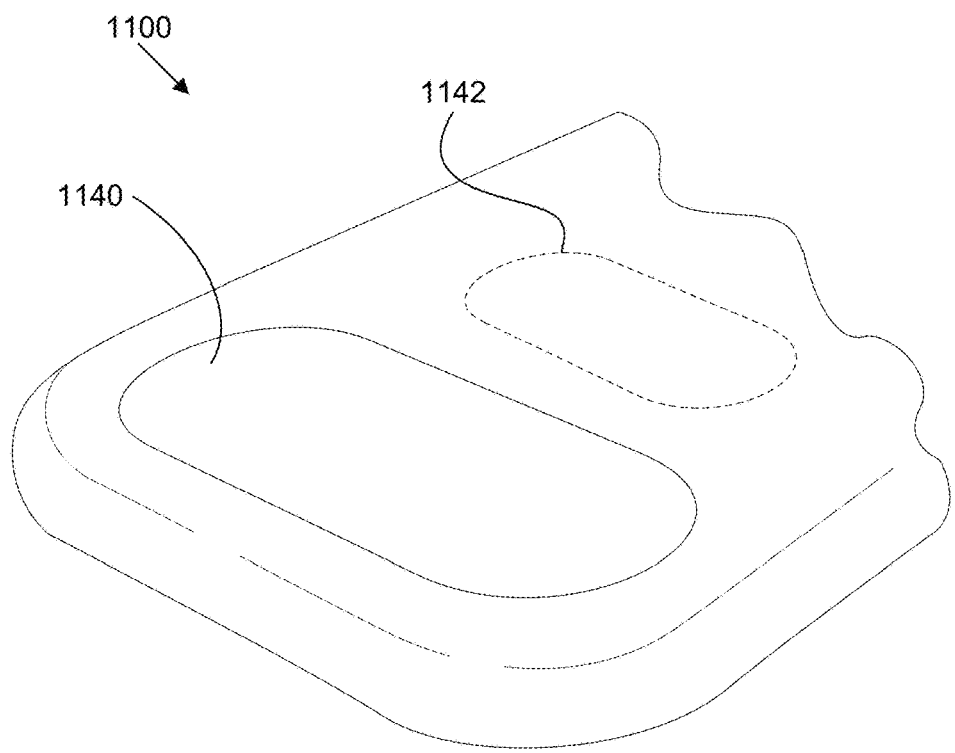

FIGS. 11A-11B illustrate fastening components integrated into a band of a band portion 1100 of an example wearable electronic device, in accordance with some embodiments. In some embodiments, FIG. 11A illustrates a cross-sectional side view of a distal end of a band portion of a wearable electronic device. In some embodiments, the band portion 1102 does not include any electronic components. As described herein, electronic components is meant to exclude magnetic metal materials that are not connected to a separate voltage source or current source.

In some embodiments, the band portion 1102 includes a magnet 1104, which can be an N52 grade rigid magnet. In some embodiments, the magnet 1104 is coated in epoxy. In some embodiments, the epoxy coating is between 5 and thirty micrometers thick. In some embodiments, the magnet is anodized to match the color of the band.

In some embodiments, the magnet 1104 is coupled with a stamped rear cover 1106. In some embodiments, the stamped rear cover 1106 is made of 1018 cold-rolled steel. In some embodiments, the stamped rear cover 1106 has an outer perimeter 1110 that extends beyond the outer perimeter 1108 of the magnet 1104. In some embodiments, the outer perimeter 1110 extends beyond the outer perimeter 1108 by a distance of at least five millimeters. In some embodiments, a bottom surface of the magnet 1104 is adhered to a top surface of the stamped rear cover 1106 with a pressure-sensitive adhesive (e.g., Tesa 75815 double-sided tape). In some embodiments, the adhesive is waterproof and/or shock-resistant.

In some embodiments, the magnet 1104 and/or the stamped rear cover 1106 are surrounded by a molded frame 1112. In some embodiments, the molded frame 1112 is made of PC or ABS material. In some embodiments, the molded frame 1112 includes a flange 1114 that extends inward towards a core 1116 of the band portion 1102. In some embodiments, the core 1116 of the band portion 1102 includes a soft elastomer material that is configured to accommodate the flange 1114 of the molded frame 1112 when it is extended into the core of the band portion. In some embodiments, while the magnet 1104 is surrounded by the molded frame 1112 there is a textile insertion gap 1118 between an outer edge of the magnet 1104 and an inner surface the molded frame 1112, such that a textile material can be inserted between the outer edge of the magnet 1104 and the inner surface of the molded frame.

FIG. 11B shows a perspective view of the band portion 1100. In some embodiments, as shown in FIG. 11B, there is a textured film or coating 1140 that covers the magnet 1104 shown in FIG. 11A. In some embodiments there is a first band portion that includes a FPC (e.g., the FPC 800 in FIGS. 8A-8G). And there is a second band portion that can be an example of the band portion 1100. The first band portion can have a cinch structure (e.g., the cinch structure 200 in FIG. 2A). And the second band portion can be fed through the cinch structure, such that the magnet 1104 can be attached to an outer surface of the first band portion. In some embodiments, the first band portion can have another magnet, which can be flexible, and can extend along a major dimension of the first band portion. In some embodiments, there can be another magnet 1142 along the band portion 1100, which can be used to form a supplemental connection with a second band portion.

FIGS. 12A-12E illustrate a method of manufacturing a fastening component of a wearable electronic device 1200 (which may include some or all of the components of the wearable electronic device 100 shown in FIGS. 1A to 1C, in accordance with some embodiments. In some embodiments, the fastening component of the wearable electronic device 1200 is formed using a terminating end of a band portion (e.g., of the band portion 102 that does not include any electronic components). In some embodiments, the fastening component is configured to couple with a tapered end of a respective band portion of the wearable electronic device 1200.

Figure 12A:
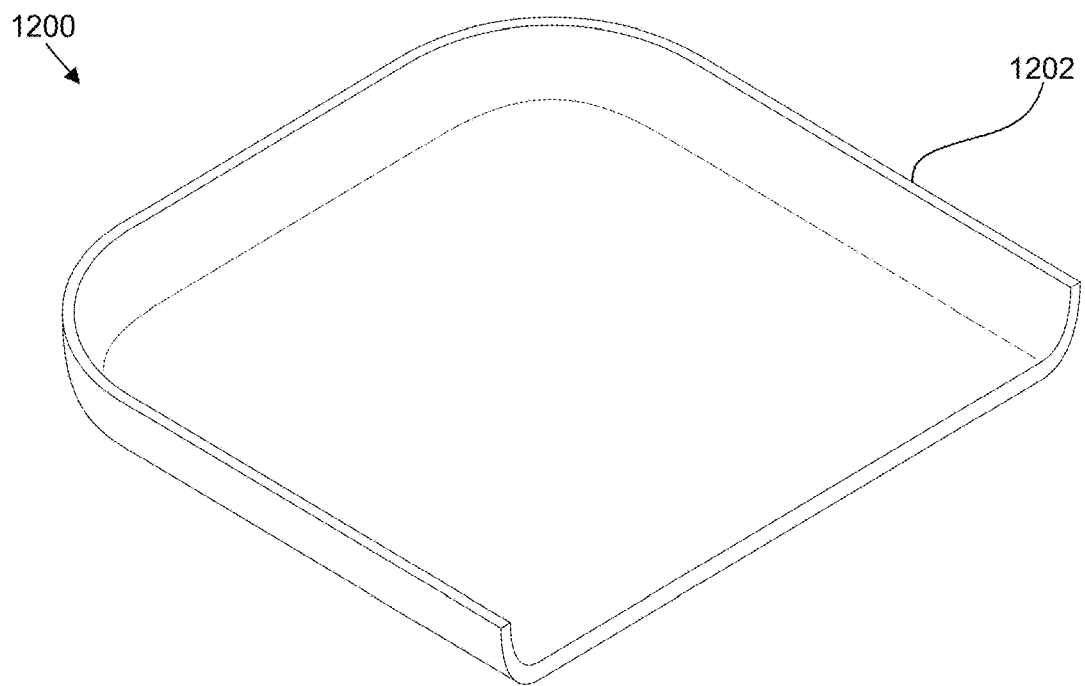
FIGS. 12A-12E illustrate a method of manufacturing a fastening component of an example wearable electronic device, in accordance with some embodiments.

FIG. 12A illustrates an example rear cover 1202 of a magnetic distal end of a band portion (e.g., the band portion 102 in FIG. 1A; the band portion 1100 in FIGS. 11A-11B, etc.). In some embodiments, a pressure sensitive adhesive is applied to an inner surface of the rear cover 1202, the pressure sensitive adhesive being configured to couple with a magnet frame.

Figure 12B:
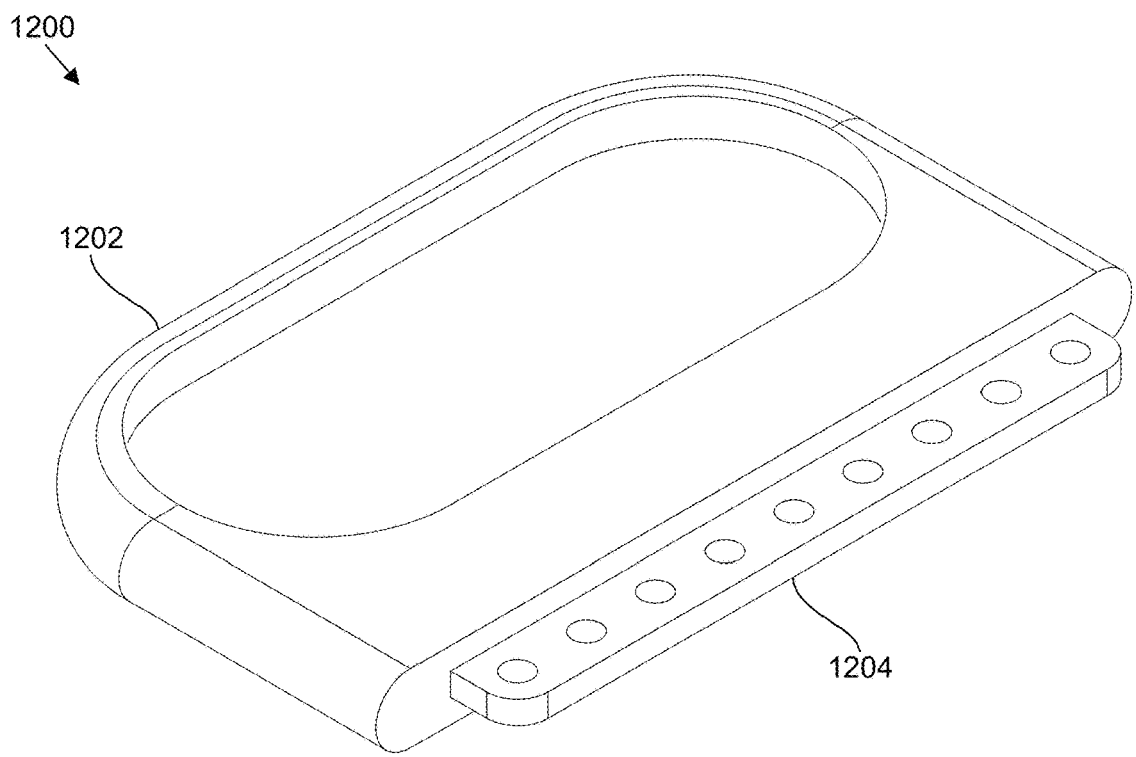

FIG. 12B illustrates a magnet frame 1204 being coupled with the rear cover 1202 via a pressure sensitive adhesive. In some embodiments, the pressure sensitive adhesive has two lining covers, one on either side of the adhesive. A first lining cover is taken off of the bottom side of the pressure sensitive adhesive when it is pressed against the rear cover. In some embodiments, the pressure sensitive adhesive is heat resistant, such that the material properties of the pressure sensitive adhesive are not affected by subsequent molding steps involving the fastening component and/or a wearable electronic device that it is molded to (e.g., the wearable electronic device 100 in FIGS. 1A-1C). In some embodiments, the magnet frame 1204 includes one or molding holes configured to create a stronger coupling with a band portion that is made of meltable elastomer material.

Figure 12C:
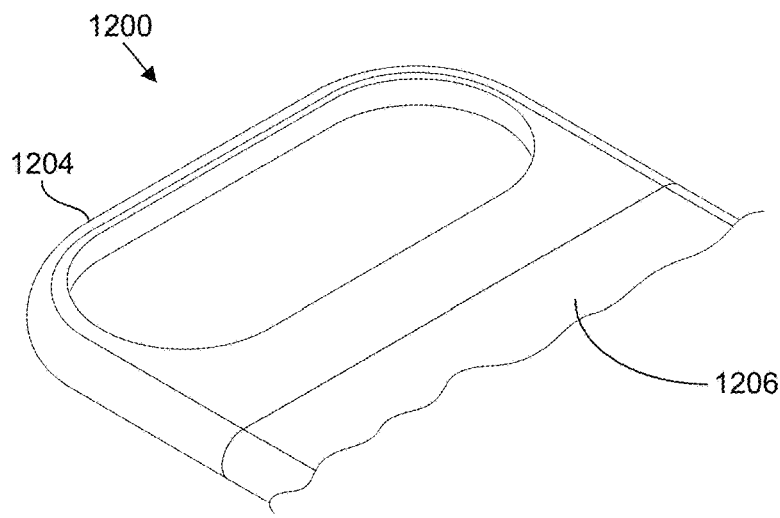

FIG. 12C illustrates the magnet frame 1204 and the rear cover 1202 being molded to a distal end of a band portion 1206. In some embodiments, the band portion 1206 includes some or all of the components of the band portion 102 in FIGS. 1A-1C.

Figure 12D:
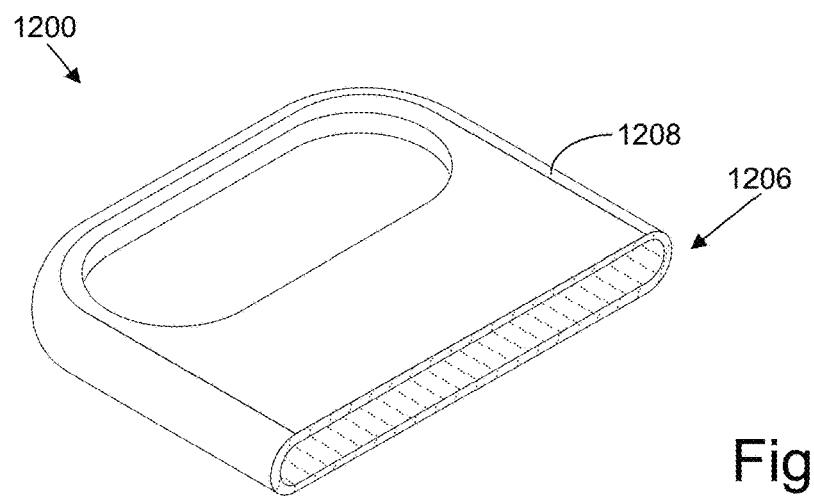

FIG. 12D illustrates a layer of textile material 1208 being applied over the molded combination of the rear cover 1202, the magnet frame 1204 (which is partially encased by the layer of textile material 1208), and the band portion 1206. In some embodiments, the textile material is the same textile material as one or more of the textile materials described with respect FIGS. 9A-9I. In some embodiments, the textile material 1208 is heat-treatable, such that applying heat to the textile material 1208 causes it to be adhered to the magnet frame 1204 and/or the band portion 1206.

Figure 12E:
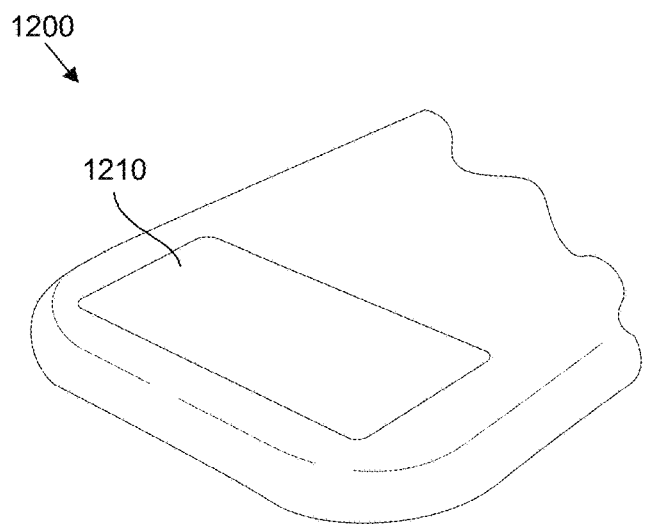

FIG. 12E illustrates the fastening component 1200, which is encased in the layer of textile material 1208, after a magnet 1210 is placed into the magnet frame 1204. In some embodiments, the pressure sensitive adhesive has two lining covers as described with respect to FIG. 12B, and a top lining cover is removed before the magnet 1210 is placed into the magnet frame 1204, such that the magnet 1210 can be pressed into the pressure sensitive adhesive attached to the rear cover 1202 to secure the magnet 1210 into the magnet frame 1204. In some embodiments, an epoxy resin coating is applied over the top surface of the magnet 1210, such that the color of the outer surface of the magnet matches the color of the textile material 1208.

Example System-Level Block Diagrams

Figure 13:
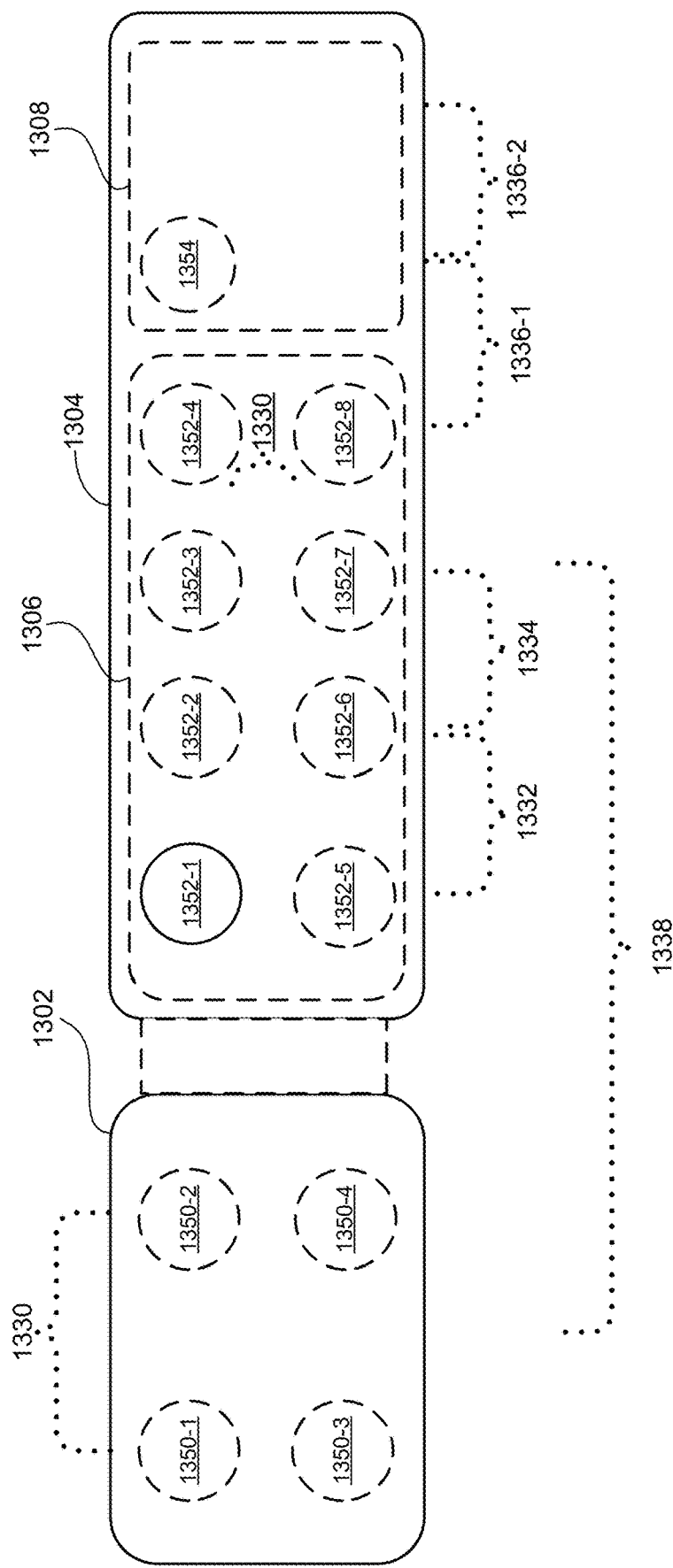
FIG. 13 illustrates a schematic view of an example wearable electronic device that includes a sensor topology, in accordance with some embodiments.

FIG. 13 illustrates a schematic view of an example wearable electronic device (e.g., the wearable electronic device 100) that includes a sensor topology, in accordance with some embodiments.

FIG. 13 illustrates a wearable electronic device 1300 that includes a compute core 1302, and a band 1304. In some embodiments, the band includes two or more band portions (e.g., the band portion 102 and the band portion 104 in FIGS. 1A-1C).

In some embodiments, the compute core 1302 is integrally formed with the band 1304. In some embodiments, the compute core 1302 can be detachably coupled to the band 1304 such that it can be removed (e.g., by pivotably rotating the compute core 1302 relative to an angle of the band 1304, or a portion thereof). The band 1304 can have two or more band portions (e.g., a first band portion 1306, a second band portion 1308, etc.).

The compute core 1302 and the band 1304 together form a unitary structure that includes one or more electrodes and/or sensors (e.g., a first set of electrodes 1350-1-1350-4, a second set of electrodes 1352-1-1352-8, an sensor contact 1354, etc.). Some of the electrodes can be used to detect neuromuscular signals. In some embodiments, the band 1304 includes sensors in more than one sensor distributed in different locations of the wearable electronic device 1300. In some embodiments a same sensor corresponds to two respective electrodes (e.g., the electrode 1352-1 and the electrode 1352-5) that are attached to different sides of a carrier component (e.g., the carrier component 502 in FIGS. 5A-5C).

The wearable electronic device 1300 can have channels between one or more of the electrodes 1350-1-1350-4 and/or between the sensor-contacts 1352-1-1352-8 and/or between the sensor contact 1354. In some embodiments, there is a common channel length, and there is a plurality of channels of the common channel width. For example, 1332, 1334, and/or 1336-1 can be associated with channels that have a common channel width for band type sensors. In some embodiments, the common channel width is used to reduce noise, prevent damage, and/or define a circumferential shape of the wearable electronic device 1300. In some embodiments there is a channel width for band type sensors, and another channel width for sensors on the compute core 1302 (e.g., a channel width 1330 between the sensors 1350-1 and 1350-2).

In some embodiments, any of the differences in distances between respective sensors shown in FIG. 13 can be dependent on a discrete sizing of the wearable electronic device (e.g., small, medium, large, etc.). In some embodiments, some, or all of the differences in distances between respective sensors shown in FIG. 13 can be independent of a discrete sizing of the wearable electronic device. For example, in some embodiments, the distance 1332 between respective sensor-contacts 1352-5 and 1352-6 is a fixed distance that exists between all sensor-contacts of the respective type of the sensor contacts 1352-5 and 1352-6, and the distance 1338 between the mid-lines of the respective compute core 1302 and the band 1304 is based on a discrete sizing of the wearable electronic device. In some embodiments, one or more of the neuromuscular-signal-sensing electrodes can be molded onto a single structure (e.g., the structure shown in the method 500 shown in FIGS. 5A-5C). In some embodiments, the molded structure defines the channel width (e.g., the channel width 1330) between at least two respective sensor-contacts of the band 1304. In some embodiments, the separation distance between two electrodes attached to same carrier component is adjustable, by sliding one or both of the electrodes along the longest dimension of the carrier component.

Figure 14:
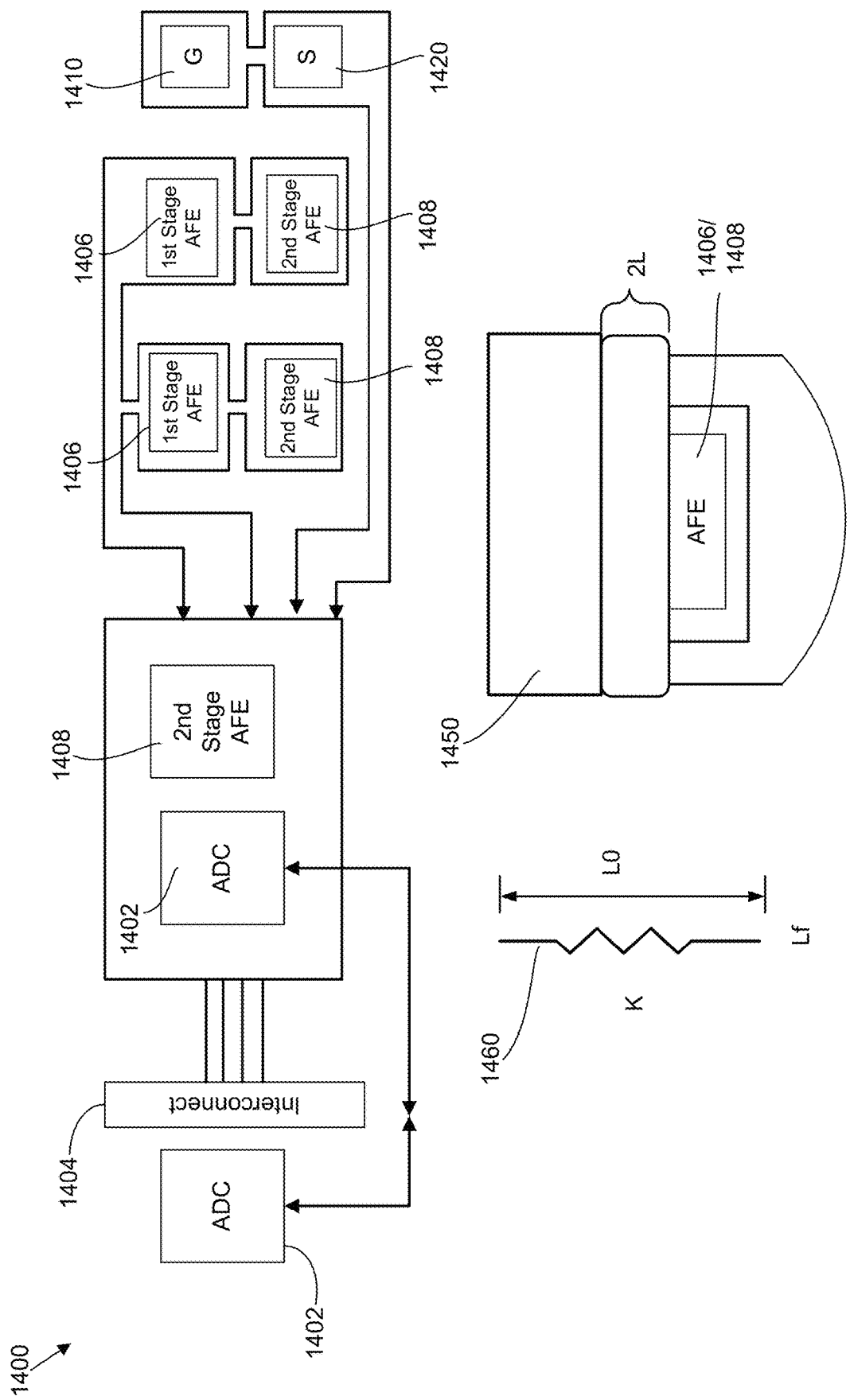
FIG. 14 illustrates an example electromechanical architecture used for detecting biopotential signals, in accordance with some embodiments.

FIG. 14 illustrates an example electromechanical architecture 1400 used for detecting neuromuscular signals, in accordance with some embodiments. FIG. 14 includes one or more analog-to digital converters (ADCs) 1402, an interconnect 1404, one or more first stage AFEs 1406, one or more second stage AFEs 1408, a ground electrode 1410, and a shield electrode 1420. In some embodiments, the one or more first stage AFEs 1406 and the one or more second stage AFEs 1408 are positioned along the bottom of the compute core 1450 and/or along the wearable structure of the wearable electronic device (e.g., the wearable electronic device shown in FIGS. 1A-1C). In some embodiments, one or more corresponding ground electrodes 1410 and one or more corresponding shield electrodes 1420 are electrically coupled via a FPC (e.g., the FPC 800 in FIGS. 8A-8G).

FIG. 14 shows a spring structure 1460. In some embodiments, the spring structure 1460 has a length L0 that is approximately three millimeters (e.g., within +/−0.2-0.3 millimeters). In some embodiments, the spring structure 1460 has a free length (Lf) of two to three millimeters. In some embodiments, the spring structure has a spring rate (K) of 5 g/mm. In some embodiments, the spring structure mimics the structure of a pogo pin (60 g/mm) while also reducing the spring rate to 5 g/mm. A spring rate (K) of 5 g/mm provides an ideal level of comfort and pressure that allows users to wear the wearable device for extended periods of time (e.g., 5 hours, 8 hours, a full day, overnight, etc.). In some embodiments, the spring structure is embedded within the compute core 1450 and configured to allow the one or more first stage AFEs 1406 and the one or more second stage AFEs 1408 move in the Z direction (perpendicular to the bottom surface of the compute core 1450 coupled the first and second stage AFEs 1406 and 1408). In some embodiments, respective spring structure 1460 are coupled between each of the first and second stage AFEs 1406 and 1408 and the bottom surface of the compute core

1450. In some embodiments, respective spring structures 1460 are coupled between each of the first and second stage AFEs 1406 and 1408 and the interior surface of the wearable electronic device (e.g., wearable structure; FIGS. 1A-1C). In this way, the first and second stage AFEs 1406 and 1408 can move in a Z direction at each of their respective positions along the wearable structure. In some embodiments, one or more spring structures 1460 can be embedded within one or more neuromuscular signal-sensing structures distributed along a band portion of the wearable electronic device 1400. In some embodiments, one or more spring structures 1460 are configured to cause electrodes on a respective biopotential-signal sensing structure (e.g., the biopotential-signal sensing structure shown in FIGS. 5A-5C) to protrude by at least a certain depth into the skin of a user wearing the wearable electronic device 100. In some embodiments, a respective spring structure 1460 is coupled between each of the first and second stage AFEs 1460 and 1408 and the interior surface of the wearable electronic device 1400 (e.g., the wearable electronic device 100 shown in FIGS. 1A-1C). In this way, the first and second stage AFEs 1406 and 1408 can move in a Z-direction at each of their respective positions along the wearable structure.

Figure 15A:
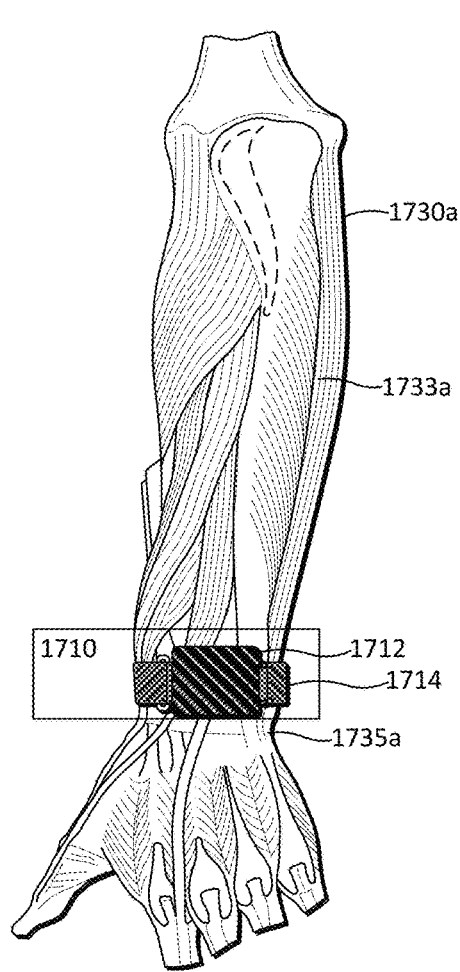
FIGS. 15A-15C illustrate a wearable electronic device for sensing biopotential signals using biopotential-signal sensing structures, in accordance with some embodiments.
Figure 15B:
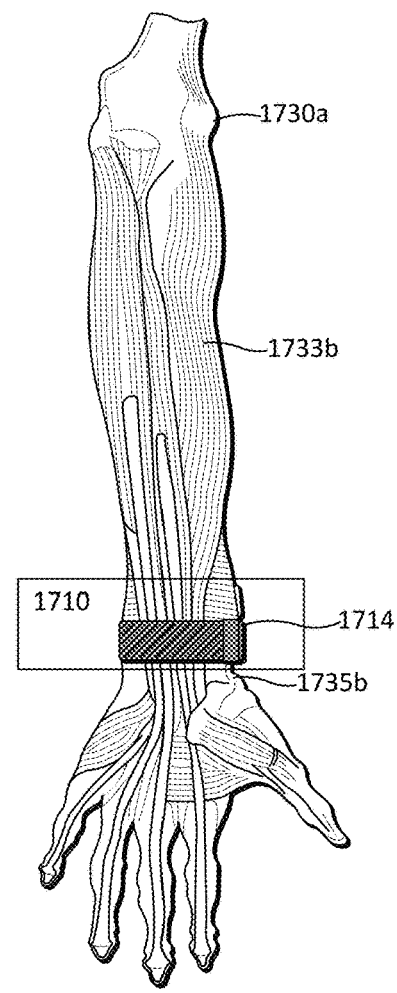
Figure 15C:
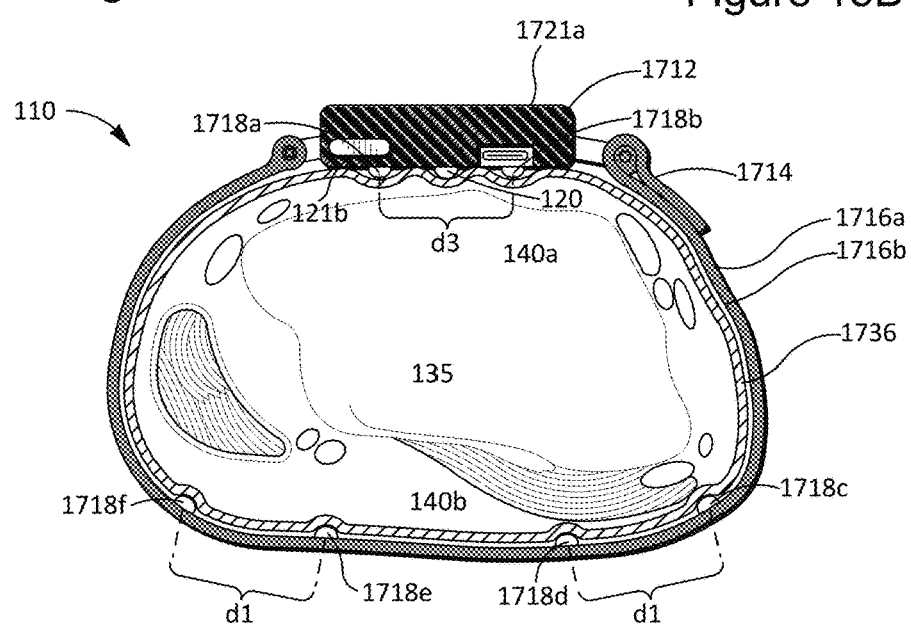

FIGS. 15A-15C illustrate a wearable electronic device 1710 for sensing neuromuscular signals using neuromuscular signal-sensing structure, in accordance with some embodiments. The wearable electronic device 1710 includes a wearable structure. The wearable structure can include one or more band portions, a compute core 1712, a cinch structure, and one or more biopotential-signal sensing structures, where one or more of the aforementioned components of the wearable electronic device can include a textile material that is configured and arranged to encapsulate one or more components and/or sub-components of the wearable electronic device. In some embodiments, the compute core is housed inside of a rigid, dome-shaped structure that can include a top case and a bottom case.

The wearable structure has an interior surface and an exterior surface (which can include an interior band surface 1716*b*, as well as an interior compute core surface 1721*b* of the compute core 1712) and an exterior surface (which can include an exterior band surface 1716*a*, as well as an exterior compute core surface 1721*a* of the compute core 1712). The interior surface, including the interior band surface 1716*b* and the interior compute core surface 1721*b*, is configured to contact a user's skin 1736 when the wearable device 1710 is donned (e.g., put on to be worn) by the user (e.g., on the user's arm as shown in the dorsal arm view 1730*a* and the ventral arm view 1730*b*, shown in FIGS. 15A and 15B). In some embodiments, the wearable structure is configured to wrap around a user's wrist (e.g., the dorsal wrist-portion 1735*a* and the ventral wrist portion 1735*b*, shown in FIGS. 15A and 15B). In some embodiments, the wearable structure has a fixed size (e.g., a fixed circumferential size when the wearable structure surrounds the user's wrist after being donned) such that respective locations of the pairs of sensors over the muscle groups (e.g., dorsal muscle group and the ventral muscle group) is substantially constant or the same for different users each having substantially constant or the same for different users. As described with respect to the positions of the biopotential-signal sensing structures, locations being substantially constant means, in some embodiments, within +/−1-2 millimeters in positional shift from one user's wrist to another, or from one example wearable electronic device 1710 to another, etc. In some embodiments, example wearable electronic devices 1710 can be provided in a set of discrete sizes, each with a fixed circumferential size. In some embodiments, the wearable electronic device 1710 can be manufactured to have, for example, three or four fixed sizes, each associated with a different range of wrist sizes of respective users. In some embodiments, the circumferential size of the wearable electronic device 1710 is adjustable (e.g., via a cinch structure, such as the cinch structure described in FIGS. 2A-3B).

Figure 16A:
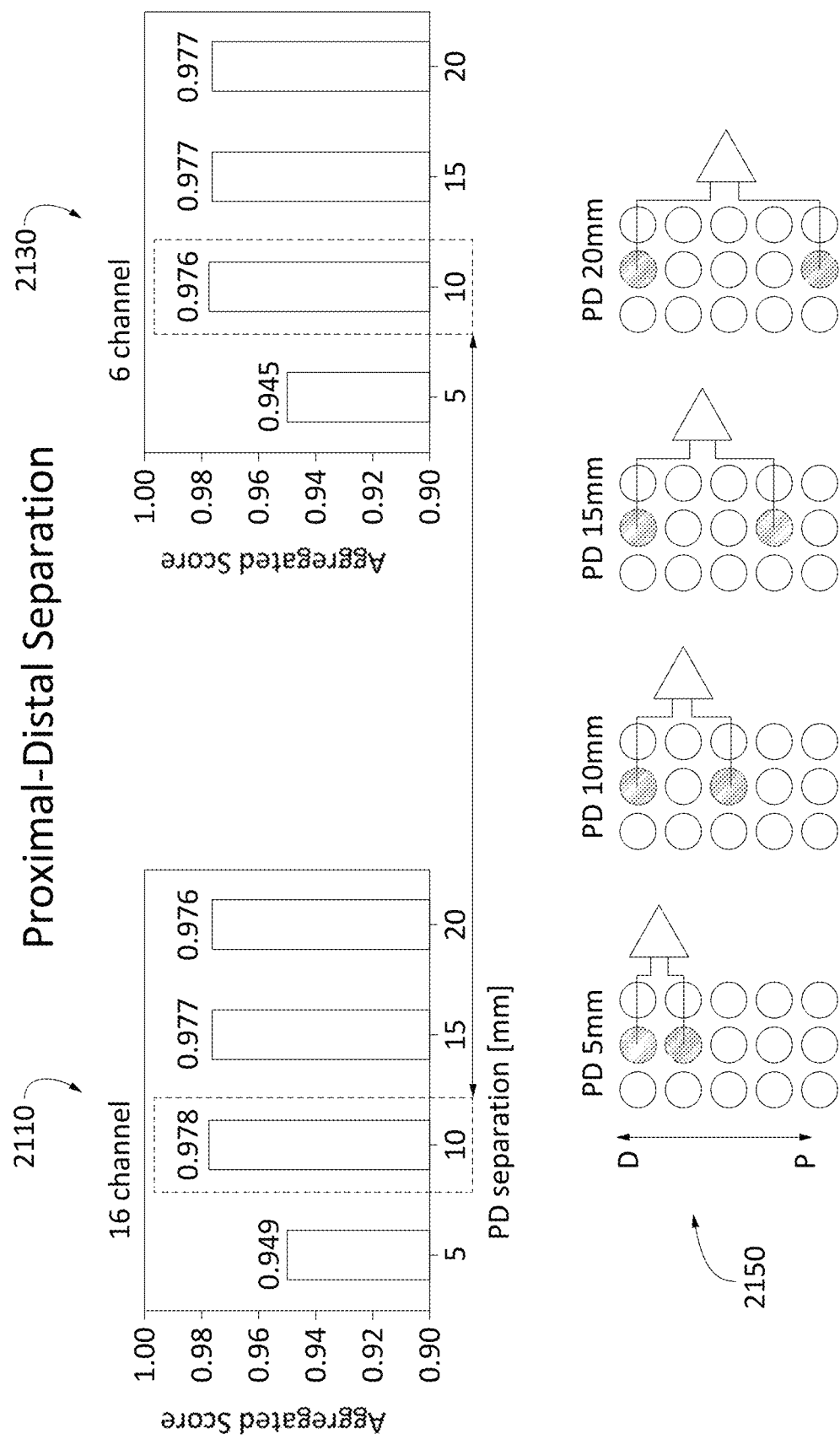
FIGS. 16A and 16B illustrate examples of minimum separation distances between sensors in a respective set of two or more sensors for accurately sensing biopotential signals, in accordance with some embodiments.
Figure 16B:
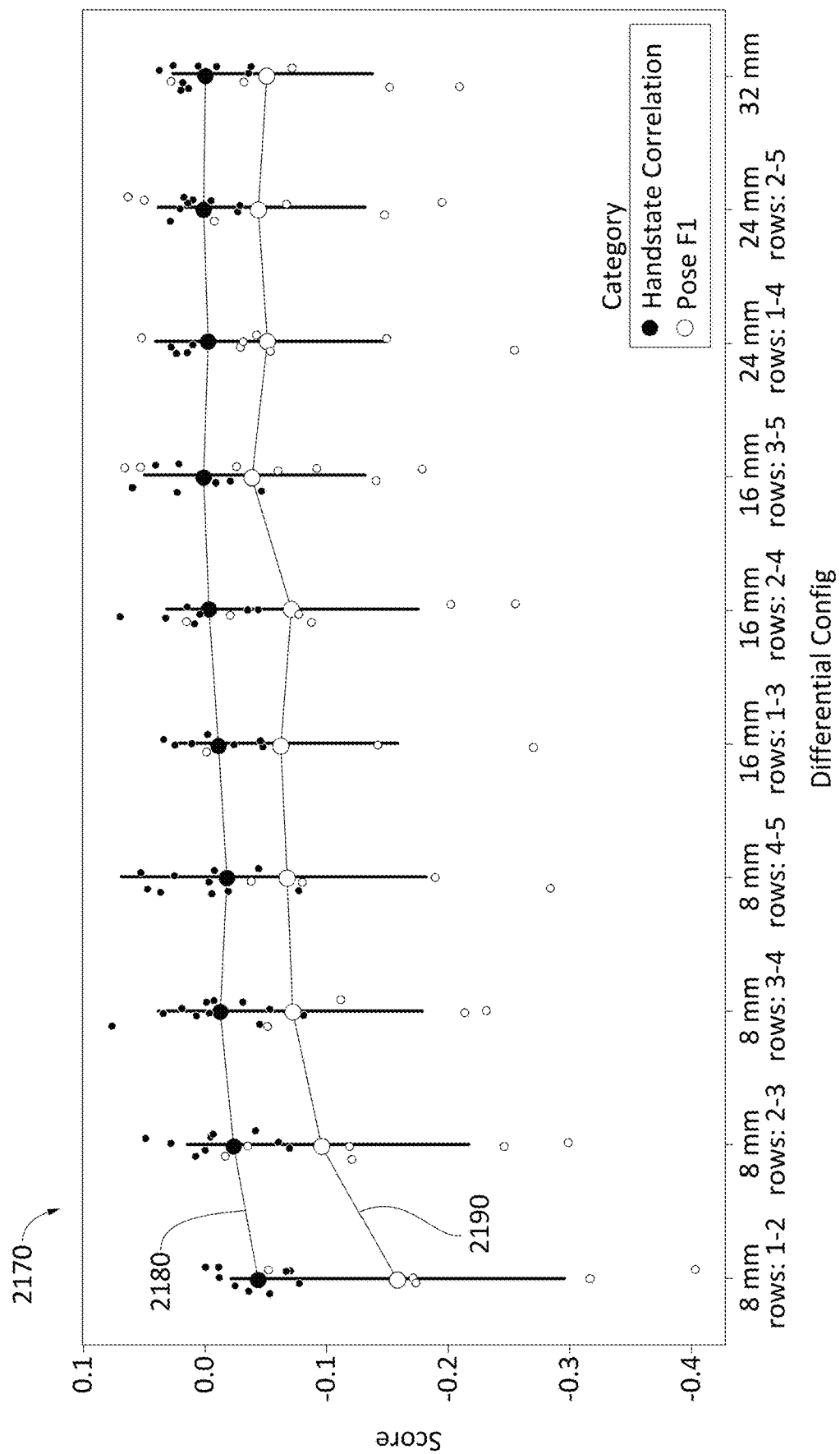

FIGS. 16A and 16B illustrate the minimum separation distance d2 between the sensors in a respective pair of pairs of sensors (which can be any of the distances discussed with respect to the EMG topology of the wearable electronic device 1300 in FIG. 13 (any of the distances 1332, 1334, 1336-1, 1336-2, etc.)) for accurately sensing neuromuscular signals. FIG. 16A includes a first plot 510 showing the performance of sensors (or electrodes, such as the biopotential-signal-sensing contact points discussed in FIGS. 5A-5C) of a respective pair of sensors at different separation distances d2 in a 16-channel set of the wearable electronic device 100, a second plot 2130 showing the performance of sensors of a respective pair of sensors at different separation distances d2 in a six-channel wearable device (e.g., an example of the wearable electronic device 100), and a proximal-distal diagram 550 showing a visual representation of the separation distances between sensors of a respective pair of sensors.

As shown in the first plot 2110, by placing the sensors less than 10 millimeters apart in a wearable electronic device 100 with 16 channels (or 16 pairs of sensors) the user's hand gestures are accurately sensed slightly less than 95% of the time (e.g., 94.9% of the time). By placing the sensors 10 millimeters apart in the wearable electronic device 100 with 16 channels the user's hand gestures are accurately sensed more than 95% of the time (e.g., 97.8% of the time). By placing the sensors 15 millimeters apart in the wearable electronic device 100 with 16 channels the user's hand gestures are accurately sensed more than 95% of the time (e.g., 97.7% of the time). By placing the sensors 20 millimeters apart in the wearable electronic device 100 with 16 channels the user's hand gestures are accurately sensed more than 95% of the time (e.g., 97.6% of the time).

Similarly, as shown in the second plot 2130, by placing the sensors less than ten millimeters apart in a wearable electronic device 100 with six channels (or six pairs of sensors) the user's hand gestures are accurately sensed slightly less than 95% of the time (e.g., 94.5% of the time). By placing the sensors ten millimeters apart in the wearable electronic device 100 with six channels, the user's hand gestures are accurately sensed more than 95% of the time (e.g., 97.6% of the time). By placing the sensors approximately fifteen millimeters apart in the wearable electronic device 100 with six channels the user's hand gestures are accurately sensed more than 95% of the time (e.g., 97.7% of the time). By placing the sensors twenty millimeters apart in the wearable electronic device 100 with six channels the user's hand gestures are accurately sensed more than 95% of the time (e.g., 97.7% of the time). Based on these findings, it has been discovered that the optimal separation distance d2 between the sensors (e.g., electrodes of the biopotential-signal sensing structure shown in FIGS. 5A-5C) of a respective pair of sensors is no more than nine millimeters. In some embodiments, a separation distance d2 of approximately nine millimeters (e.g., +/−0.2 to 0.3 mm of 9 mm) provides the greatest accuracy while improving comfort and anatomical conformity.

The proximal-distal diagram 2050 provides a visual representation of the measured separation distances d2 between sensors of a respective pair of sensors. As further shown in the proximal-distal diagram 2050, the separation distance d2 can be measured from the center of each sensor.

FIG. 16B illustrates the performance difference in the wearable electronic device 100 as the separation distance d2 between the respective sensors of pairs of sensors is increased. The Y axis is an R2 score or coefficient of determination. Performance plot 2170 includes a first performance line 2180 and a second performance line 2190. In some embodiments, the first performance line 2180 is a handstate correlation and the second performance line 2190 is pose detection. The first performance line 2180 is based on an R2 score, the higher the R2 score the better the measured values are at reproducing the original model. The second performance line 2190 is a classification score (a mean between the sensitivity and precision; a harmonic mean). The higher the classification score the better the classification of a pose. Handstate includes the position of the hand. Pose includes finger pinches (a total of 4; thumb to each of the medial digits), a closed fist, and/or an open hand. Each point in the FIG. 16B is a score for a given repetition. The first performance line 2180 includes the performance of respective sensors of pairs of sensors when the separation distance d2 is 8 mm, increased to 16 mm, increased to 24 mm, and increased to 32 mm. In some embodiments, the rows represent the respective pairs in the pairs of sensors. For example, the first row may correspond to a first pair, the second row may correspond to a second pair, etc.

FIG. 16B, together with FIG. 16A, illustrates selection of an adequate separation distance d2 between sensors of a respective pair of sensors, including that a small intra-channel separation distance of about 8 mm performs reasonably well as compared to other separation distances. Use of a small intra-channel separation distance can also reduce bulkiness of the wearable structure/watch band with which some of the sensors can be coupled. In some embodiments, the minimum separation distance between neuromuscular signal sensing contact points is dependent on the part of the body on which the user is wearing the wearable electronic device.

FIGS. 17A to 17F show a method 1700 of manufacturing a wearable band that includes a tubular textile band material surrounding an internal component, in accordance with some embodiments. The method 1700 includes embodiments that are more specific than those described with respect to example embodiments K1 through K10 discussed below. And thus, some of the features shown and/or described with respect to the method 1700 may not be necessary for performing all of the example methods of manufacturing described herein.

FIG. 17A shows example steps of the method 1700 for manufacturing the wearable band. The method 1700 including providing (1702) an internal band component, the internal band component including (i) a flexible printed circuit and (ii) a plurality of sensor-holding structures coupled with the flexible printed circuit. In some embodiments, the internal band component includes some or all of the components described with respect to FIG. 8A (e.g., an FPC 800 that includes a plurality of electrode-placement structures 804*a* to 804*f*, which each may include respective AFEs 802*a* to 802*f* for at least partially processing respective biopotential signals). For example, an internal band component 1730 can include the sensor-holding structures 1732-1, 1732-2, 1732-3, 1732-4, 1732-5, and 1732-6. In some embodiments, one or more of the sensor-holding structures 1732-1 to 1732-6 are configured to hold biopotential-signal-sensing electrodes, which may be configured to provide data obtained by respective biopotential-signal-sensing electrodes to a compute core housed within the manufactured band (e.g., via conductive pathways through the internal band component).

The method 1700 includes sheathing (1704) (e.g., using an adhesive), a tubular textile band cover 1733 over the internal band component, such that the tubular textile band cover is attached to the internal band component 1730, thereby producing a first portion of the covered band 1735. In some embodiments, a portion of the tubular textile band cover 1733 is terminated or otherwise formed into a particular structural aspect of the resulting wearable band 1701 (e.g., as part of enclosing a band portion (e.g., a first band portion that includes a cinch structure) of the wearable band 1701.

In some embodiments, adhering the tubular textile band cover 1733 over the internal band component 1730 includes causing the sensor-holding structures to visibly protrude from an exterior portion of the tubular textile band cover 1733. For example, a protruding portion 1734-1 of the tubular textile band cover 1733 indicates where the respective sensor-holding structure 1732-1 is located after the tubular textile band cover 1733 has been sheathed over the internal band component (e.g., FPC 800).

In some embodiments, textile-piercing pins or other extruding components are attached to one or more of the sensor-holding structures 1732-1 to 1732-6 before the tubular textile band cover 1733 is sheathed over the internal band component 1730, or at least the portion of the flexible printed circuit that includes the sensor-holding structures. In some embodiments, the textile-piercing pins or other extruding components are removable such that they are configured (e.g., integrally formed) to be detached from the respective sensor-holding structures 1732-1 to 1732-6 after the flexible printed circuit are sheathed by the tubular textile band cover.

Figure 17B:
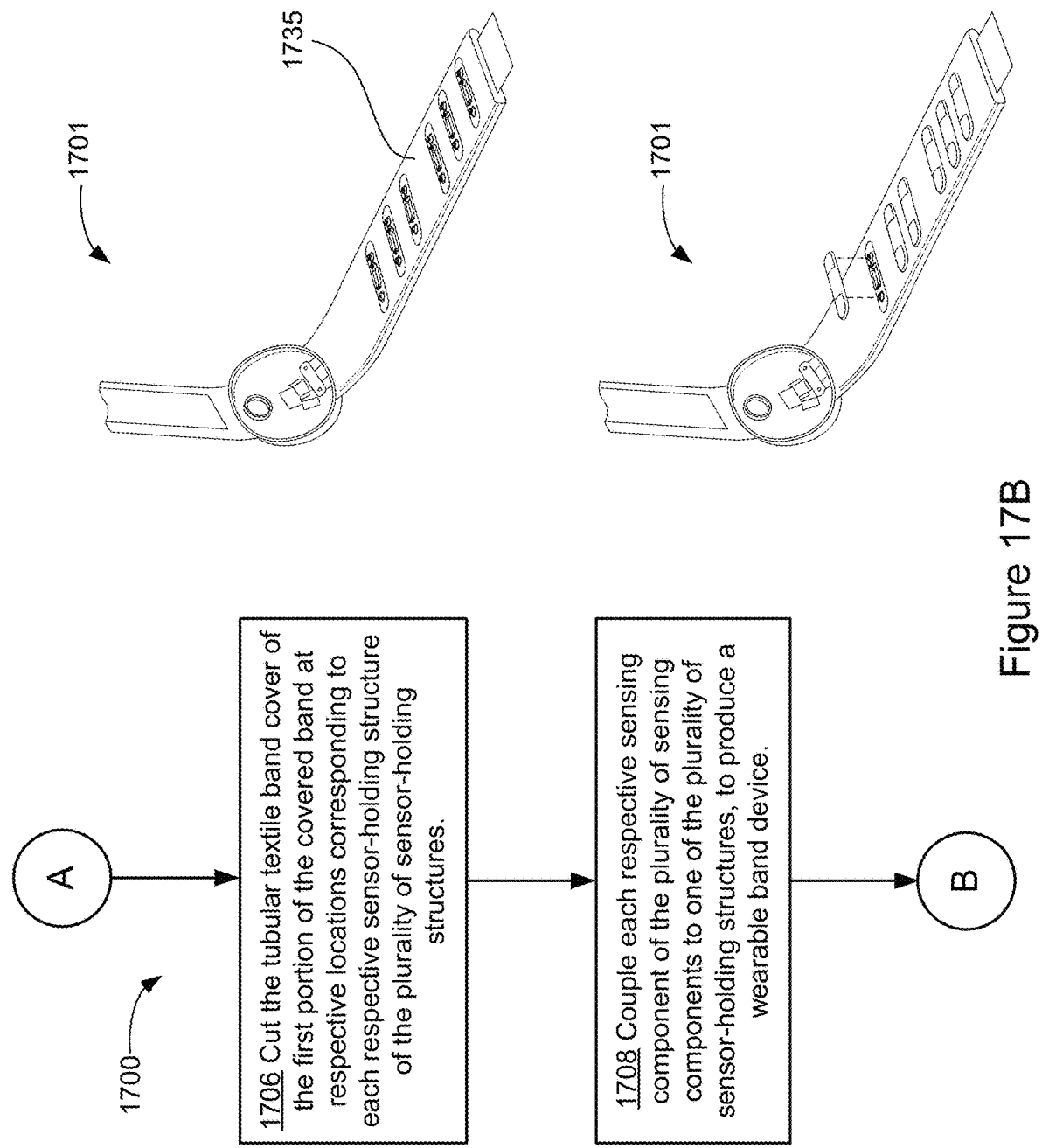

As shown in FIG. 17B, the method 1700 includes cutting (1706) the tubular textile band cover 1733 of the first portion of the covered band 1735 at respective locations corresponding to each respective sensor-holding structure of the plurality of sensor-holding structures 1732-1 to 1732-6. In some embodiments, circular portions are cut corresponding to respective mounting pins of each of the sensor-holding structures 1732-1 to 1732-6. In some embodiments, ovular portions are cut corresponding to respective perimeters of the sensor-holding structures 1732-1 to 1732-6. In some embodiments, the holes are centered based on a location of a respective sensor-holding structure (a respective mounting pin of the sensor-holding structure 1732-1). By cutting the holes corresponding to the respective sensor-mounting structures while the internal band component 1730 is sheathed by the tubular textile band cover 1733, the holes are precisely defined in locations corresponding to where the sensor-holding structures 1732-1 to 1732-6 will be located while the wearable electronic device 1701 is being worn by a wearer.

The method 1700 includes coupling (1708) each respective sensing component of the plurality of sensing components to one of the plurality of sensor-holding structures, to produce the wearable band 1701. In some embodiments, sensor-holding structures include some or all of the components of the receiving structures 810*a* to 810*f* shown in FIGS. 8A to 8G. In some embodiments, each of the plurality of sensing components are configured to snap into respective mounting pins of the sensor-holding structures 1732-1 to 1732-6.

Figure 17C:
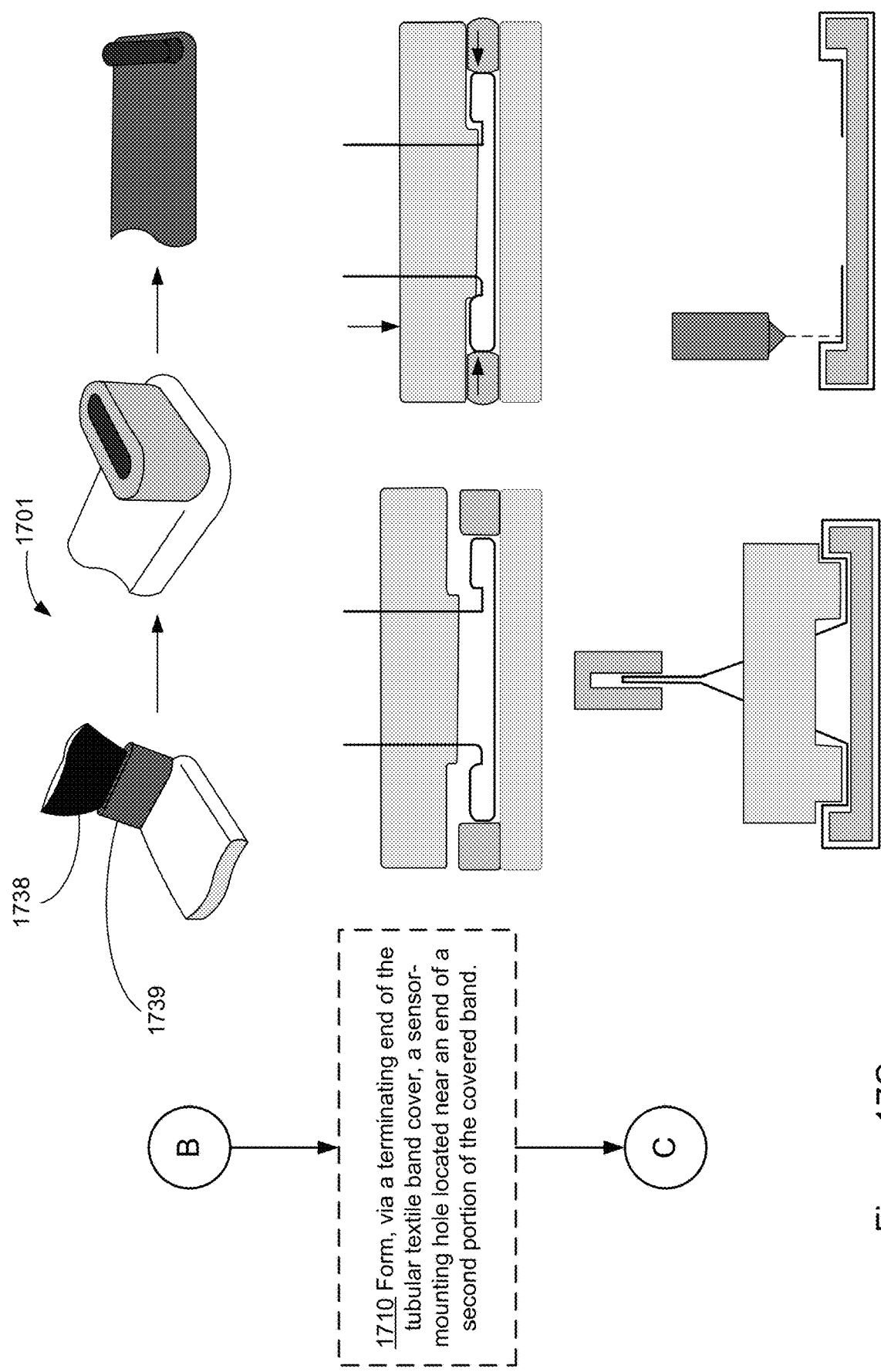

As shown in FIG. 17C, in some embodiments, the method 1700 includes forming (1710), via a terminating end 1738 of the tubular textile band cover 1733, a magnet-mounting hole 1734 near an end of the terminating end 1738 of the covered band 1701. In some embodiments, additional tooling is used define one or more of the sensor-mounting holes. For example, a terminating tooltip 1739 can be used to receive an adjustment length of the second portion of the covered band. In some embodiments, the terminating tooltip may also be used to define a cutting location for a magnet-placement hole configured to receive a rigid magnet for fastening the wearable band 1701.

As shown in FIG. 17D, in some embodiments, the method 1700 includes adhering (1712) a magnet (e.g., the magnet 1210 shown in FIG. 12E) within the magnet placement hole, such that the magnet placement hole substantially surrounds the magnet. In some embodiments, a textile cover, and/or a laminated cover layer is applied over the magnet inserted into the magnet placement hole. In some embodiments, the magnet placement hole is configured to receive a plurality of magnets (distributed along one or both of the major and minor dimensions)

As shown in FIG. 17E, the method 1700 includes mounting (1714) the covered band 1735 to an L-shaped tooling fixture, such that a location for cutting the geometrically shaped opening 1737 is located at the center of the L-shaped tooling fixture. In some embodiments, the covered band 1735 is mounted on the tooling fixture at a particular angle reflecting a shape of the compute core region that would be present while the covered band 1735 is being worn by a user. That is, in some embodiments a threshold tensile force is applied to the covered band while it is mounted on the L-shaped tooling fixture such that the compute core region is defined precisely for surrounding a compute core (e.g., the compute core 402) while the covered band 1735 is being worn by a wearer.

The method 1700 includes cutting (1716) a geometrically shaped opening 1740 into the tubular textile band cover 1733, the geometrically shaped opening 1740 configured to receive a compute core (e.g., which may include some or all of the components of the compute core 402 in FIG. 4C). In some embodiments, after the geometrically shaped opening 1740 is cut into the tubular textile band cover 1733, or in conjunction with the geometrically shaped opening 1740 being cut into the tubular textile band cover 1733, a portion of the geometrically shaped opening 1740 (e.g., an outer lip) is reinforced with additional material (e.g., an adhered polymer, as illustrated by the internal film layer 959) and/or is caused to project upward at an angle relative to an adjacent portion of the tubular textile band cover 1733. In some embodiments, the reinforced portion of the geometrically shaped opening 1740 is formed by removing less material from the reinforced portion during the cutting operation 1716.

In some embodiments, an inner case (e.g., the bottom case 906) of the compute core 402 is adhered to a compute-core location within an interior of the tubular textile band cover 1733 before the geometrically shaped opening 1740 is cut into the tubular textile band cover 1733. In this way, the geometrically shaped opening 1740 can be precisely positioned based on actual position where the computer core (e.g., the compute core 402) will be located during operations of the resulting wearable electronic device (e.g., the wearable electronic device 100) formed by constituent components described with respect to the example wearable devices described herein (e.g., the wearable device discussed with respect to the process described in FIGS. 8A to 8G). In some embodiments, the bottom case 906 is physically attached to the tubular textile band cover before the geometrically shaped opening 1740 is cut into the tubular textile band cover 1733.

Figure 17F:
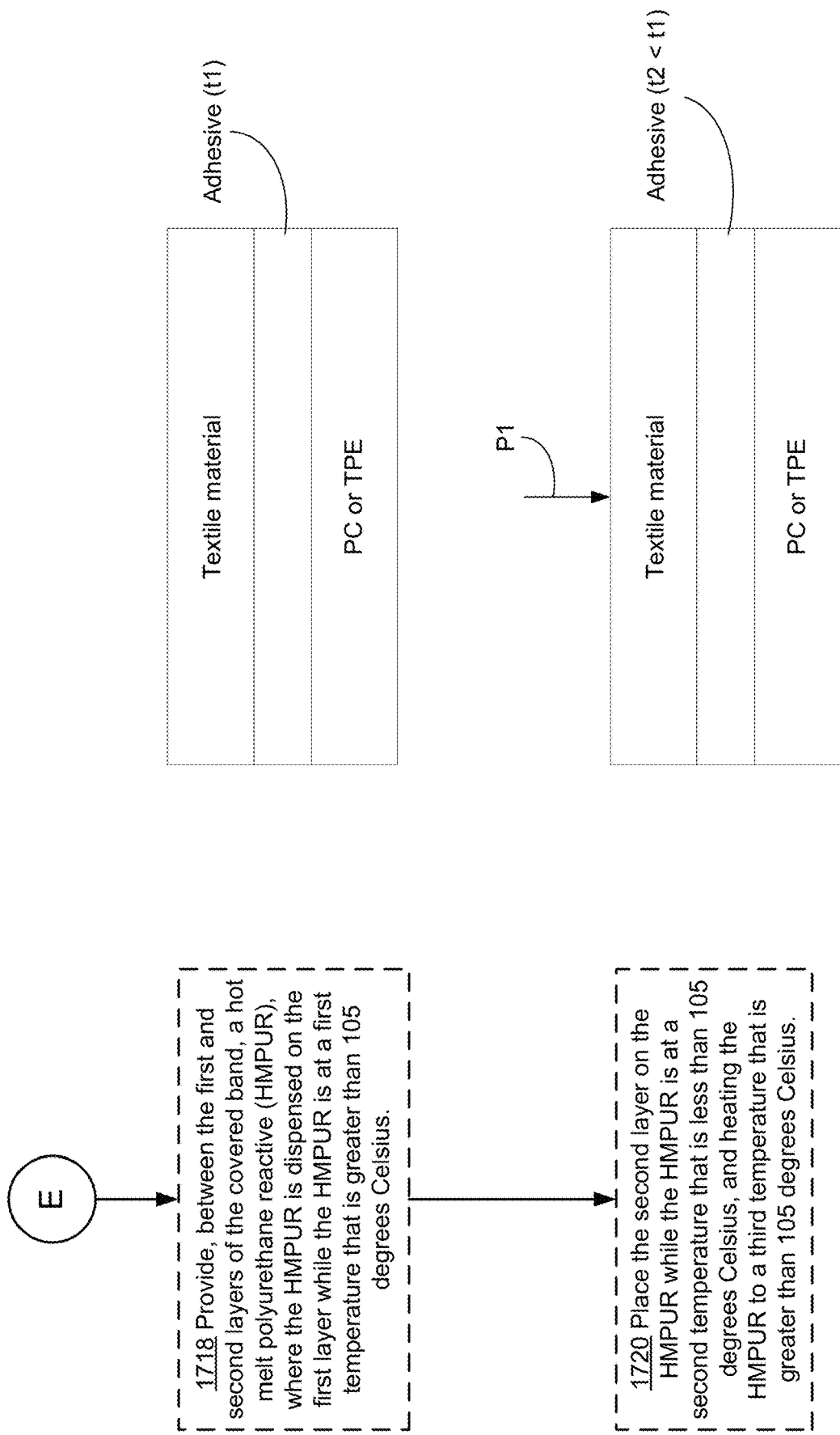

As shown in FIG. 17F, in some embodiments, the covered band portion 1735 includes a first layer and a second layer (e.g., an inner surface and an outer surface of the covered band, respectively). In some embodiments, the method 1700 includes providing (1718), between the first and second layers of the covered band 1735, a hot-melt polyurethane reactive (HMPUR), where the HMPUR is dispensed on the first layer while the HMPUR is at the first temperature that is greater than 105 degrees Celsius. In some embodiments, the HMPUR is in a liquid state while it is applied to the first layer of the covered band portion 1735. That is, in some embodiments, the HMPUR is applied while it is being heated above its respective melting point (which may be a temperature in the temperature range between 85 degrees and 140 degrees Celsius). In some embodiments, the temperature at which the HMPUR is applied to the first band portion is below a melting point temperature of the particular HMPUR that is being used, but is greater than a temperature at which the HMPUR begins exhibiting differentiated properties based on being close to the melting point (e.g., while the HMPUR is in a relatively tacky state compared to a solid state of the HMPUR while it is being held at room temperature).

In some embodiments, the method 1700 includes placing (1720) the second layer on the HMPUR while the HMPUR is at a second temperature that is less than 105 degrees Celsius (e.g., while the HMPUR is in a solidified state as compared to the state in which it was applied to the first layer of the covered band portion). That is, in some embodiments, the second layer of the covered band is applied to the HMPUR that is resting on the first layer of the covered band while a temperature of the HMPUR is below a respective melting point of the HMPUR being used. In some embodiments, while the second layer is placed on the HMPUR, the method includes heating the HMPUR to a third temperature that is greater than 105 degrees Celsius. In some embodiments, pressure is applied to the HMPUR (e.g., via a fixture configured to simultaneously heat and apply pressure to the second layer of the covered band portion) while the HMPUR is being heated to the third temperature. In some embodiments, the pressure is applied to the second layer of the covered band portion for at least 45 seconds, at least one minute, at least two minutes, etc.

Figure 18:
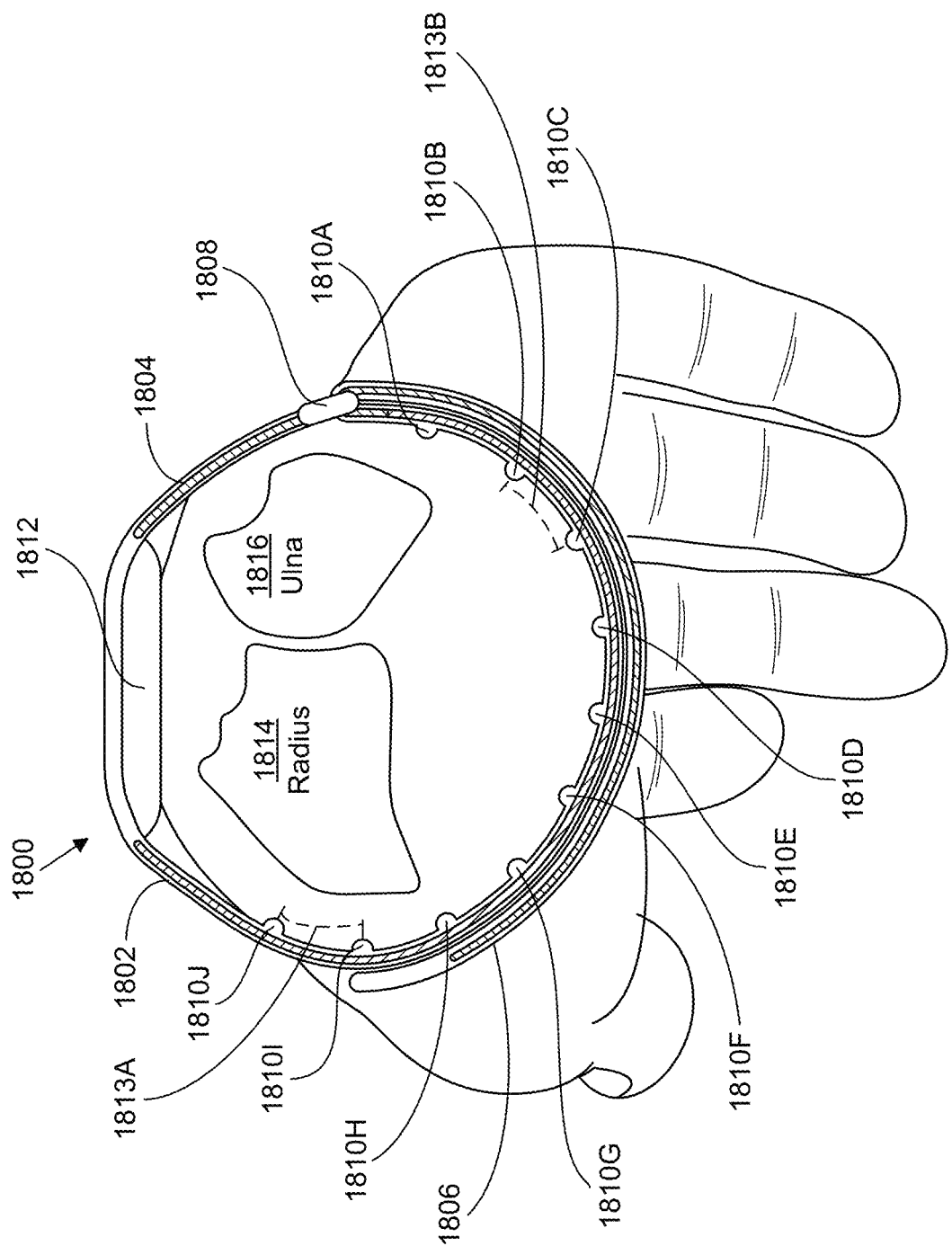
FIG. 18 shows an example of a wearable band that includes a plurality of biopotential-signal-sensing components (e.g., neuromuscular-signal sensors) distributed around a wrist portion of a wearer, in accordance with some embodiments.

FIG. 18 shows an example of a band 1800 that includes a plurality of biopotential-signal-sensing electrodes 1810A, 1810B, 1810C, 1810D, 1810E, 1810F, 1810G, 1810H, 1810I, and 1810J distributed around a wrist-facing portion (e.g., an inner surface) of the band 1800, in accordance with some embodiments.

In accordance with some embodiments, the band 1800 includes different band portions. The band 1800 includes a band portion 1802 (e.g., a first band portion, which may be described herein as a "smart band" portion) that includes electronic components, such as the plurality of biopotential-signal sensing electrodes. For example, the band portion 1802 includes the plurality of biopotential-signal-sensing electrodes 1810A to 1810J. And the band 1800 includes a band portion 1806 (e.g., a second band portion, which may be described herein as a "dumb band" portion) that does not include any electronic components that perform electronic functions. In some embodiments, more or less band portions may be present at the band 1800. For example, the band 1800 includes another band portion, band portion 1804 (e.g., a third band portion), which may be used to define a particular length of the band preceding the D-ring 1808 (e.g., a D-ring precursor band portion).

In some embodiments, the band portion 1802, the band portion 1804, and/or the band portion 1806, may be comprised of a first elastic material (e.g., an elastic polymer) with a first amount of elasticity. In some embodiments, the second band portion 1802 includes a first sub-portion that is at least partially elastic, and a second sub-portion that is inelastic (e.g., effectively rigid, such that a separation distance between respective biopotential-signal-sensing components of the second sub-portion of the second band portion 1802 are each separated by a fixed distance regardless of a diameter of wrist that band is enclosed around).

The band 1800 includes a second band portion 1802 that includes a plurality of signal-sensing components, including biopotential-signal-sensing electrodes 1810A to 1810J which may be configured to detect biopotential activity of a user at respective portions of the user's wrist. The second band portion 1802 may include a first sub-portion that includes a first subset of the plurality of biopotential-signal-sensing electrodes 1810A to 1810J, can be made from a material with a first elasticity that is configured to prevent deformation (e.g., stretching) of the first sub-portion of the second band portion 1802, such that the respective biopotential-signal-sensing electrodes that are located along the first sub-portion maintain a default spacing 1813A.

A second sub-portion of band 1800, which contains a second subset of biopotential-signal sensing electrodes of the plurality of biopotential-signal-sensing electrodes 1810A to 1810J, can be made from a different material than is used to make the first sub-portion of the band 1800, such that the second subset of biopotential-signal-sensing electrodes can have a dynamic spacing range greater than the default spacing 1813A (e.g., the spacing 1813B, which is greater than the default spacing 1813A). The differences and spacing between the respective subsets of biopotential-signal-sensing electrodes of the respective sub-portions of the second band portion 1802 can be based on respective levels of biopotential activity detectable at different portions of the user's wrist during particular times (e.g., while the user is performing particular activities (e.g., exercises, gestures corresponding to different operations)) while wearing the band 1800. In some embodiments, the respective levels of biopotential activities detectable by the corresponding subsets of biopotential-signal-sensing electrodes may be based on body parts of the user corresponding to the different wrist-portions being detected by each of the plurality of biopotential-signal-sensing electrodes 1810A to 1810J (e.g., a radius 1814 and an ulna 1816).

In some embodiments, other aspects of the first and second subsets of the biopotential-signal-sensing electrodes 1810A to 1810J can be present in the band 1800. For example, the different subsets can have different respective sensing densities (e.g., based on a first spacing and a second spacing between respective biopotential-signal-sensing electrodes of the band 1800 while the second band portion 1802 is in an unstretched state). Alternatively, the level of activity and/or sensing density of the different subsets of biopotential-signal-sensing electrodes can be different for each subset of the second band portion 1802.

Figure 19:
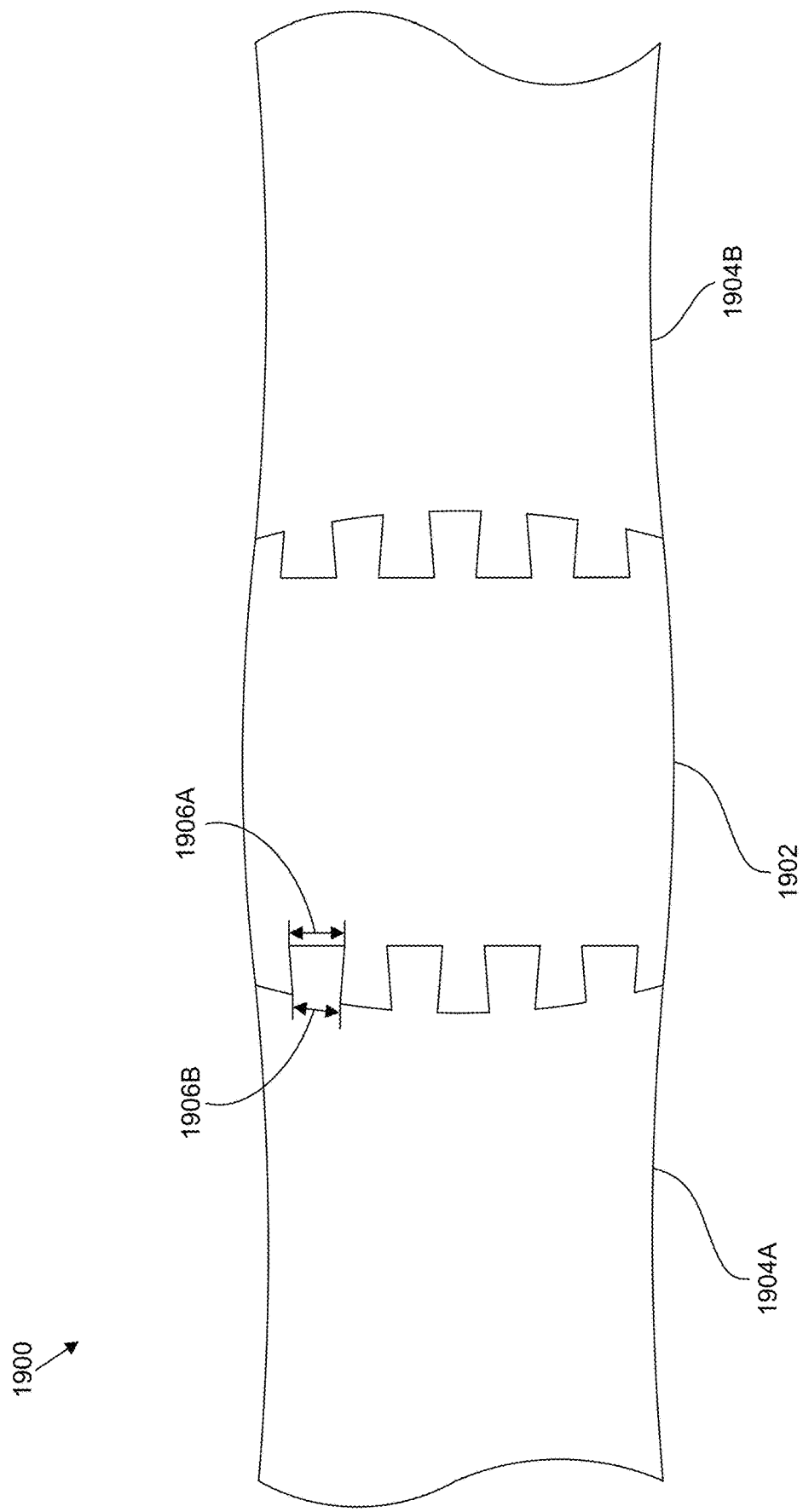
FIG. 19 shows an example of an internal band component portion that includes linking structures for connecting respective band portions of the wearable device with a compute core of the internal band component.

FIG. 19 shows an example of an internal band component 1900 that includes linking structures for connecting respective portions 1904A and 1904B of the internal band component 1900 to a core-mounting structure 1902 of the internal band component 1900. One of ordinary skill in the art will appreciate that the respective portions 1904A and 1904B of the internal band component 1900 are shown in a cut view that does not include the entire length of each of the respective portions 1904A and 1904B, and that the linking portions of core-mounting structure 1902 may be more or less numerous in various embodiments than those illustrated herein. In accordance with some embodiments, the core-mounting structure 1902 and the respective portions 1904A and 1904B include linking portions that are configured to couple the core-mounting structure 1902 to each of the respective portions 1904A and 1904B. Each of the respective linking portions of the couplable components of the internal band component 1900 may be sized to cause a snap fit between the couplable components, thereby providing additional tensile strength to prevent deformation of the internal band component 1900. For example, the core-mounting structure 1902 includes a link-receiving opening that has a first width of 1906B that is less than a second width 1906A, such that the second width 1906A is the same as a maximum width of a corresponding linking extrusion of the respective portion 1904A of the internal band component 1900.

In some embodiments, spacing between linking extrusions of the respective portions 1904A and 1904B and the core-mounting structure 1902 constitutes one or more link-receiving openings. That is, in some embodiments, each respective coupling interface of each respective internal band component can include alternating linking extrusions and link-receiving openings.

In some embodiments, linking extrusions of one or more of the respective components of the internal band component 1900 are formed during a molding process that is part of a manufacturing process for manufacturing a wearable band (e.g., the method 800 shown in FIGS. 8A-8G, and/or the method 1700 shown in FIGS. 17A-17F).

Figure 20:
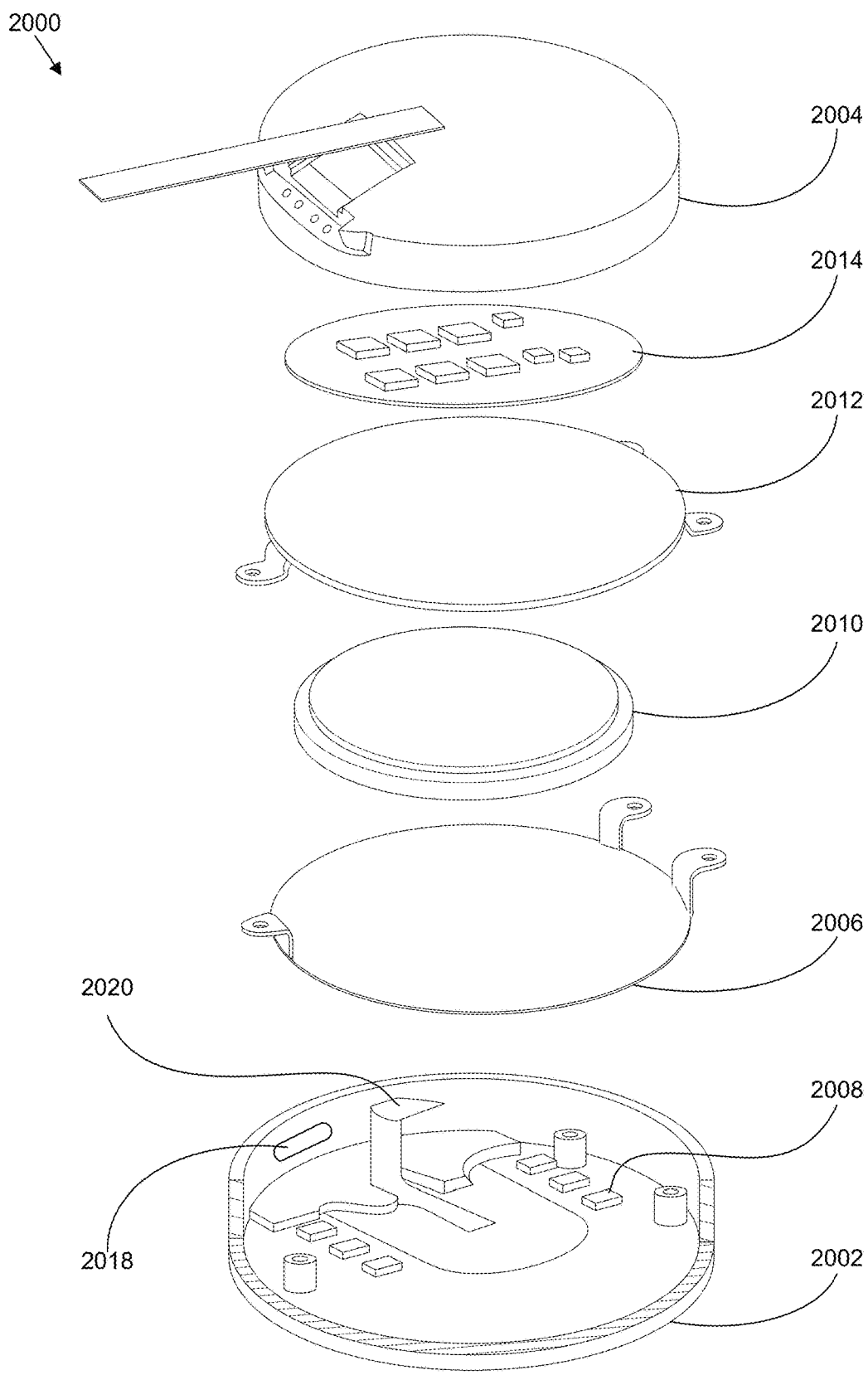
FIG. 20 shows an example of a compute core for a wearable electronic device having a skin contact surface and defining a cavity, in accordance with some embodiments.

FIG. 20 shows an example of a compute core 2000 for a wearable electronic device (e.g., the wearable electronic having a skin contact surface and defining a cavity, in accordance with some embodiments. While FIG. 20 shows respective components of the compute core 2000 exploded away from each other for ease of reference, one of skill in the art will appreciate that in practice, one or more of the components shown in the exploded view of the compute core 2000 may be physically coupled or otherwise in operable communication while the compute core 2000 is being used (e.g., being worn by a user).

As shown in FIG. 20, the compute core 2000 includes a bottom case 2002, and a top case 2004, which may be configured to physically couple (e.g., removably or permanently couple) to form the compute core 2000, and may also define a cavity for housing various electronic components.

In some embodiments, the bottom case 2002 of the compute core 2000 includes a skin contact surface that is configured to form a physical contact with a portion of a user's skin while they are wearing a wearable electronic device (e.g., the wearable electronic device 100) that is housing the compute core 2000. In some embodiments, the bottom case 2002 further includes one or more analog front ends (e.g., the analog front end component 2008), which may be configured to partially process neuromuscular signals detected by near the skin contact surface of the user (e.g., via one or more electrode portions of an electrode assembly disposed on a lower surface of the bottom case 2002, as shown in FIGS. 21A to 21D).

In accordance with some embodiments, the compute core 2000 includes a metallic baseplate 2006, which is located between the bottom case 2002 and the top case 2004. And, in accordance with some embodiments, the compute core 2000 further includes a battery 2010 that is configured to be placed on a first side (e.g., a top, seated surface of the metallic baseplate 2006). In some embodiments, the compute core 2000 further includes a mid-plate that is configured to separate the battery 2010 from a main logic board (MLB) 2014, which may be configured for managing controlling operations of the compute core 2000 and/or the wearable electronic device of which the compute core 2000 is constituent of. For example, the MLB 2014 may be configured to receive electrical signals from one or more AFEs (e.g., such as the AFE component 2008 located on the surface of the bottom case 2002, and/or one or more AFEs disposed within a band portion of the wearable electronic device comprising the compute core 2000.

In some embodiments, the metallic baseplate 2006 is configured for dual purposes of providing an electrical ground for one or more electrode assemblies on the skin contact surface of the compute core 2000, and to electrically shield the one or more electrode assemblies from electrical and magnetic noise. In some embodiments, at least some of the electrical and magnetic noise is from at least one of the main logic board and the battery. In some embodiments, the AFE (e.g., including the AFE component 2008) is placed on a first side of the metallic base plate 2006, and the MLB 2014 is located on a second side that is opposite to the first side of the metallic base plate 2006.

In some embodiments, mid-plate 2012 is configured to provide a physical shield at a top portion of the battery 2010, and the mid-plate 2012 is configured physically connect to the bottom case 2002 via physical tabs that extend in a direction that is substantially orthogonal to a plane defining a respective first surface of the metallic base plate 2006.

In some embodiments, the compute core 2000 includes an antenna component that is configured to be at least partially disposed along an inner edge of the top case 2004 of the compute core 2000, which may minimize the extent to which signals directed to the antenna are deflected or otherwise interfered by other components housed within the compute core 2000 (e.g., the metallic baseplate 2006). In some embodiments, the bottom case 2002 includes a linear resonant actuator (LRA) that is configured to provide haptic feedback to a wearer of the wearable electronic device comprising the compute core 2000 (e.g., haptic feedback provided at the skin contact surface of the compute core 2000).

In some embodiments, the bottom case 2002 of the compute core 2000 includes a shaped circuit board that includes a flexible component 2020 that may be configured to protrude in a substantially orthogonal direction to a plane defined by a flat inner surface of the bottom case 2002. In some embodiments, the flexible component 2020 is configured to electronically couple one or more AFE components (e.g., housed within the bottom case 2002) to the MLB 2014. That is the flexible component 2020, which may be referred to herein as a dome flex assembly, may include electronic circuitry for providing partially processed neuromuscular signals detected proximate to the skin contact surface of the compute core 2000 to the MLB 2014. In some embodiments, the flexible component 2020 is configured and arranged such that it does not come into physical contact with one or more other components of the stack of components housed by the compute core 2000.

FIG. 21 shows aspects of a skin-contacting surface of a compute core for a wearable electronic device, in accordance with some embodiments. In some embodiments, a compute core 2200 is provided, which may include some or all of the components of the compute core 2000 described with respect to FIG. 20.

As shown in FIG. 21, in accordance with some embodiments, a compute core 2200 is provided, where the compute core 2200 includes a skin contact surface 2201, where the skin contact surface 2201 includes two electrode assemblies on opposite sides of the skin contact surface. Each of the electrode assemblies includes a plurality of electrode portions (e.g., electrode portions 2202-1, 2204-1, and 2206-1 of a first electrode assembly, and electrode portions 2202-2, 2204-2, and 2206-2 of a second electrode assembly). As shown in the top view of As shown in the top view of FIG. 21, in some embodiments, respective inner edges of each of the electrode assemblies may be separated by at least an assembly separation distance 2208, and/or respective midpoints of the respective electrode assemblies may be separated by an assembly midpoint separation distance 2210, which may correspond to positions of the electrode assembly components that have a greatest protrusion distance from a plane defined by the skin contact surface 2201 of the compute core 2200. In some embodiments, each respective electrode portion of the respective electrode assemblies is separated by at least a skin detection distance 2212, which may be configured to minimize interference of neuromuscular signal detection between the respective electrode portions of the electrode assemblies. In some embodiments, each electrode assembly includes two end portions, which form respective first and second ends of each electrode assembly, and a center portion of the electrode assembly separates the respective end portions. In some embodiments, each of the end portions of the respective electrode assemblies are electrodes of a first type (e.g., having a first detection means, a first level of sensitivity, etc.), and the respective center portion electrode assembly is an electrode of a second type, distinct from the electrodes of the first type. In some embodiments, each of the edge portions are separated by a sensor type separation distance 2214, such that any interference (e.g., noise) is minimized further between respective electrodes having similar sensing capabilities.

As shown in the side profile view of the compute core 2200 shown in FIG. 21, one or more of the electrode portions 2202, 2204, and 2206 may be configured to have a particular protrusion depth 2216, which may be determined based on a physical aspect of the wearer of the wrist-wearable device comprising the compute core 2200. For example, a user having a higher body mass index (BMI) may require respective electrode assemblies having a shorter protrusion depth 2216, whereas a user having a lower BMI may require electrode assemblies having a longer protrusion depth.

FIG. 22 shows examples of different wrist-wearable devices having different relative dimensions based on physical aspects of respective wearers of the different wrist-wearable devices, in accordance with some embodiments. For example, a wearable electronic device 2302 is being worn by a wearer 2301. And a different wearable electronic device 2352 is being worn by a different wearer 2351.

In accordance with some embodiments, particular aspects of wearable electronic devices can be sized to meet functional requirements of such devices, where the sizes required for meeting the functional requirements are dependent on physical aspects of the respective wearers (e.g., the wearers 2301 and 2351). For example, different wearers having different body mass indices (BMIs) may have wrist profiles that are defined, at least in part, by the different BMIs. For example, a user with a relatively lower BMI may have a wrist profile having a greater amount of concavity in particular regions (e.g., near a tendon on the inner portion of the wrist).

In accordance with some embodiments, the wearable electronic device 2302 includes at least one band portion that includes a plurality of neuromuscular-signal-sensing components (e.g., EMG electrodes), where each of the neuromuscular-signal-sensing components has a particular dimension that is based on a physical aspect of a body of the wearer of the wearable electronic device. For example, the wearable electronic device may include electrodes having particular protrusion heights, such that the electrodes are configured to the contact a skin surface of the wearer, based on particular concavities of the user's skin in that area.

As shown in FIG. 22, the user 2301 has a wrist profile having a first set of concavities 2304-A and 2304-B, and the user 2351 has a wrist profile having a second set of concavities 2354-A and 2354-B, where the concavities 2304-A and 2304-B are larger (e.g., deeper, broader) than the concavities 2354-A and 2354-B, which may be related to respective BMIs of each of the users. Since such concavities (e.g., peaks and valleys of the users' wrist contours) may vary from one user to another, multiple different stock keeping units (SKUs) of the wearable electronic devices described herein may be provided to accommodate the different profiles of the users' bodies.

In accordance with some embodiments, the wearable electronic device 2302 corresponds to a first SKU for wearers having a BMI in a first range (e.g., a BMI that is less than 20), and the wearable electronic device 2352 corresponds to a second SKU for wearers having a BMI in a second range (e.g., a BMI that is greater than 20 but less than 25), such that the wearable electronic devices 2302 and 2352 may have identical lengths, but may include neuromuscular-signal-sensing components having different relative sizes. For example, a set of sensors disposed along the band portion of the wearable electronic device 2302 may have a height that is between 1 and 4 millimeters greater than the sensors disposed along the band portion of wearable electronic device 2352, based on a difference in size of the concavities 2304-A and 2304-B compared to concavities 2354-A and 2354-B.

In some embodiments, respective second sets of electrodes of the wearable electronic devices 2302 and 2352 (e.g., electrodes on skin contact locations associated with the compute cores of the respective wearable electronic devices) may have uniform heights across SKUs, since there is less variation of required penetration depths for these regions of the wearers' skin.

In some embodiments, wearers can provide personal sizing information to a server associated with a manufacturer of the wearable electronic devices 2302 and 2352, including images of the respective wearers' wrists. In some embodiments, wearers may provide other information such as demographic factors (e.g., gender, ethnicity) which may have a correlation to the wearers' wrist geometries and/or other anthropometric body factors that are relevant to the required height profiles of sensors for detecting biopotential signals of the users. In other embodiments, particular SKUs are configured to accommodate various ranges of user profiles, which may be considered a more cost-effective approach that maximizes the cost-benefit analysis of providing affordable wearable devices with sufficient sensing capabilities for a particular set of tasks to be performed by the wearable electronic devices.

Example Embodiments (A1) In accordance with some embodiments, an adjustable band is provided. The adjustable band includes a first band portion having a first distal end. The adjustable band further includes a second band portion having a second distal end. In some embodiments, the first band portion and the second band portion are components of a wrist-wearable device (e.g., a smart watch). In some embodiments, the first band portion and the second band portion are separated by an integrated display of the wrist-wearable device. And the adjustable band further includes a cinch structure coupled to the first distal end, where the cinch structure defines an opening that extends beyond the first distal end in a direction substantially perpendicular (e.g., within 5 degrees of perpendicular relative to a direction of the length of the first band portion) to the longest dimension of the first band portion. In other words, the opening of the first cinch structure is not just an extension of the first distal end. In some embodiments, the cinch structure is a separate structure that can extend above the first distal end (as depicted in FIGS. 2A-2E), such that when the adjustable band is viewed by a user looking down to the adjustable band, the opening is closer to the user than is the first distal end. The opening defined by the cinch structure is configured to (e.g., sized to, formed to, shaped to, etc.) (i) have an adjustment length of the second band portion (e.g., an attachment length), including the second distal end, be fed therethrough, and (ii) cause the cinch structure to apply a frictional force adjacent to (e.g., frictionally engage with the cinch structure) the adjustment length of the second band portion. In some embodiments, a cross-sectional size of the opening relative to a cross-sectional size of the second band portion and/or the second distal end is one means for causing the frictional force to be applied to the second band portion. In some embodiments, the cinch structure is caused to apply a first frictional force while the second band portion and/or the second distal end is being received, and a second frictional force after the second band portion and/or the second distal end has been received by the cinch structure. In some embodiments, the second frictional force is greater than the first frictional force by at least 0.2 Newtons. After the adjustment length of the second band portion is fed through the opening defined by the cinch structure, an adjustable loop is formed, where the adjustable loop has a first circumference sized to fit around a wrist of a user.

In some embodiments, the circumferential shape is sized according to a set of fixed sizes. For example, there can be discrete sizes of the band structure such that users with different wrist sizes can wear the wearable electronic device with a different first circumference while maintaining a minimum fidelity of signal sensing based on the locations of the biopotential-signal sensing structures for each respective size of the wearable electronic device 100. In some embodiments, the first circumference is substantially the same as the wrist of the user. In some embodiments, the first circumference is configured to be slightly larger than the wrist of the user, such that there is a slight gap between at least a portion of the adjustable loop and the wrist of the user. In some embodiments, the gap can account for sensors external to the first band portion and/or the second band portion, and/or hardware associated with a display device and/or the associated structure for retaining the display device. The first band portion and the second band portion can be distinct from each other, or permanently formed together when fully assembled.

In some embodiments, the display device can be a removable capsule device configured to separate from the adjustable loop. In some embodiments, the wearable electronic device is configured to be worn on a forearm and/or an ankle of the user. In some embodiments, the wearable electronic device is configured to be worn around a finger and/or toe of the user. In some embodiments, it is configured to be worn around a finger and/or toe of the user. The frictional force applied by the cinch structure is configured to be maintained adjacent to the adjustment length of the second band portion while the adjustable band is worn by the user, such that the first circumference of the adjustable loop is also maintained. In some embodiments, the first circumference is maintained, in part, by the frictional force applied by the cinch structure to the second band portion. In some embodiments, one or more additional components (e.g., a frictional surface modifier) are used to maintain the first circumference.

(A2) In some embodiments of A1, while the adjustment length is fed through the opening at a first angle relative to a planar surface of the opening (e.g., where the first angle is at least five degrees), the opening is configured to have the adjustment length of the second band portion be fed therethrough. A first frictional force is caused to be applied by the cinch structure when the adjustment length of the second band portion is fed through the opening at the first angle, where the first frictional force is less than the frictional force that is applied adjacent to the adjustment length of the second band portion to maintain the first circumference of the adjustable loop. In some embodiments, the first frictional force is at least 0.3 Newtons less than the frictional force that is applied adjacent to the adjustment length of the second band portion to maintain the first circumference of the adjustable loop. For example, as shown in FIGS. 3A-3B, while the cinch structure is pivoting relative to the angle of the opening, a protrusion located at the bottom of the opening rotates such that an opening height between a top of the cinch structure, and a top surface of the protrusion increases. In other words, the opening is defined between the top of the cinch structure and the top surface of the extrusion, which is attached to the bottom of the cinch structure, according to some embodiments.

In some embodiments, while the cinch structure pivots away from the opening, the extrusion pivots such that an impinging height of the extrusion that is extending up from the bottom of the cinch structure decreases. In some embodiments, the cinch structure is a bistable locking mechanism, the bistable locking mechanism having a first equilibrium state in an open position while it is not receiving the second band portion, and the bistable locking mechanism having a second equilibrium state in a closed position while it is receiving the second band portion.).

(A3) In some embodiments of A1-A2, the adjustable band includes a frictional surface modifier (e.g., a protruding component 206, as shown in FIGS. 2A-2E) disposed on a surface of the opening configured to have the adjustment length of the second band portion fed therethrough. The frictional surface modifier is configured to increase a coefficient of friction at the surface of the opening (e.g., by at least 0.15 Newtons).

In some embodiments, the increased coefficient of friction at the surface of the opening improves the ability of the cinch structure hold the first circumference size after adjustment. It also improves the ease for feeding through the attachment length of the second band portion. For example, the band structure may include a series of bumps to allow for the band to be adjusted in steps. In some embodiments, the opening of the cinch structure includes a frictional surface modifier for securing the second band portion (e.g., the portion the second band passes through has a rough surface designed to keep the second band in place).

(A4) In some embodiments of A2-A3, the adjustable band further includes one or more protrusions (e.g., a bump, a physical structure defined by the shape of the opening, etc.) extending upwardly from the planar surface of the opening defined by the cinch structure, such that when the adjustment length of the second band portion is fed through the opening at the first angle, the adjustment length makes contact with one or more protrusions. In some embodiments, the planar surface is a lower edge of the opening. In some embodiments, the lower edge of the opening is substantially flush with the first band portion. In some embodiments, the opening includes a compression plate attached to a lower edge of the cinch structure, where the compression plate is removable and different sized compression plates can be used to increase the frictional force acting on the second band portion.

(A5) In some embodiments of A4, the one or more protrusions are configured to adjust a cross-sectional opening size for the second band portion to pass through, thereby increasing the frictional force on the second band portion. In some embodiments, the component is removable and allows for different components that can adjust the cross-sectional opening size more or less to either decrease or increase the frictional force on the second band portion.

(A6) In some embodiments of A1-A5, a portion of the cinch structure is adhered (e.g., partially, less than all) to the first band portion with an adhesive.

(A7) In some embodiments of A6, the first distal end includes a cinch-coupling piece (e.g., or tapered end, which can be caused by compression or by using less material at one end of the band portion), such that the cinch-coupling piece has a cross-sectional dimension that is less than a corresponding cross-sectional dimension of a remainder of the first band portion. The cinch structure defines a pocket (e.g., an ingress portion configured to receive the cinch-coupling piece, which can be, for example, a tapered end of the band portion) configured to receive the cinch-coupling piece, and the adhesive is configured to adhere the pocket of the cinch structure to the cinch-coupling piece of the first distal end of the first band portion.

(A8) In some embodiments of A7, the cinch structure is a two-piece cinch structure, a first piece of the cinch structure defining the opening and a second piece of the cinch structure including a shoulderless spring bar that couples the first piece of the cinch structure to the second piece of the cinch structure. In some embodiments, one of the first piece of the cinch structure and the second piece of the cinch structure is substantially encased within the first band portion or the second band portion.

(A9) In some embodiments of A8, the first piece of the cinch structure is configured to rotate (e.g., pivot) relative to the second piece of the cinch structure, such that when the adjustment length of the second band portion is fed through the opening of the cinch structure, the first piece of the cinch structure is configured to reduce a normal force while the adjustment length of the second band portion is being fed through the opening. In some embodiments, the normal force is reduced while the adjustment length remains parallel to a bottom edge of the cinch structure.

(A10) In some embodiments, of A9, the adjustable band further includes a spring (e.g., a shoulderless spring bar). In some embodiments, rotating the cinch structure moves the second piece of the cinch structure relative to the first piece of the cinch structure in a first direction and also causes the spring to oppose a movement of the second piece of the cinch structure in the first direction.

(A11) The adjustable band of A8, where (i) the second piece of the cinch structure (e.g., a detached cinch mount) is substantially encased in the first band portion, (ii) the shoulderless spring bar is partially encased in the first band portion, and (iii) the first piece of the cinch structure is pivotably attached to the shoulderless spring bar at an exterior surface of the first band portion.

(A12) The adjustable band of A11, where a polymer material (e.g., a liquid crystal infused material, a liquid crystal infused fiber material, Vectran, etc.) extends along an interior layer of the first band portion, wherein the polymer material is configured to keep the second piece of the cinch structure and the shoulderless spring bar in a fixed relationship relative to one another.

(A13) In some embodiments of A1-12, the first band portion and the second band portion are part of a unitary structure that includes a plurality of sensors.

(A14) In some embodiments of A13, the second band portion does not include any electronic components, including any of the plurality of sensors. In other words, one side of the wearable electronic device has sensors, and the other side does not, and is configured to be flexible and durable to perform the functions described herein for maintaining the circumference of the adjustable band. For example, the first band portion (e.g., the band portion 104 in FIGS. 1A-IC) can be a "smart band" that performs electronic functions, and the second band portion (e.g., the band portion 102) can be a "dumb band," in the sense that it does not include electronic components that perform electronic functions.

In some embodiments, the second band portion is stretchable in the lengthwise direction to at least 10% of an unstretched length. In some embodiments, the second band portion can be stretched by up to 20% of a length of the longest dimension of the second band portion, to accommodate users with larger wrist sizes. For example, the available sizes of the wearable device can be sized to fit the smallest wrist sizes in the respective sizes appropriately, while allowing the band to be stretched to accommodate larger sizes.

(A15) In some embodiments of A13-A14, at least one of the plurality of sensors is a biometric sensor.

(A16) In some embodiments of A1-A15, (i) the opening has a first height at a first side of the opening, and (ii) the opening has a second height at a second side of the opening, where (a) the second height is different than (e.g., greater than or less than) the first height, such that the first side of the opening is configured to retain the second band portion after it is received by the opening, and (b) the first side of the opening and the second side of the opening are configured and arranged opposite each other. The inventors have discovered that an opening with a smaller side of the opening that applies a frictional clamping force and another side of the opening that is substantially larger and applies substantially less force can be helpful for minimizing the amount of wear and tear on the band structure.

(A17) In some embodiments of A1-A16, the adjustable band includes a first magnet, the first magnet being disposed along at least one-third of a first length from a first proximal end of the first band portion to the first distal end of the first band portion. As used herein, a magnet being disposed on or at a portion of an adjustable band (which can optionally be referred to as a wrist-wearable device, smart watch, etc.) can mean that the magnet is attached to (e.g., anchored interior or exterior surfaces), enclosed in (e.g., embedded between two connected portions of the respective band portion), or otherwise affixed to the respective band portion. In some embodiments, the first magnet forms part of a composite material that includes an elastic polymer material and a magnetically charged material, and the second magnet is a rigid magnet. In some embodiments, the magnet can be disposed at a respective portion of the adjustable band and still be completely insulated from the outer material of the adjustable band (e.g., by way of a Vectran material, or other spun fiber, and/or an elastic polymer (e.g., elastomer)). In some embodiments, the first magnet and/or one or more additional magnets located on the first band portion are distributed such that there are magnets along at least one half of the length of the first band portion. In some embodiments, the first magnet and/or the one or more additional magnets are distributed along at least two-thirds, three-fourths, or the entire length of the first band portion. The adjustable band further includes a second magnet disposed at (e.g., less than 35 millimeters of) the second distal end. In some embodiments, at least a portion of the second magnet is located at the second distal end. In some embodiments, the second distal end is comprised of a textile material, the textile material including a pocket of excess textile material. In some embodiments the pocket is configured to receive an injection-molded magnet frame that is configured to maintain a position of the second magnet at the second distal end. The second magnet is configured to form a first connection with the first magnet when the adjustable loop is formed by the first band portion and the second band portion, and the first connection retains the first circumference (e.g., with a retaining force of at least 2 Newtons).

(A18) In some embodiments of A17, the adjustable band includes a third magnet. The third magnet is disposed on the second band portion, and the third magnet is configured to provide a second connection with the first magnet, distinct and separate from the first connection. In some embodiments, the third magnet is part of a composite that includes another material. In some embodiments, the third magnet is part of a different composite than the first magnet.

In some embodiments of A18, the first connection and the second connection are configured to apply a combined magnetic force to maintain the first circumference of the adjustable loop. In some embodiments, the third magnet is disposed around the second magnet such that the second connection encompasses the first connection. In some embodiments, the second connection has a second retaining force of at least 0.2 newtons. In some embodiments, one or more of the first magnet, the second magnet, and the third magnet are disposed within an interior of the second band portion.

In some embodiments of A18, at least one of the magnets that is disposed within the interior of the second band portion is configured to be substantially flush with an outer surface of the second band portion. In some embodiments, the first magnet is disposed within an interior layer of the first band portion, such that no portion of the first magnet is exposed, and a portion of the second magnet is exposed near the second distal end. In some embodiments, the portion of second magnet that is exposed near the second distal end is coated with a non-magnetic material (e.g., an epoxy-based adhesive). In some embodiments, the non-magnetic material is configured to be substantially flush with an inner surface of the second band portion. In some embodiments, the first magnet includes a magnetic chain and an elastic polymer material disposed within the magnetic chain.

(B1) In accordance with some embodiments, a cinch structure configured to be fed a band portion of an adjustable band structure is provided. The opening is configured to (i) receive a portion of a band having an adjustment length, including an end of the band, and (ii) cause the cinch structure to apply a frictional force adjacent to the adjustment length. After the adjustment length of the portion is fed through the opening defined by the cinch structure, the adjustable loop is formed having a first circumference around a wrist of a user. The frictional force applied by the cinch structure is configured to be maintained adjacent to the adjustment length of the portion while the adjustable loop is worn by the user, such that the first circumference of the adjustable loop is also maintained.

(C1) In accordance with some embodiments, a wrist-wearable device is provided. The wrist-wearable device includes an electronic display. The wrist-wearable device further includes memory comprising instructions, which when performed at a processor of the wrist-wearable device, cause execution of functions at one or more of the electronic display and one or more sensors of the wrist-wearable device. The wrist-wearable device further includes an adjustable band coupled with the electronic display; the adjustable band includes a first band portion having a first distal end. The wrist-wearable device further includes a second band portion having a second distal end. The wrist-wearable device further includes a cinch structure coupled to the first distal end. The cinch structure defines an opening that extends beyond the first distal end in a direction substantially perpendicular to the longest dimension of the first band portion. The opening is configured to (i) have an adjustment length of the second band portion, including the second distal end, be fed therethrough, and (ii) cause the cinch structure to apply a frictional force adjacent to the adjustment length of the second band portion. After the adjustment length of the second band portion is fed therethrough the opening defined by the cinch structure, an adjustable loop is formed having a first circumference around a wrist of a user. The frictional force applied by the cinch structure is configured to be maintained adjacent to the adjustment length of the second band portion while the adjustable band is worn by the user, such that the first circumference of the adjustable loop is also maintained.

(D1) In accordance with some embodiments, a method for assembling an adjustable band of a wearable electronic device is provided. The method includes attaching a first band portion having a first distal end to a cinch structure. The cinch structure defines an opening that extends beyond the first distal end of the first band portion in a direction substantially perpendicular to a longest dimension of the first band portion. The method further includes attaching a second band portion having a second distal end to a third distal end of the first band portion, wherein the third distal end of the first band portion is opposite of the first distal end of the first band portion. The opening is configured to (i) have an adjustment length of the second band portion, including the second distal end, be fed therethrough, and (ii) cause the cinch structure to apply a frictional force adjacent to the adjustment length of the second band portion. After the adjustment length of the second band portion is fed therethrough the opening defined by the cinch structure, an adjustable loop is formed having a first circumference around a wrist of a user. The frictional force applied by the cinch structure is configured to be maintained adjacent to the adjustment length of the second band portion while the adjustable loop is worn by the user, such that the first circumference of the adjustable loop is also maintained.

(E1) In accordance with some embodiments, a band structure is provided. The band structure includes a first portion of the band structure (e.g., the band portion 104 in FIGS. 1A-1C), the first portion of the band structure having (i) an embedded structural member configured to hold one or more signal-processing components in respective fixed positions within the first portion of the band structure, (ii) the one or more signal-processing components, which are coupled to the embedded structural member, and the one or more signal-processing components configured to at least partially process neuromuscular signals, and (iii) one or more neuromuscular-signal-sensing electrodes attached to the first portion of the band structure and electrically coupled to the one or more signal-processing components. The band structure also includes a second portion of the band structure (e.g., the band portion 102 in FIGS. 1A-1C). The first portion of the band structure and the second portion of the band structure are each configured to couple (e.g., directly to one another) to form a loop, the loop sized to accommodate a wrist of a user. For example, FIG. 1A illustrates the band portion 102 being coupled with the band portion 104 via the cinch structure 106.

(E2) In some embodiments of E1, the one or more neuromuscular-signal-sensing electrodes are distributed along a longest dimension of the first portion of the band structure. And the band structure further includes a flexible printed circuit (FPC) (e.g., the FPC 800 in FIGS. 8A-8G), of the embedded structural member, that is embedded along the longest dimension of the first portion of the band structure. In accordance with some embodiments, the FPC includes the one or more signal-processing components (e.g., the signal-processing components 802a-802f in FIG. 8A), respective signal-processing components of the one or more signal-processing components communicably coupled with respective neuromuscular-signal-sensing electrodes of the one or more neuromuscular-signal-sensing electrodes.

In some embodiments, electrodes disposed along an inner surface (e.g., wrist-facing) of the FPC are configured to be dispersed by at least a minimum separation distance, in order to increase an aggregated score of the biopotential-signal sensing structures for sensing such signals (as discussed with respect to FIGS. 16A-16B). In some embodiments, one or more of the electrodes are electromyography (EMG) electrodes configured to detect EMG signals from the body of the user. For example, the EMG topology represented by FIG. 13 can be representative of the locations of the EMG electrodes on the wearable electronic device (e.g., the wearable electronic device 100 in FIGS. 1A-1C). In some embodiments, the FPC is made of one or more of polyamide resin, polyurethane resin, and nylon resin. In some embodiments, glob-top sealing is applied to one or more of the signal-processing components (e.g., AFEs).

(E3) In some embodiments of E2, the band structure further includes a compute core attached to the first portion of the band structure and the second portion of the band structure. A first end of the FPC is coupled with the compute core. The compute core includes a centralized processor, which can be at least part of a printed circuit board (PCB) (e.g., the PCB 450 in FIG. 4C) that is housed in the compute core. The centralized processor can be configured to process respective neuromuscular signals from multiple of the one or more signal-processing components. In some embodiments, the compute core is housed by one or more of (i) a top case (e.g., a top case 406 in FIG. 4A), and (ii) a bottom case (e.g., a bottom case 404 in FIG. 4B). When coupled, the top case and the bottom case can house electronic components, such as a PCB (e.g., a PCB 450 in FIG. 4C).

(E4) In some embodiments of E2-E3, the FPC is coupled with the compute core by one or more stainless-steel micro-fasteners. A portion of the FPC extends beyond the one or more stainless-steel micro-fasteners, such that it physically contacts a coupling component of the centralized processor.

(E5) In some embodiments of E2-E4, the FPC further includes a bend stiffening component configured to prevent axial rotation of the longest dimension of the first portion of the band structure, including the FPC.

(E6) In some embodiments of E5, the bend stiffening component is comprised of polyimide.

(E7) In some embodiments of E5-E6, the bend stiffening component is coupled with the FPC via a low-pressure molding process that encapsulates and environmentally protects electronic components of the FPC, including the one or more signal-processing components.

(E8) In some embodiments of E2-E7, the band structure further includes a strain relief component (e.g., the strain relief strand 824 in FIG. 8C) that extends along the longest dimension of the first portion of the band structure, the strain relief component configured to prevent elongation strain of the FPC. In some embodiments, the strain-relief component is made of Vectran. In some embodiments, heat treatment applied to the strain relief component increases its tensile strength. In some embodiments, the strain-relief component can also serve as a bend stiffening component for preventing the FPC from rotating in an axial direction around its length.

(E9) In some embodiments of E2-E8, the band structure further includes an insertable tool (e.g., the overmold tool 840 shown in FIG. 8E). The insertable tool is configured to hold down the FPC against an internal surface of the first portion of the band structure, such that respective electrodes of the one or more electrodes remain in substantially fixed relative positions along the longest dimension of the first portion of the band structure. In some embodiments, one or more of the hold-down blocks of the overmold tool 840 are made of thermo-plastic polyurethane (TPU).

In some embodiments, the insertable tool is configured to receive an overmolding layer that encapsulates at least a portion the FPC, while allowing the one or more electrodes to remain exposed. In some embodiments the overmolding layer (e.g., the overmolding layer 850) is made of a combination of a thermoplastic polyurethane (TPU) and a thermoplastic elastomer (e.g., TPSiV). In some embodiments the thermoplastic elastomer has a hardness range of Shore A 30-80. In some embodiments, the thermoplastic elastomer has a hardness range of Shore A 50-60.

(E10) In some embodiments of E2-E9, the band structure further includes one or more receiving structures. A first molding operation is performed to mold the one or more receiving structures to one or more discrete along the longest dimension of the first portion of the band structure. Respective receiving structures of the one or more receiving structures are coupled with respective signal-processing components of the one or more signal-processing components. A second molding operation is performed to encase a substantial portion of the FPC and the one or more receiving structures while allowing coupling components of the one or more receiving structures to remain exposed. After the second molding operation is performed, coupling the respective electrodes of the one or more electrodes to respective coupling components of the one or more receiving structures is performed.

(E11) In some embodiments of E2-E10, a plurality of shot-molding operations are performed at the band structure, wherein respective shot-molding operations of the plurality of shot-molding operations include disposing distinct respective material layers of a plurality of material layers along the FPC.

(E12) In some embodiments of E11, the band structure further includes a textile layer configured to encapsulate substantially all of the plurality of material layers of the plurality of shot-molding operations performed at the band structure.

(E13) In some embodiments of E2-E12, at least two of the one or more neuromuscular-signal-sensing electrodes are electromyography (EMG) electrodes of a dual-channel EMG sensor.

(E14) In some embodiments of E2-E13, the first portion of the band structure includes a paramagnetic metal chain (e.g., the paramagnetic chain 844 shown in FIG. 8E), which can be configured to counteract torsional force applied to the FPC. In some embodiments, the paramagnetic chain is configured to couple with one or more magnets or other metallic structures of a second band portion (e.g., the band portion 102 in FIGS. 1A-1C) of a wearable electronic device that includes the FPC 800. In some embodiments, the paramagnetic chain is coupled with elastomer material.

(E15) In some embodiments of E1-E14, the one or more signal-processing components include one or more low-power instrumentation amplifiers configured to amplify signals from one or more electrodes, wherein the one or more low-power instrumentation amplifiers are comprised of titanium. In some embodiments, the titanium low-power instrumentation amplifiers are configured to be resistant to high-temperature high-humidity (HTHH) conditions.

(E16) In some embodiments of E1-15, the first portion of the band structure and the second portion of the band structure are permanently coupled via an overmolding process that encapsulates electronic components of the band structure.

(E17) In some embodiments of E16, a strain relief layer configured to prevent elongation stress of the band structure, wherein the strain relief layer extends along respective longest dimensions of each of the first portion of the band structure and the second portion of the band structure. In some embodiments, the strain relief layer includes a high-performance, multifilament yarn spun from liquid crystal polymer.

(E18) In some embodiments of E1-E17, neither of the first or second portions of the band structure are coupled to a display. In some embodiments, the band structure does not include any displays. In some embodiments, the band structure includes one or more configurable LEDs for providing indications to a user, which may be used in addition or alternatively to a touch-sensitive display. In some embodiments, the second portion of the band structure does not include any electronic components.

(E19) In some embodiments of E18, the second portion of the band structure includes a bend stiffening component configured to prevent longitudinal rotation of a longest dimension of the first portion of the band structure, while the first band portion and the second band portion are couple around a wrist of a user.

(E20) In some embodiments of E1-E19, the embedded structural member is attached to a plurality of float clamps distributed along a longest dimension of the first portion of the band structure.

(F1) In some embodiments, a wrist-wearable device is provided. The wrist-wearable device includes an electronic display, and memory that includes instructions, which when performed at a processor of the wrist-wearable device, cause execution of functions at one or more of the electronic display and one or more sensors of the wrist-wearable device. The wrist-wearable device further includes a band structure coupled with the electronic display, the band structure, including a first portion and a second portion. The first portion of the band structure includes an embedded structural member configured to hold one or more signal-processing components in respective fixed positions within the first portion of the band structure. The one or more signal-processing components coupled to the embedded structural member, and the one or more signal-processing components configured to at least partially process neuromuscular signals. The first portion further includes one or more neuromuscular-signal-sensing electrodes attached to the first portion of the band structure and electrically coupled to the one or more signal-processing components. The second portion does not include any electronic components. The first portion of the band structure and the second portion of the band structure are each configured to couple directly to one another to form a loop, the loop sized to accommodate a wrist of a user.

(G1) In some embodiments, a method for manufacturing a band structure is provided. The method for manufacturing the band structure includes coupling one or more signal-processing components to an embeddable structural member, wherein the embeddable structural member is configured to hold the one or more signal-processing components in respective fixed positions within a first portion of the band structure. The method for manufacturing the band structure further includes embedding the embeddable structural member into the first portion of the band structure. The method for manufacturing the band structure further includes attaching one or more neuromuscular-signal-sensing electrodes to the first portion of the band structure, wherein the neuromuscular-signal-sensing electrodes are electrically coupled to the one or more signal-processing components that are coupled with the embeddable structural member. And the method of manufacturing further includes coupling the first portion of the band structure to a second portion of the band structure, the second portion of the band structure not including any electrical components.

(G2) In some embodiments of G1, the method further includes performing a first shot-molding operation, wherein the first shot-molding operation includes molding together a flexible printed circuit (FPC) of the embeddable structural member and a bend stiffening component. The method of manufacturing further includes performing a second shot-molding operation, wherein the second shot-molding operation includes molding together one or more receiving structures to discrete locations corresponding to the respective fixed positions of the one or more signal-processing components. The method of manufacturing further includes overmolding the embeddable structural member with a soft elastomer material such that all electronic components of the embeddable structural member are substantially encapsulated and environmentally protected.

(H1) In some embodiments, a biopotential-signal sensor structure is provided (e.g., the biopotential-signal sensing structure 702 in FIGS. 7A to 7C). The biopotential-signal sensor structure includes a carrier component configured to hold two biopotential-signal-sensing contact points that are configured to be in contact with skin of a user. The carrier component electrically separates the two biopotential-signal-sensing contact points from one another. The carrier component and the biopotential-signal-sensing contact points combine to produce a seamless structure configured to be coupled with a wearable band. When viewed in a cross-section along a horizontal plane, the seamless structure has a major dimension that is at least three times as large as a minor dimension of the seamless structure when viewed in the cross-section. When the seamless structure is coupled with the wearable band, (i) the major dimension of the seamless structure is located substantially perpendicular to the minor dimension of the wearable band, where the major and minor dimensions of the wearable band are located in an additional horizontal plane that is parallel to the horizontal plane. Each of the two biopotential-signal-sensing contact points extend above a wrist-facing surface of a wearable device, such that when the wearable device is worn, each of the two biopotential-signal-sensing contact points is at a predetermined skin depression depth. As described herein, substantially perpendicular means within an industry-standard tolerance of absolute perpendicularity (e.g., plus or minus five degrees of 90 degrees). In some embodiments, substantially perpendicular means within plus or minus 15 degrees of 90 degrees (e.g., 75 degrees to 105 degrees).

In some embodiments, one or more of the contact points are stamped to a bottom surface of the compute core 108. In some embodiments, the stamped contacts can have surfaces area of between 20-40 millimeters.

(H2) In some embodiments of H1, each of the biopotential-signal-sensing contact points defines a predefined geometrical shape having a length and a width of between three millimeters and eight millimeters.

(H3) In some embodiments of H1-H2, a separating region, of the carrier component, that electrically separates the two biopotential-signal-sensing contact points has a separation length of between 10 and 30 millimeters.

(H4) In some embodiments of H1-H3, each of the two biopotential-signal-sensing contact points are partially supported by a set of springs to allow for a stable impedance to be maintained while receiving the received signal from the two biopotential-signal-sensing contact points.

(H5) In some embodiments of H4, an AFE for processing neuromuscular signals received from the two biopotential-signal-sensing contact points is coupled to the two biopotential-signal-sensing contact points via the set of springs. In some embodiments, a cross-sectional width of the seamless structure determines a maximum cross-sectional width of the AFE.

(H6) In some embodiments of H1-H5, the one or more attachment mechanisms are placed beneath each of the biopotential-signal-sensing contact points. In some embodiments, the one or more attachment mechanisms are configured to attach to respective coupling structures located on the carrier component.

(H7) In some embodiments of H1-H6, the carrier component is overmolded (e.g., injection molded) onto the biopotential-signal-sensing contact points to be combined, and is then milled to produce the seamless structure.

(H8) In some embodiments of H1-H7, a textile wrap for forming an exterior surface of the wearable device is sandwiched between the one or more attachment mechanisms and the seamless structure.

(H9) In some embodiments of H1-H8, the AFE is part of a flexible printed circuit (FPC) stack and the FPC stack and the one or more attachment mechanisms are secured to the FPC stack.

(H10) In some embodiments of H9, the one or more attachment mechanisms are secured to the FPC stack via an adhesive (e.g., HB Fuller EH9698B, Loctite 3542).

(H11) In some embodiments of H1-H10, the carrier component is made of one or more of nylon, polyphenylene sulfide (PPS), polycarbonate (PC), acrylonitrile butadiene styrene (ABS) (e.g., a combination of PC and ABS). In some embodiments, the carrier is injection molded onto the biopotential-signal sensor structure).

(H12) In some embodiments of H1-H11, the carrier component is made of one or more of stainless steel (e.g., SUS 316), and brass (e.g., C6802).

(H13) In some embodiments of H1-H12, the seamless structure has a surface finishing made of a coating or a plating (e.g., a 0.3 micrometer titanium finishing combined with a one micrometer diamond-like carbon; a three to five micrometer finishing combined with a 1-2.5 micrometer copper, tin, zinc alloy finishing and a 1.3 micrometer gold finishing; and a physical vapor deposition (PVD) coating).

(H14) In some embodiments of H1-H13, the biopotential-signal-sensing contact points are etched to provide better adhesion the carrier component.

(H15) In some embodiments of H1-H14, a cross-sectional width of the seamless structure determines a maximum cross-sectional width of the AFE.

(H16) In some embodiments of H1-H15, the one or more attachment mechanisms configured for securing the seamless structure to the wearable device include one or more of: snap fasteners, coil springs, glue wells, double wall glue channel, reverse glue channel, single wall glue channel, fuzz buttons, two pins and two holes, and micro-fasteners (e.g., microPEM tacks).

(H17) In some embodiments of H1-H16, a spring (e.g., either of the springs 730a and 730b) is attached to a bottom surface of the carrier component in the process of assembling the biopotential-signal sensor structure. In some embodiments, the spring is used to maintain consistent contact between a component of the biopotential-signal sensor structure (e.g., an EMG electrode) and another processing component (e.g., a signal processing component of a flexible printed circuit). In some embodiments, the spring is configured to provide a lower magnitude of force when it is further extended towards its uncompressed length.

(H18) In some embodiments of H1-H17, the carrier component includes at least one protruding hollow structure configured to snap into a corresponding pin-shaped receiver. In some embodiments, the pin-shaped receiver can be a component of a band structure attached to a wearable electronic device. In some embodiments, an adhesive can be used to provide an additional fastening force between the protruding hollow structure and the pin-shaped receiver.

(H19) In some embodiments of H1-H18, a shape profile of the carrier component is selected from a group consisting of a stadium shape, a discorectangle shape, a sausage shape, a pill shape, a squectangle, and an obround.

(H20) In some embodiments of H19, each of the two biopotential-signal-sensing contact points define vertical insets along opposite outer surfaces of the shape profile of the carrier component, and each of the two biopotential-signal-sensing contact points have respective widths along the minor dimension of the carrier component, each of the respective widths being within three to eight millimeters.

(H21) In some embodiments of H20, the respective widths of each of the two biopotential-signal-sensing contact points, along the minor dimension of the carrier component, is five millimeters.

(H22) In some embodiments of H1-H21, the major dimension of the seamless structure is between four to six times as large as the minor dimension of the seamless structure.

(H23) In some embodiments of H1-H22, the cross-section along the horizontal plane is vertically located at a midpoint of a height of the carrier component.

(H24) In some embodiments of H1-H23, the carrier component is configured to electrically separate the two biopotential-signal-sensing contact points by a separation distance of between five to 10 millimeters.

(I1) In some embodiments, a method of manufacturing a biopotential-signal sensor structure with two conductive contact points is provided. The method of manufacturing includes overmolding a carrier component onto two biopotential-signal-sensing contact points to produce the biopotential-signal sensor structure, wherein after the overmolding, each of the two biopotential-signal-sensing contact points has a first shape and the carrier component has a second shape. The method of manufacturing further includes milling the biopotential-signal sensor structure such that each of the of the two biopotential-signal-sensing contact points has a third shape distinct from the first shape and the carrier component has a fourth shape distinct from the second shape, wherein the biopotential-signal sensor structure becomes a seamless structure after the milling, wherein the biopotential-signal sensor structure is configured to allow multiple neuromuscular signal sensors to be placed on a wearable device (e.g., the seamless structure has a longitudinal dimension that is less than a latitudinal dimension). The method of manufacturing, wherein each of the two biopotential-signal-sensing contact points extends above a wrist-facing surface of the wearable device, such that when the wearable device is worn, each of the two is at a predetermined skin depression depth.

(I2) In some embodiments of I1, the biopotential-signal sensor structure is configured to be inserted into a band of the wearable device.

(I3) In some embodiments of I1-I2, one or more processing components are configured to be coupled to a machined dual-channel biopotential-signal sensor structure that is configured to process a component of a received signal from the machined dual-channel biopotential-signal sensor structure.

(I4) In some embodiments of I1-I3, the method includes coating the machined dual-channel biopotential-signal sensor structure to prevent corrosion.

(J1) In some embodiments, a wearable band includes a textile-based material having a geometrically shaped opening to define a compute-core region. The compute-core region is arranged to seamlessly surround a perimeter of a compute core of a wearable electronic device, the compute core being configured to process electrical signals for the wearable electronic device. The geometrically shaped opening includes a portion of textile material that is angled relative to a first adjacent portion of the geometrically shaped opening to allow for coupling of the geometrically shaped opening with the perimeter of the compute core. In some embodiments, one or more components of an FPC distributed along a length of the band portion 104 are configured to electronically couple with the compute core 108 within the compute-core region of the textile-based material.

(J2) In some embodiments of J1, the perimeter of the compute core includes a connection point between a top case of the compute core and a bottom case of the compute core. The connection point includes the portion of textile material, tucked at an angle relative to the first adjacent portion of the geometrically shaped opening within a seam of the compute core.

(J3) In some embodiments of J1-J2, the connection point includes an adhesive for adhering the portion of textile material that is angled relative to the first adjacent portion of the geometrically shaped opening to the compute core.

(J4) In some embodiments of J1-J3, the textile-based material is reinforced internally with an adhered polymer.

(J5) In some embodiments of J1-J4, the textile-based material is reinforced internally and externally with an adhered polymer.

(J6) In some embodiments of J1-J5, the textile-based material is partially produced using a polymer-based yarn.

(J7) In some embodiments of J6, the polymer-based yarn is a thermoplastic polyurethane (TPU).

(J8) In some embodiments of J1-J7, a portion of the compute core is exposed and another portion of the compute core is surrounded by the textile-based material.

(J9) In some embodiments of J1-J8, the textile-based material includes another geometrically shaped opening for one or more magnets, wherein the one or more magnets are coplanar to an edge of the other geometrically shaped opening.

(J10) In some embodiments of J9, the wearable band further includes an internal magnetic strip opposite of the one or more magnets, allowing the one or more magnets to magnetically couple to the internal magnetic strip when worn on a wrist of a user.

(J11) In some embodiments of J1-J10, the textile-based material encases a foam core, wherein the foam core provides rigidity to the unitary band.

(J12) In some embodiments of J11, a dimension of the foam core is adjusted around the geometrically shaped opening. In some embodiments, the foam core is adjusted by tapering the foam core around the geometrically shaped opening. In some embodiments, the foam core is adjusted by tapering the foam core around the geometrically shaped opening. In some embodiments, another material (e.g., co-molded elastomeric wings, or a sheet) is placed between the foam core and is the geometrically shaped opening. In some embodiments, there is a transition zone between the foam core and the compute core, to allow for better bending of the unitary band structure around the edge of the compute core.

(J13) In some embodiments of J1-J12, a seamless material surrounding the perimeter of the compute core includes the textile-based material terminates coplanar to an edge of the compute core.

(J14) In some embodiments of J1-J13, one or more light-emitting diodes (LEDs) are placed beneath an exterior surface of the textile-based material and are configured to transmit visible light to provide status indicators of the wearable electronic device corresponding to the unitary band. In some embodiments, the LED provides at least 100 klux.

(J15) In some embodiments of J1-J14, processing electrical signals for the wearable electronic device corresponding to the unitary band includes processing a plurality of neuromuscular signals.

(J16) In some embodiments of J15, the textile-based material is also configured to couple with neuromuscular-signal sensors that detect the plurality of neuromuscular signals to be processed at the compute core.

(J17) In some embodiments of J1-J16, the portion of textile material that is angled relative to the first adjacent portion of the geometrically shaped opening is angled at 55 degrees or greater.

(J18) In some embodiments of J1-J17, at least one flange structure extends outward into a band portion of the wearable band in a direction that is substantially parallel to the band portion.

(K1) In some embodiments, a method of manufacturing a wearable band is provided (e.g., the method 1700). The method includes providing an internal band component (e.g., the internal band component 1730, the FPC 800) that includes a plurality of sensor-holding structures (e.g., the sensor-holding structures 1732-1 to 1732-6) coupled with the internal band component. The method further includes sheathing the internal band component with a tubular textile band cover, such that the tubular textile band cover substantially surrounds each respective sensor-holding structure of the plurality of sensor-holding structures, thereby producing a covered band portion of the wearable band. The method further includes providing a plurality of biopotential-signal-sensing components configured to be coupled to respective sensor-holding structures of the plurality of sensor-holding structures. The method further includes cutting, via a first laser-cutting operation performed by one or more lasers of a laser-cutting device, sensor-placement openings at respective sensor locations of the covered band portion, with each respective sensor location corresponding to a respective sensor-holding structure of the plurality of sensor-holding structures. And the method further includes coupling the plurality of biopotential-signal-sensing components to the respective sensor-holding structures of the plurality of sensor-holding structures, while the sensor-holding structures are located at the respective sensor locations.

(K2) In some embodiments of K1, the method of manufacturing further includes, before sheathing the internal band component with the tubular textile band cover, attaching a set of textile-piercing components to respective sensor-holding structures of the plurality of sensor-holding structures. And the method further includes, after sheathing the internal band component, (i) causing the textile-piercing components to pierce a set of holding-structure openings of the tubular textile band cover, wherein the cutting of the set of holding-structure openings is based on respective locations of the sensor-holding structures, and (ii) removing the textile-piercing components form the respective sensor-holding structures of the plurality of sensor-holding structures.

(K3) In some embodiments of K1 or K2, the tubular textile band cover is comprised of infrared transparent (IR-transparent) material, such that substantially all of an amount of IR light provided by the one or more lasers of the laser-cutting device is not absorbed as it passes through the tubular textile band cover.

(K4) In some embodiments of any of K1 to K3, the internal band component includes a shielding component configured to prevent a laser provided by a light source of a laser cutter performing the first laser-cutting operation from cutting through the internal band component.

(K5) In some embodiments of K4, the method further includes, cutting, via the laser cutter, a magnet-receiving hole at a location corresponding to an end of a second portion of the covered band portion. And the method further includes (i) removing material from the magnet-receiving hole on the covered band portion, and (ii) adhering a magnet into the magnet-receiving hole, where the magnet is configured to secure the wearable band.

(K6) In some embodiments of any of K1 to K5, the method of manufacturing further includes mounting the covered band portion to an L-shaped tooling fixture, which includes (i) a first end point configured to fixedly hold a first band portion of the covered band portion at a first angle, (ii) a second end point configured to fixedly hold a second band portion of the covered band portion at a second angle, and (iii) a fixture point for cutting a geometrically shaped opening for housing a compute core located at a first point substantially orthogonal to respective orientations that the first and second band portions are being fixedly held in by the first and second end points of the L-shaped tooling fixture. And the method further includes, while the covered band portion is mounted to the L-shaped tooling fixture, cutting a geometrically shaped opening into the tubular textile band cover, the geometrically shaped opening configured to receive a compute core.

(K7) In some embodiments of K6, the method of manufacturing further includes, before cutting the geometrically shaped opening into the tubular textile band cover, adhering an inner case of the compute core to a compute-core location within an interior of the tubular textile band. In some embodiments, the inner case is configured to couple with an outer case of the compute core after the geometrically shaped opening is cut into the tubular textile band cover.

(K8) In some embodiments of any of K1 to K7, the method of manufacturing further includes, providing, to a first layer of the covered band portion, a hot melt polyurethane reactive (HMPUR) adhesive. In some embodiments, (i) the HMPUR adhesive is applied to the first layer while the HMPUR adhesive is heated to a first temperature that is greater than or equal to 105 degrees Celsius, and (ii) after cooling the HMPUR adhesive to a second temperature, a second layer of the covered band portion is placed onto the HMPUR adhesive that was applied onto the first layer of the covered band portion. In some embodiments, while the second layer is placed over the HMPUR, the HMPUR is heated back to the first temperature (e.g., or a temperature that is higher than the first temperature).

(K9) In some embodiments of K8, the method of manufacturing further includes, while the second layer is placed on the HMPUR adhesive and the HMPUR adhesive is being heated, applying at least one bar of pressure to the HMPUR for at least 45 seconds.

(K10) In some embodiments of any of K1 to K9, the method of manufacturing further includes (i) coupling a cinchable closure structure to a first end of a first band portion of the covered band, and (ii) applying an adhesive polymer to a first portion of the first end of the first band portion at a point offset from the first end, such that the adhesive polymer is configured to engage with an adjustment length of a second band portion of the covered band portion as the adjustment length of the second band portion is fed through the cinchable closure structure.

(L1) In accordance with some embodiments, a band structure is provided. A first portion of the band structure includes (i) one or more signal-processing components configured to at least partially process biopotential signals, (ii) an embedded structural member configured to hold one or more signal-processing components in respective fixed positions within the first portion of the band structure, and (iii) one or more biopotential-signal-sensing electrodes attached to the first portion of the band structure and electrically coupled to the one or more signal-processing components. In some embodiments, the first portion includes a first sub-portion that includes a first subset of the one or more biopotential-signal-sensing electrodes located at the first region of a wrist of a user, the first region of the wrist associated with a higher level of biopotential signal activity; the first portion also includes a second sub-portion that includes a second subset of the one or more biopotential-signal-sensing electrodes located at a second region of the wrist of the user, the second region associated with a lower level of biopotential signal activity; and the band structure includes a second portion of the band structure, the second portion not including any electrical components, wherein the first portion of the band structure and the second portion of the band structure are each configured to couple to form a loop, the loop sized to accommodate a wrist of a user.

(L2) In some embodiments of L1, the first characteristic is one or more of (i) a first minimum density of the first subset of the one or more biopotential-signal-sensing electrodes that is greater than a second minimum density of the second subset of the one or more biopotential-signal-sensing electrodes, and (ii) a first activity level of the first subset of the one or more biopotential-signal-sensing electrodes that is greater than a second activity level of the second subset of the one or more biopotential-signal-sensing electrodes.

(L3) In some embodiments of L1 or L2, a first respective end of the first portion of the band structure includes a coupling mechanism for coupling to an adjustment length of a second respective end of the second portion, and the coupling mechanism is configured to be located at a portion of a wrist of the user having a lower level of biopotential-signal-activity.

(M1) In accordance with some embodiments, a wearable electronic device is provided. The wearable electronic device includes a compute core (e.g., the compute core 2200 described with respect to FIG. 21). The compute core includes a skin contact surface and defines a cavity. The cavity is at least partially configured to house a battery, an electrode assembly located at the skin contact surface, an analog front end associated with the electrode assembly, a main logic board, and a metallic base plate (e.g., the metallic base plate 2006 shown in the exploded view in FIG. 20). The electrode assembly is configured to sense neuromuscular signals. The analog front end is configured to partially process the sensed neuromuscular signals into partially processed neuromuscular signals (e.g., performing at least some of the operations for digitizing and quantifying values related to detection of the biopotential signals). The main logic board is configured to receive the partially processed neuromuscular signals, and determine gestures based on the partially processed neuromuscular signals. The metallic base plate is configured to provide an electrical ground for the electrode assembly, and electrically shield the electrode assembly from electrical and magnetic noise. At least some of the electrical and magnetic noise is from at least one of the main logic board and the battery. And the analog front end is placed on a first side of the metallic base plate and the main logic board is placed on a second side that is opposite to the first side of the metallic base plate. In some embodiments, the battery provides energy to the electrode, the analog front end, and/or the main logic board. In some embodiments, the electrode is proud (e.g., projecting slightly outward) from a lower surface of the compute core or wearable electronic device.

(M2) In some embodiments of M1, the compute core further includes a mid-plate configured to provide a physical shield at a top portion of the battery, wherein the mid-plate is configured to physically connect to the bottom case of the compute core via physical tabs extending substantially orthogonal to the metallic base plate. And the compute core further includes a printed circuit board (PCB) placed on top of the mid-plate, the PCB configured to process partially processed neuromuscular signals sensed at other locations along a band portion, distinct from the compute core, of the wearable electronic device.

(M3) In some embodiments of M2, a first end of the mid-plate defines a cutout portion configured to receive one or more flexible printed circuits (FPCs) extending from other portions of the compute core (e.g., from a dome flex component located below the mid-plate). At least one of the one or more FPCs extending from other portions of the compute core are configured to electronically couple with the PCB placed on top of the mid-plate. For example, in accordance with some embodiments, electrodes on a bottom surface of the compute core are coupled with one or more electronic components (e.g., attached to a dome flex component) that are configured to partially process neuromuscular signals sensed by the electrodes, and a respective FPC of the one or more FPCs extends from the one or more electronic components past the base plate and the mid plate to couple with the PCB, such that the partially-processed neuromuscular signals can be processed further by the PCB placed on the mid-plate.

(M4) In some embodiments of any one of M1 to M3, the electrode assembly includes two electrode portions (e.g., machined and/or die-cast electrode portions, which may be separate or parts of a single contiguous structure), where each of the two electrode portions of the plurality of machined electrode portions has a respective first side configured to protrude into a sensor-skin interface of a wearer of the wearable electronic device (e.g., skin of the user's wrist that does not include a large amount of bone). In some embodiments, the first sides of the respective machined electrode portions form a portion of the skin-contacting surface of the compute core. The electrode includes an electrode spacer (e.g., of a plurality of electrode spacers comprising the electrode assembly) configured to be inserted between the two electrode portions to electrically separate the two electrode portions. And the electrode includes an adhesive component configured to couple the two electrode portions and the electrode spacer to the skin contact surface of the compute core. In some embodiments, the lower surface of the compute core defines one or more electrode-placements surfaces (e.g., insets shaped to surround the composite structures formed by the plurality of machined electrode portions and the one or more electrode spacers).

(M5) In some embodiments of M4, each of the two electrode portions has a maximum protrusion depth of at least 0.5 millimeters while the two electrode portions are coupled to the skin contact surface of the compute core. In some embodiments, the maximum protrusion depths are greater than 0.75 millimeters, 1 millimeter, 1.25 millimeters, 1.5 millimeters, etc.

(M6) In some embodiments of M4 or M5, each of the two electrode portions are configured to form respective opposing edges of the electrode assembly, and the electrode assembly includes a third electrode portion configured to be placed in between the two electrode portions, where the third electrode portion has a greater surface area than either of the two electrode portions.

(M7) In some embodiments of M6, respective nearest edges of the two electrode portions are separated by at least a first separation distance (e.g., a point-of-contact (POC) gap), and respective nearest edges of each of the two electrode portions and the third electrode portion are separated by at least a second separation distance (e.g., a sensor-type gap). For example, each of the respective electrode portions may be separated by at least a POC gap of 0.8 to 1.2 millimeters, such that neuromuscular signals detected by each of the respective electrode portions are separately detectable. And each of the respective edge portions of the set of edge portions is separated by at least a sensor-type gape of 4 to 10 millimeters.

(M8) In some embodiments of any one of M4 to M7, the electrode assembly is formed by: (i) placing the two electrode portions in opposite positions within a fixture, (ii) adhering (e.g., via glue or another adhesive) the electrode spacers between the electrode portions, such that the electrode portions are electrically isolated from each other, and (iii) coupling two electrical contacts (e.g., fuzz buttons) to second sides of the two electrode portions, different from respective first sides of the machined electrode portions. As described herein, fuzz buttons, which may also be referred to herein as spring contact pins, are defined and/or characterized as comprising a high-performance electrical connection material that is configured to connect two or more electrically-conducting contacts (e.g., of each of the two electrode portions of the electrode assembly).

(M9) In some embodiments of any one of M1 to M8, the metallic base plate includes one or more protrusions (e.g., metal tabs) extending in a first direction that is substantially orthogonal to a plane defined by the metallic base plate (e.g., within 15 degrees of orthogonal to a flat plane defined by the base plate). The skin contact surface of the compute core is part of a bottom case of the compute core, wherein the bottom case is a rigid component that is that is configured to couple with the wearable electronic device to form the compute core. The one or more vertical pockets are defined at one or more seating locations of the bottom case of the compute core, where (i) the one or more vertical pockets are configured to receive each of the one or more protrusions of the metallic base plate, and (ii) the one or more vertical pockets have respective preconfigured depths such that they are configured to seat the metallic base plate at a particular height within the compute core to electrically ground the electrode.

(M10) In some embodiments of any one of M1 to M9, where the compute core further comprises an antenna (e.g., the LDS antenna component 470 shown in FIG. 4D) configured to communicate with one or more computing devices separate from the compute core (e.g., one or more processing components distributed along a band portion of the wearable electronic device, a remote server, etc.).

(M11) In some embodiments of any one of M1 to M10, the wearable electronic device further includes a band portion including one or more electrodes for processing biopotential signals of a user, wherein each respective electrode of the one or more electrodes is distributed at a distinct location along a major dimension of the band portion. And the wearable electronic device a flexible printed circuit (FPC) distributed along the band portion, configured to provide information about biopotential signals detected by the one or more electrodes to the compute core. In some embodiments, two or more electrodes are vertically stacked (e.g., having the same horizontal location along the major dimension, but having different respective vertical locations along a minor dimension of the band portion) at a particular location along the major dimension of the band portion.

(M12) In some embodiments of any one of M1 to M11, the compute core further comprises a linear resonant actuator (LRA) configured to provide haptic feedback to a wearer of the wearable electronic device, and the metallic base plate is configured to electrically shield the electrode from electrical and/or magnetic noise and/or physical disruption caused by actuation of the LRA. In other words, the base plate may be configured to prevent actuation of the LRA (e.g., one or more haptic events) caused by the wearer's interaction with the wearable electronic device from interfering with operations of the electrode from disruption that could cause degradation of performance.

(M13) In some embodiments of any one of M1 to M12, the wearable device further includes a dome flex component configured to receive electrical connections (e.g., via fuzz buttons) from the one or exposed electrodes, and including at least one extruding side wall portion configured to seat one or more electrical components above the battery (e.g., above the baseplate).

(M14) In some embodiments of any one of M1 to M13, the electrode assembly is a first electrode assembly, the cavity is configured to house a second electrode assembly, and each of the first and second electrode assemblies are positioned on corresponding sides of the skin contact surface of the compute core. For example, in some embodiments, the wearable device is configured to attach to a body part (e.g., a wrist) having a major dimension (e.g., an arm length) and a minor dimension (e.g., a wrist circumference), and the first and second electrodes are configured to be aligned at a same location along the major dimension, and at distinct locations along the minor dimension.

(M15) In some embodiments of M14, the first electrode assembly has a separation distance of 5 to 20 millimeters (e.g., 13 millimeters) from the second electrode assembly, where the separation distance is measured from respective opposing edges of the first and second electrode assemblies (e.g., an end-to-end distance). In some embodiments, each of the first and second electrodes has a midpoint, where the midpoint corresponds to the greatest amount of penetration depth of the respective electrode. In some embodiments, the respective midpoints of the first and second electrodes are separated by a midpoint separation distance of 10 to 30 millimeters (e.g., 19 millimeters).

(M16) In some embodiments of M14 or M15, the first and second electrode assemblies are attached to the skin contact surface of the compute core, such that respective lower surfaces of the first and second electrode assemblies are proud with respect to the skin contact surface of the compute core (e.g., slightly projecting from the skin contact surface), through a sequence of assembly steps, including (i) placing each of the first and second electrode assemblies (e.g., computer numerical control (CNC) machined electrodes) into a fixture for securely holding the first and second electrode assemblies during one or more subsequent assembly processes, wherein the first and second electrodes includes one or more defined openings on top surfaces of respective electrodes of the first and second electrodes; (ii) gluing electrode spacers between respective electrodes of the first and second electrodes, such that each respective electrode portion of the first and second electrodes is electrically insulated from each other respective electrode portion of the first and second electrodes; (iii) providing one or more fuzz buttons at the one or more defined openings on the top surfaces of the first and second electrodes, the one or more fuzz buttons configured to form an electrical contact with each of the first and second electrodes (e.g., direct contact, and/or electrical contact formed via a PCB that is separately coupled to each of the first and second electrodes); providing (e.g., via a calibration tool) a set of datums to respective bottom surfaces of the first and second electrodes; based on the set of datums, applying a pressure-sensitive adhesive (PSA) to the respective bottom surfaces of the first and second electrodes; and while the PSA is wet and applied to the respective bottom surfaces of the first and second electrodes, pressing the first and second electrodes to a mounting point on an inner surface of a bottom case of the compute core.

As one of skill in the art will appreciate, aspects of any of the above sets of example embodiments (e.g., a set of example embodiments A1-16, a set of example embodiments E1-E20, a set of example embodiments H1-H24, and a set of example embodiments J1-J18) can be combined with aspects of one of any of the other sets of embodiments, unless there is explicit disclosure in one of the aspects that prevents the respective aspects from being combined. For example, the band structure describe by the example embodiment E1 can include a cinch structure as described by the example embodiment A1, can include a plurality of the biopotential-signal sensing structures described by the example embodiment H1, and can also be an example of the wearable band described by the example embodiments J1, including at least one type of textile material and a compute-core region that is configured to seamlessly surround a perimeter of a compute core.

In some embodiments, the band portion is comprised of an elastomer material, and the at least one flange structure is comprised of a rigid material. In some embodiments, the flange is tapered such that a distal end of the flange, opposite the compute-core region, is narrower than a proximal end of the flange. In some embodiments, when a compute core is housed in the compute-core region, the compute-core region has a rounded lower surface, which can be based on the shape of the compute core housed in the compute-core region, according to some embodiments. In some embodiments, the flange can be tapered from a side opposite the rounded lower surface of the compute core (e.g., the flange 1048 in FIG. 10C). In some embodiments, the band portion is comprised of textile material and the flange is comprised of elastomer, or another flexible material (e.g., scrim).

In some embodiments, at least one band portion of the wearable band (e.g., the "dumb" band) includes wear-resistant material that is configured to be fed through a cinch structure configured to receive the band portion (e.g., the cinch structure in FIGS. 2A-2E). In some embodiments, the at least one band portion that includes wear-resistant material includes layers of one or more of polyurethane foam (e.g., Poron) and/or polyimide film (e.g., Kapton). In some embodiments, the wear-resistant material includes a first layer of polyurethane foam that is less than two millimeters, a second layer of polyurethane foam that is less than two millimeters, and a layer of polyimide film that is greater than two millimeters, where the polyimide film separates the first layer of polyurethane foam and the second layer of polyurethane foam.

In some embodiments, the textile-based material includes a band portion of a band that is coupled with the compute-core region, and the band portion defines at least one additional geometrically shaped opening configured to receive a portion of biopotential-signal sensor structure. In some embodiments, the biopotential-signal sensor structure has an overhang such that the geometrically shaped opening defined by the band portion of the textile-based material is configured to couple with a tapered portion of the biopotential-signal sensor structure below the overhang. For example, the overhang is meant to be larger than the geometrically shaped opening defined by the band portion of the textile material. In some embodiments, there is a thicker base portion of the biopotential-signal sensing structure (e.g., the carrier component of the biopotential-signal sensor structure in FIGS. 5A-5C) below the tapered portion, such that the overhang and the thicker base portion are separated by the tapered portion. In some embodiments, the overhang is between 0.5 millimeters and two millimeters around the entire perimeter of the tapered portion.

While text terms are used as a primary illustrative example herein, the skilled artisan will appreciate upon reading this disclosure that the inventive techniques discussed herein can also be used to allow for neuromuscular gesture control of additional types of inputs, including graphical inputs (such as images included near any of the text terms or emojis), attachment-type inputs (e.g., document attachments), and many other types of inputs that can be provided at wearable devices in addition to text-based inputs.

Any data collection performed by the devices described herein and/or any devices configured to perform or cause the performance of the different embodiments described above in reference to any of the figures discussed above is done with user consent and in a manner that is consistent with all applicable privacy laws. Users are given options to allow the devices to collect data, as well as the option to limit or deny collection of data by the devices. A user is able to opt-in or opt-out of any data collection at any time. Further, users are given the option to request the removal of any collected data.

It will be understood that, although the terms "first," "second," etc. can be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

The invention claimed is:

1. A band structure, comprising:
a first portion of the band structure, including:
an embedded structural member configured to hold one or more signal-processing components in respective fixed positions within the first portion of the band structure;
the one or more signal-processing components, which are coupled to the embedded structural member, and the one or more signal-processing components are configured to at least partially process neuromuscular signals;
a flexible printed circuit (FPC), of the embedded structural member, that is embedded along a longest dimension of the first portion of the band structure, wherein:
the FPC includes the one or more signal-processing components, respective signal-processing components of the one or more signal-processing components communicably coupled with respective neuromuscular-signal-sensing electrodes of the one or more neuromuscular-signal-sensing electrodes, and
the FPC includes a stiffening component configured to prevent axial rotation of the longest dimension of the first portion of the band structure, including the FPC; and
one or more neuromuscular-signal-sensing electrodes attached to the first portion of the band structure and electrically coupled to the one or more signal-processing components, the one or more neuromuscular-signal-sensing electrodes are distributed along the longest dimension of the first portion of the band structure; and
a second portion of the band structure, the second portion not including any electrical components, wherein:
the first portion of the band structure and the second portion of the band structure are each configured to couple to one another to form a loop, the loop sized to accommodate a wrist of a user.

2. The band structure of claim 1, comprising:
a compute core attached to the first portion of the band structure and the second portion of the band structure, wherein:
a first end of the FPC is coupled with the compute core; and
the compute core includes a centralized processor configured to process respective neuromuscular signals from multiple of the one or more signal-processing components.

3. The band structure of claim 2, wherein:
the FPC is coupled with the compute core by one or more micro-fasteners; and
a portion of the FPC extends beyond the one or more micro-fasteners, such that it physically contacts a coupling component of the centralized processor.

4. The band structure of claim 2, wherein the compute core and the band structure are configured to form a wrist-wearable device, and the wrist-wearable device does not include a display.

5. The band structure of claim 1, wherein the stiffening component is comprised of polyimide.

6. The band structure of claim 1, wherein the stiffening component is coupled with the FPC via a low-pressure molding process that encapsulates and environmentally protects electronic components of the FPC, including the one or more signal-processing components.

7. The band structure of claim 1, further comprising:
a strain relief component that extends along the longest dimension of the first portion of the band structure, the strain relief component configured to prevent elongation strain of the FPC.

8. The band structure of claim 1, wherein at least two of the one or more neuromuscular-signal-sensing electrodes are configured to be used to detect electromyography (EMG) signals, as part of a dual-channel EMG sensor.

9. The band structure of claim 1, wherein the first portion of the band structure includes a paramagnetic metal chain configured to counteract torsional force applied to the FPC.

10. The band structure of claim 1, wherein the embedded structural member is attached to a plurality of float clamps distributed along the longest dimension of the first portion of the band structure.

11. A wrist-wearable device, comprising:
a compute core configured to process neuromuscular signals to detect gestures performed by a hand of a user; and a band structure coupled with the compute core, the band structure including:
- a first portion of the band structure, the first portion having:
  - an embedded structural member configured to hold one or more signal-processing components in respective fixed positions within the first portion of the band structure;
  - the one or more signal-processing components, which are coupled to the embedded structural member, and the one or more signal-processing components are configured to at least partially process neuromuscular signals;
  - a flexible printed circuit (FPC), of the embedded structural member, that is embedded along a longest dimension of the first portion of the band structure, wherein:
    - the FPC includes the one or more signal-processing components, respective signal-processing components of the one or more signal-processing components communicably coupled with respective neuromuscular-signal-sensing electrodes of the one or more neuromuscular-signal-sensing electrodes, and
    - the FPC includes a stiffening component configured to prevent axial rotation of the longest dimension of the first portion of the band structure, including the FPC; and
  - one or more neuromuscular-signal-sensing electrodes attached to the first portion of the band structure and electrically coupled to the one or more signal-processing components, the one or more neuromuscular-signal-sensing electrodes are distributed along the longest dimension of the first portion of the band structure; and
- a second portion of the band structure, the second portion not including any electrical components, wherein:
  - the first portion of the band structure and the second portion of the band structure are each configured to couple to form a loop that extends from the compute core, the loop sized to accommodate a wrist of the user.

12. The wrist-wearable device of claim 11, wherein comprising:
the compute core attached to the first portion of the band structure and the second portion of the band structure,
a first end of the FPC is coupled with the compute core, and
the compute core includes a centralized processor configured to process respective neuromuscular signals from multiple of the one or more signal-processing components.

13. The wrist-wearable device of claim 11, wherein the compute core and the band structure are configured to form a wrist-wearable device, and the wrist-wearable device does not include a display.

14. The wrist-wearable device of claim 11, wherein:
the FPC is coupled with the compute core by one or more micro-fasteners; and
a portion of the FPC extends beyond the one or more micro-fasteners, such that it physically contacts a coupling component of the centralized processor.

15. The wrist-wearable device of claim 11, wherein the stiffening component is comprised of polyimide.

16. A method, comprising:
providing a first portion of a band structure, including:
- an embedded structural member configured to hold one or more signal-processing components in respective fixed positions within the first portion of the band structure;
- the one or more signal-processing components, which are coupled to the embedded structural member, and the one or more signal-processing components are configured to at least partially process neuromuscular signals;
- a flexible printed circuit (FPC), of the embedded structural member, that is embedded along a longest dimension of the first portion of the band structure, wherein:
  - the FPC includes the one or more signal-processing components, respective signal-processing components of the one or more signal-processing components communicably coupled with respective neuromuscular-signal-sensing electrodes of the one or more neuromuscular-signal-sensing electrodes, and
  - the FPC includes a stiffening component configured to prevent axial rotation of the longest dimension of the first portion of the band structure, including the FPC; and
- one or more neuromuscular-signal-sensing electrodes attached to the first portion of the band structure and electrically coupled to the one or more signal-processing components, the one or more neuromuscular-signal-sensing electrodes are distributed along the longest dimension of the first portion of the band structure; and
coupling a second portion of the band structure with the first portion of the band structure to form a loop sized to accommodate a wrist of the user, wherein the second portion does not include any electrical components.

17. The method of claim 16, further comprising:
attaching a compute core to the first portion of the band structure and the second portion of the band structure, wherein:
a first end of the FPC is coupled with the compute core; and
the compute core includes a centralized processor configured to process respective neuromuscular signals from multiple of the one or more signal-processing components.

18. The method of claim 17, further comprising: coupling the FPC with the compute core by one or more micro-fasteners, wherein a portion of the FPC extends beyond the one or more micro-fasteners, such that it physically contacts a coupling component of the centralized processor.

19. The method of claim 16, wherein the stiffening component is comprised of polyimide.

20. The method of claim 16, further comprising:
coupling the stiffening component with the FPC via a low-pressure molding process that encapsulates and environmentally protects electronic components of the FPC, including the one or more signal-processing components.

* * * * *